(12) United States Patent
Grant et al.

(10) Patent No.: US 12,360,101 B2
(45) Date of Patent: Jul. 15, 2025

(54) ELECTRONIC SYSTEMS AND METHODS FOR HEALTH ANALYSIS FROM BREATH

(71) Applicants: Nicholas Grant, Fort Collins, CO (US); Pierre Touma, Austin, TX (US); Luke Rhone, Midvale, UT (US)

(72) Inventors: Nicholas Grant, Fort Collins, CO (US); Pierre Touma, Austin, TX (US); Luke Rhone, Midvale, UT (US)

(*) Notice: Subject to any disclaimer, the term of this patent is extended or adjusted under 35 U.S.C. 154(b) by 391 days.

(21) Appl. No.: 17/958,388

(22) Filed: Oct. 1, 2022

(65) Prior Publication Data
US 2023/0108028 A1   Apr. 6, 2023

Related U.S. Application Data

(60) Provisional application No. 63/333,120, filed on Apr. 21, 2022, provisional application No. 63/251,556, filed on Oct. 1, 2021.

(51) Int. Cl.
*G01N 33/497*   (2006.01)
*G01N 27/04*   (2006.01)

(52) U.S. Cl.
CPC .......... *G01N 33/497* (2013.01); *G01N 27/04* (2013.01)

(58) Field of Classification Search
CPC .. G01N 33/497; G01N 27/04; G01N 33/4972; G01N 2033/4975; G01N 2033/4977; G01N 2001/2244; G01N 33/98; A61B 5/082; A61B 5/097; A61B 5/4845
USPC .............. 73/23.3; 600/532, 543; 422/84–85; 436/900
See application file for complete search history.

(56) References Cited

U.S. PATENT DOCUMENTS

| | | | |
|---|---|---|---|
| 11,175,268 B2 * | 11/2021 | Morgan | G01N 30/92 |
| 2017/0160221 A1 * | 6/2017 | Savoy | G01N 33/0031 |
| 2019/0056362 A1 * | 2/2019 | Morgan | G01N 30/95 |
| 2019/0331660 A1 * | 10/2019 | Nijsen | G01N 30/02 |
| 2021/0223220 A1 * | 7/2021 | Fan | G01N 33/0036 |

* cited by examiner

*Primary Examiner* — Eric S. McCall
*Assistant Examiner* — Anthony W Megna Fuentes

(57) ABSTRACT

A system and method for analyzing an air sample from a human uses a collection module that has a plurality of metal oxide semiconductor sensors that have different resistance responses to different gaseous compounds. A detector circuit reads the output of the sensors as analog signals for both ambient air and the air sample from the human. The ratios of the analog signals from ambient air and from the air sample can be compared to similar information from other health and unhealthy human subjects to determine the health status of the human. In one embodiment the system is used for breath analysis.

20 Claims, 45 Drawing Sheets

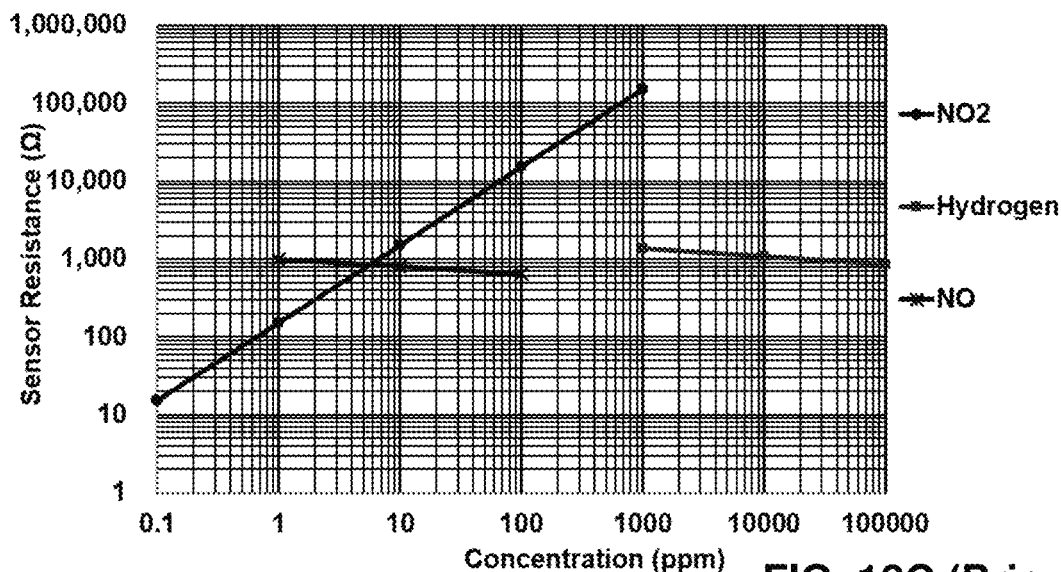
FIG. 12C (Prior Art)
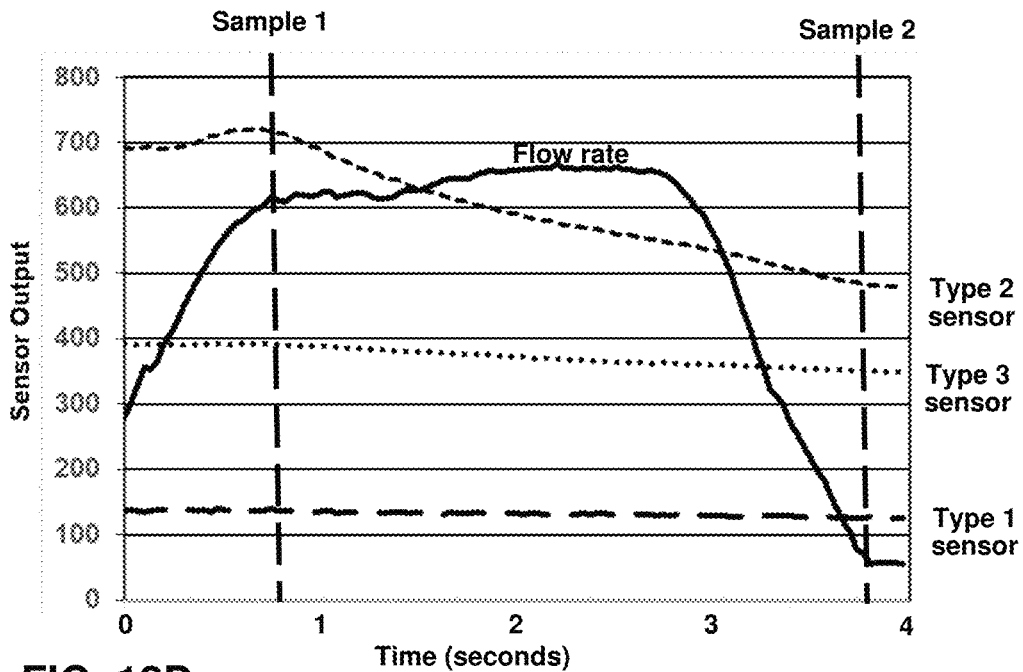
FIG. 12D
| | Type 1 Sensor Output | Type 2 Sensor Output | Type 3 Sensor Output |
|---|---|---|---|
| Sample 1 | 132 | 708 | 391 |
| Sample 2 | 124 | 577 | 358 |
| Ratio | 124/132 = 0.939 | 577/708 = 0.815 | 358/391 = 0.916 |
FIG. 12E

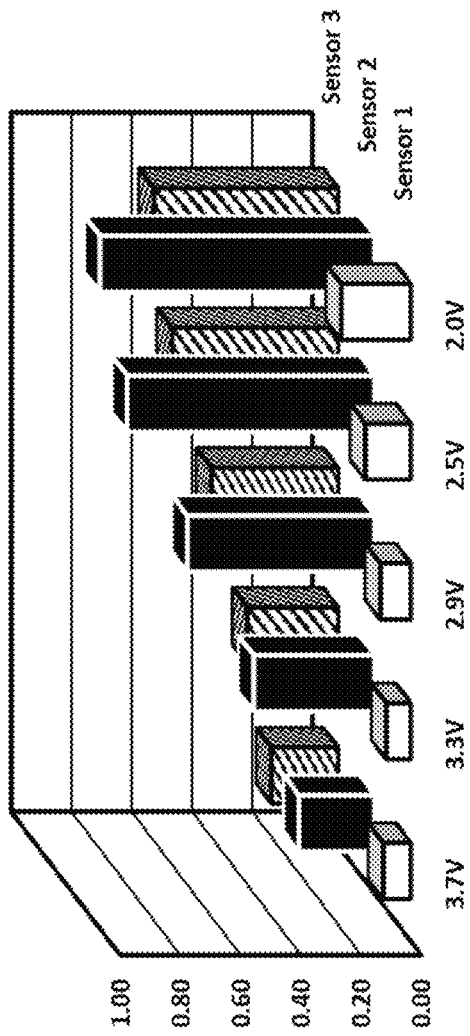
| | Gas 1/Ambient Air | | | | |
|---|---|---|---|---|---|
| | 3.7V | 3.3V | 2.9V | 2.5V | 2.0V |
| Sensor 1 | 0.09 | 0.08 | 0.10 | 0.15 | 0.23 |
| Sensor 2 | 0.25 | 0.40 | 0.62 | 0.82 | 0.91 |
| Sensor 3 | 0.22 | 0.30 | 0.42 | 0.55 | 0.61 |
FIG. 12F
FIG. 12G
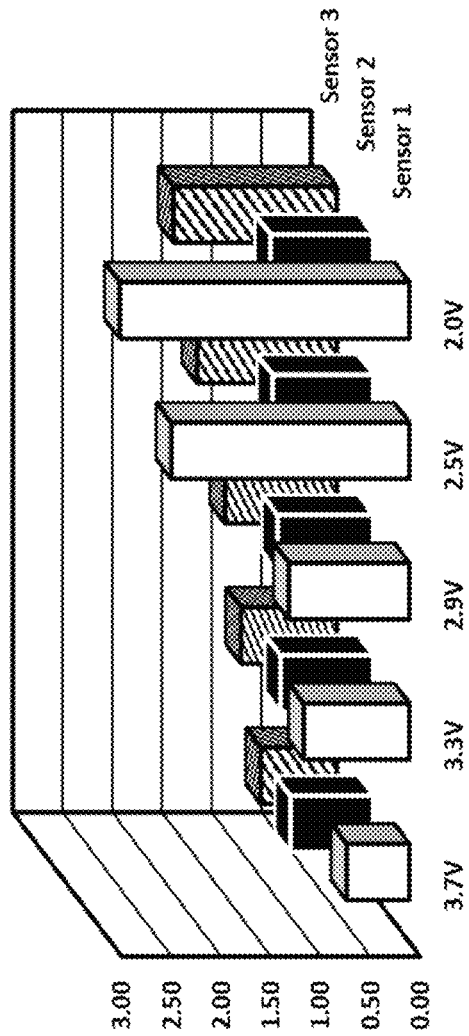
| | Gas 2/Ambient Air | | | | |
|---|---|---|---|---|---|
| | 3.7V | 3.3V | 2.9V | 2.5V | 2.0V |
| Sensor 1 | 0.63 | 1.06 | 1.21 | 2.39 | 2.91 |
| Sensor 2 | 0.83 | 0.93 | 0.96 | 1.01 | 1.03 |
| Sensor 3 | 0.76 | 0.96 | 1.12 | 1.40 | 1.64 |
FIG. 12H
FIG. 12I

ELECTRONIC SYSTEMS AND METHODS FOR HEALTH ANALYSIS FROM BREATH

CROSS REFERENCE TO RELATED APPLICATIONS

This application claims benefit of U.S. Provisional Patent Application Ser. No. 63/333,120 filed 21 Apr. 2022 and U.S. Provisional Patent Application Ser. No. 63/251,556 filed 1 Oct. 2021, which are incorporated by reference herein.

FIELD OF INVENTION

The invention(s) herein relate to systems and/or methods for observing and/or analyzing human breath, and more specifically systems/methods that use electronic transducers responsive to airborne biomarkers in breath to indicate health status and/or performance. The invention(s) herein can also relate to other human smells, such as those from sweat, urine, and feces.

BACKGROUND

The ancient Greeks were the earliest known people to identify that breath odors could be used for disease diagnosis. Early discoveries included that diabetes was related to the smell of rotten apples, and kidney failure was associated with a fish-like smell. In the 1970s, Linus Pauling and others showed that these odors comprise complex mixtures of volatile organic compounds (VOCs), volatile inorganic compounds (VICS), and other types of metabolites. Examples of volatile organic compounds include acetone, butyraldehyde, and isoprene. Examples of volatile inorganic compounds include hydrogen sulfide, ammonia, carbon dioxide, and water vapor (humidity). To date, over 3000 of such breath compounds have been identified. There are numerous scientific studies that relate relative concentrations of breath compounds to health status. The same applies to other human odors, such as those from sweat, urine, and feces.

Some animals are known to have a keener sense of smell than humans. For example, dogs have been used to detect drugs and explosives. Scientific studies have shown that dogs can detect lung cancer (from breath), breast cancer (from sweat), and COVID (from breath). Other animals, such as rats, bears, and mosquitos also have a keen sense of smell.

Sophisticated laboratory instrumentation and techniques have been used to relate human health conditions to vapor compounds and concentrations in exhaled breath and the odors in sweat, urine and feces. One example of such instrumentation are devices that use gas chromatography and mass spectrometry (GC-MS) to separate and measure concentrations of gaseous compounds. Such instrumentation is generally expensive and complex to operate.

Electronic sensors that respond to the chemical composition of a gas sample can be an inexpensive and simple alternative to the use of sophisticated laboratory instrumentation when measuring breath compounds. Systems and methods that use such sensors are typically called electronic noses or breathalyzers. The sensors in an electronic nose respond to physical or chemical characteristics of the compounds in a gas sample by making a change in some electronic property, such as electrical resistance, capacitance, inductance, voltage, current, etc. Metal oxide semiconductor (MOS) sensors are one example of such electronic sensors. MOS sensors detect gases by a chemical reaction that takes place when a gas come in contact with the semiconductor material in the sensor. For example, MOS sensors made from tin dioxide exhibit a decrease in resistance when the tin dioxide material comes in with a gas such as hydrogen, oxygen, alcohol vapor, or carbon monoxide. Another example is the use of electrochemical sensors, such as the fuel cell sensors that can be used for detecting breath alcohol and/or aldehydes. Another example is the use of infrared sensors. Such MOS, electrochemical, and infrared sensors are used in consumer carbon monoxide detectors, alcohol breathalyzers, and environmental gas detectors. One challenge with such sensors is that they are not specific to a particular compound. Thus, cross sensitivity and interference issues must be addressed if specific compounds, concentrations, and/or specific health conditions are to be detected.

Systems and/or methods that use chemical sensors can also have other sensors that are responsive to other breath characteristics such as volume, flow rate, pressure, temperature, time, etc. The output of all of the sensors (transducers) could be used to determine health impairments. Such systems and or methods can also be used for analysis of things other than human breath. Such systems and methods can be used to control the performance of a medical procedure, such as the dispensing of a drug, the application of a follow-on medical diagnostic test, and/or the performance of a surgical procedure.

BRIEF DESCRIPTION OF THE DRAWINGS

For a more complete understanding of the present invention and the advantages thereof, reference is made to the following description taken in conjunction with the accompanying drawing in which like reference numerals indicate like feature and wherein:

FIG. 12A, FIG. 12B, and FIG. 12C shows an example of the relationship of three sensor types a first sensor type to concentrations of a variety of gaseous compounds;

FIG. 12D shows an example of sensor outputs from three sensor types to an air sample with varying concentrations of breath compounds;

FIG. 12E shows a simple ratio analysis of some of the data shown in FIG. 12D;

FIG. 12F, FIG. 12G, FIG. 12H, and FIG. 12I show examples of a MOS sensor output ratio analysis for two different gases using three types of sensors operating at five different heater voltages;

Figure 1:
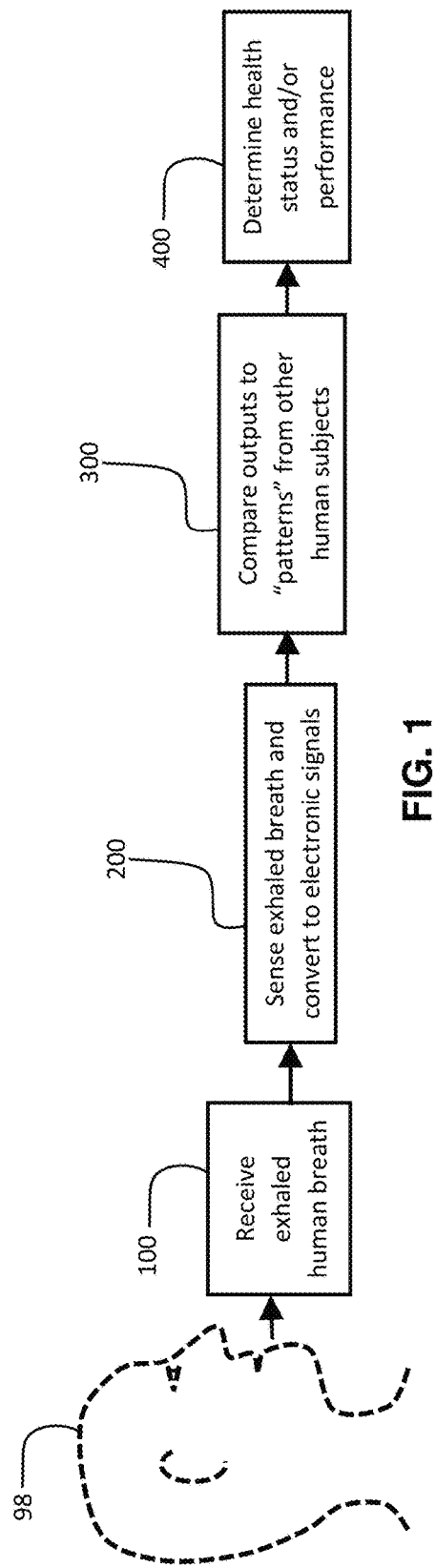
FIG. 1 shows a system and/or method for health and/or performance analysis directly from exhaled breath.

It should be understood that the drawings are not necessarily to scale. In certain instances, details that are not necessary for an understanding of the invention or that render other details difficult to perceive may have been omitted. It should also be understood that the invention is not necessarily limited to the particular embodiments illustrated herein.

To assist in the understanding of one embodiment of the present invention, the following list of components or features and associated numbering found in the drawings is provided herein:

| Number | Component or Feature |
|---|---|
| 98 | Human subject |
| 100 | Module and/or method for receiving exhaled human breath. Can also be used for protection and/or isolation. |
| 102 | Breath device (sensor unit) |
| 104 | System computer unit |
| 106 | Retort stand |
| 108 | Cable |
| 110 | Mouthpiece |
| 120 | Filter |
| 130 | Purge source |
| 140 | Controller |
| 150 | Ambient air source |
| 160 | Pump or fan |
| 200 | Module and/or method for converting information in exhaled human breath to electronic signals |
| 210 | First sensor chamber |
| 220 | Flow meter |
| 230 | Check valve (one-way valve) at filter output |
| 232 | Check valve (one-way valve) at device outlet |

| Number | Component or Feature |
|---|---|
| 234 | Purge source check valve (one-way valve) |
| 236 | Second check valve (one-way valve) |
| 260 | Second sensor chamber in series with first sensor chamber |
| 270 | Sensor chamber in parallel with first sensor chamber |
| 280 | Environmental controller |
| 300 | Module and/or method for comparing electronic signals with signal patterns from other human subjects |
| 310 | Electronic analyzer |
| 320 | Second electronic analyzer |
| 400 | Determine health status and/or performance. This can include health screening, disease detection, and determination of human performance. |
| 500 | Module and/or method for collecting exhaled gases using container or sorbent material |
| 510 | Adsorption/desorption module and/or method |
| 520 | Adsorption module |
| 530 | Desorption module |
| 600 | Module and/or method for offline analysis of collected gases |
| 610 | Module or method for comparing concentrations of collected gases with gas concentrations of healthy and unhealthy subjects |
| 710 | Test gas chamber |
| 712 | Second test gas chamber |
| 720 | Fluid source |
| 722 | Second fluid source |
| 730 | Tubing to connect first fluid source to first balloon |
| 732 | Tubing to connect second fluid source to second balloon |
| 740 | Stopper |
| 742 | Second stopper |
| 750 | Balloon |
| 752 | Second balloon |
| 760 | Test gas chamber outlet |
| 762 | Second test gas chamber outlet |
| 770 | Valve |
| 800 | Method for validating a breath analysis device, system, or method |
| 810 | Identify gas compounds in human breath that could indicate health status of interest. |
| 820 | Create test gases |
| 830 | Create breath analysis device |
| 832 | Attach device to test system |
| 840 | Validate sensitivity and specificity of device in response to test gases |
| 842 | Use device in test system with ambient air |
| 844 | Record data from device while being used with ambient air |
| 846 | Repeat ambient air test multiple times |
| 852 | Use device in test system with ambient air |
| 854 | Record data from device while being used with ambient air |
| 856 | Repeat test gas test multiple times |
| 860 | Generate ratios of sensor outputs |
| 890 | Breath tests of device with human subjects that have and don't have the health status of interest. |
| 895 | Validate sensitivity and specificity of device in response to health status of interest. |
| 900 | Automated system for compounding multiple gaseous sources to produce synthetic breath |
| 902 | Peristaltic pump |
| 904 | Peristaltic pump |
| 906 | Peristaltic pump |
| 908 | Peristaltic pump |
| 910 | Peristaltic pump |
| 912 | Peristaltic pump |
| 920 | Ambient air source |
| 922 | Saturated acetone source |
| 924 | Saturated ethanol source |
| 926 | Pure carbon dioxide source |
| 1233 | Front half of device casing - 1st part |
| 1234 | Front half of device casing - 2nd part |
| 1235 | Back half of device casing - 1st part |
| 1236 | Back half of device casing - 2nd part |
| 1237 | Middle of device casing |
| 1238 | Circular-shaped bus board |
| 1241 | Flow Director |
| 1243 | Cable connector |
| 1300 | Sensor chamber assembly |
| 1310 | Control board. Note that there can be many control boards in a system as shown at 1310A, 1310B, and 1310C. |
| 1320 | Connector |
| 1330 | Sensor board |
| 1330A | Sensor board (7.8 mm tall × 8.1 mm diameter sensor) |
| 1330B | Sensor board (5 × 7 × 1.5 mm surface mount sensor) |
| 1330C | Sensor board (7.8 mm tall × 8.1 mm diameter sensor) |
| 1340 | Slider-clip |
| 1350 | Rail system/chamber frame |
| 2302 | Supply voltage signal and/or supply (Vdd) |
| 2304 | Global communication bus (Global COM) |
| 2306 | Connection between system computer and external monitor (COM-Power) |
| 2325 | Power source from standard wall outlet |
| 2327 | AC/DC Power converter |
| 2329 | Step down power regulator |
| 2331 | System computer processor |
| 2333 | Display screen mounted in the system computer unit |
| 2335 | External communication interface (Bluetooth, Ethernet, Wi-Fi, etc) |
| 2337 | External monitor |
| 2339 | Electrical interconnect assembly between control boards and system computer |
| 2345 | Sensor, of which there can be a plurality: 2345A, 2345B and 2345C. |
| 2347 | Electro-static discharge (ESD) protection |
| 2349 | External keyboard |
| 2404 | Analog voltage supply (Vdda) |
| 2406 | Internal communication bus (COM) |
| 2410 | Sensor output voltage signal (V-sense) |
| 2412 | Heater voltage signal (VH) |
| 2414 | Heather current signal (Current Sense) |
| 2416 | Select signal (SEL) |
| 2425 | System connector |
| 2427 | Voltage regulator |
| 2429 | Communication level shifter |
| 2431 | Power amplifier that generates a header voltage signal (Vh) |
| 2433 | Fixed resistor |
| 2435 | Board to board connector between control board and sensor board |
| 2437 | Externally controlled variable resistor (ECVR) |
| 2439 | Multiplexer with 8 input channels and 1 output channel |
| 2441 | Multiplexer with 2 input channels and 1 output channel |
| 2443 | Heating element (heater) |
| 2445 | Metal oxide semiconductor (MOS) |
| 2447 | Sensor package |
| 2449 | Temperature sensor |
| 2451 | A voltage reference |
| 2453 | Output amplifier |
| 2455 | Analog to digital converter (ADC) |
| 2457 | Control board processor |
| 2480 | Control board configured for voltage division sensor measurement |
| 2481 | Sensor board configured for a four-wire analog sensor |
| 2525 | Instrumentation amplifier |
| 2527 | Wheatstone bridge with fixed resistors and one sensor as a variable resistor |
| 2580 | Control board for Wheatstone bridge sensor measurement based on 2527 |
| 2625 | Multiplexer with eight pairs of input channels and one pair of output channels |
| 2680 | Wheatstone bridge circuit with Wheatstone integrity protection |
| 2825 | Wheatstone bridge with three controlled variable resistors and one sensor |
| 2880 | Control board for Wheatstone bridge sensor measurement based on 2825 |
| 2945 | Hot wire metal oxide semiconductor |
| 2947 | Two-wire metal oxide semiconductor sensor |
| 2955 | Metal oxide semiconductor (MOS) sensing element |
| 2957 | Digital metal oxide semiconductor sensor |
| 2980 | Control board based on 2880 for alternate sensor board |
| 2981 | Sensor board configured for a two-wire metal oxide semiconductor sensor |

-continued

| Number | Component or Feature |
|---|---|
| 2990 | Control board for digital two-wire sensor |
| 2991 | Sensor board configured for digital two-wire sensor |
| 3002 | RC (resistor-capacitor) sense signal |
| 3025 | 555 timer |
| 3031 | Counter |
| 3033 | Fixed capacitor for RC circuit |
| 3080 | RC circuit-based control board |
| 3081 | Sensor board with 4-wire MOS sensor and RC circuit |
| 3100 | System controller to control board data flow |
| 3105 | System controller sends commands and receives requested data |
| 3110 | Is system controller sending command or request? |
| 3115 | Add command to queue |
| 3120 | Store data in buffer |
| 3125 | End |
| 3130 | Pull requested data from local memory |
| 3135 | Return data over global communication bus |
| 3200 | Main process flow for control board firmware |
| 3205 | Start |
| 3210 | Initialize peripherals |
| 3215 | Is command pending? |
| 3220 | Switch to local communication bus |
| 3225 | Process command |
| 3230 | Store results in register |
| 3235 | Switch to global communication bus (Item 2406) |
| 3300 | System controller main software flow |
| 3305 | Start |
| 3310 | Load configuration |
| 3315 | Read list of control boards |
| 3320 | Initialize pointer to first board |
| 3325 | Open graphical user interface window on monitor |
| 3330 | Wait for user input |
| 3335 | Read board address |
| 3340 | Does board respond? |
| 3345 | Send settings over global communication bus (Item 2406) |
| 3350 | End of list? |
| 3355 | Increment pointer |
| 3360 | Go to "run Test" flow (Item 3400) |
| 3400 | Run test flow on system controller |
| 3405 | Start testing flow |
| 3410 | Set testing flag |
| 3415 | Check testing flag |
| 3420 | Wait for board 0 to become available |
| 3425 | Send sample sensors command to each board |
| 3430 | Read sensor results from each board |
| 3435 | Append results to local memory |
| 3440 | Write data from local memory to *.csv file |
| 3445 | Return to step 3330 |
| 3500 | Communication sequence between system controller and control boards |
| 3505 | Communication time to send command |
| 3510 | Time for control board to process command |
| 3515 | Communication time to send request |
| 3520 | Time for control board to process request |
| 3525 | Communication time to return data |
| 3600 | Data processing overview |
| 3610 | Control board firmware |
| 3615 | Test initiated from user interface |
| 3620 | Sample sensors of each control board |
| 3630 | Read sensor results of each control board |
| 3655 | For each enabled channel |
| 3660 | Sample sensor using ADC |
| 3665 | Calculate sensor voltage from ADC |
| 3670 | Calculate sensor resistance |
| 3675 | Store result in local memory |
| 3680 | Send requested channel result from local memory |
| 3705 | Get ADC value from step 3660 |
| 3710 | Return to step 3675 |
| 3805 | Ambient air test result file generated from 3650 |
| 3810 | Calculate Ro for each sensor |
| 3815 | Compound test result file generated from 3650 |
| 3820 | Calculate Rs for each sensor |
| 3825 | Determine sample number where falling edge of flow meter occurs |
| 3830 | Average previous n samples before flow meter falling edge |
| 3835 | For each sensor, calculate resistance ratio |
| 3900 | Infrared absorption spectroscopy gas sensor system |
| 3905 | Emitter board |
| 3910 | Detection board |
| 3915 | LED array |
| 3920 | LED |
| 3925 | Photodiode |
| 3930 | Trans-Impedance Amplifier (TIA) |
| 3935 | Programmable Gain Amplifier (PGA) |
| 4000 | Logarithmic amplifier |
| 4010 | Logarithmic converter |
| 4015 | Rescale circuit |
| 4020 | Bias generator |
| 4025 | Operational amplifier |
| 4030 | Diode chain |
| 4035 | Feedback resistor |
| 4040 | Feedback resistor |
| 4045 | Analog input signal from sensor |
| 4050 | Analog output signal that is the logarithm of the input signal |
| 4100 | Logarithmic output circuit |
| 4105 | Logarithmic control board |
| 4200 | Differential logarithmic output circuit |
| 4205 | Differential logarithmic control board |

DETAILED DESCRIPTION

The ensuing description provides preferred exemplary embodiment(s) only, and is not intended to limit the scope, applicability, or configuration of the disclosure. Rather, the ensuing description of the preferred exemplary embodiment(s) will provide those skilled in the art with an enabling description for implementing a preferred exemplary embodiment.

It should be understood that various changes could be made in the function and arrangement of elements without departing from the spirit and scope as set forth in the appended claims. Preferred embodiments of the present invention are illustrated in the Figures, with like numerals being used to refer to like and corresponding parts of the various drawings. Specific details are given in the following description to provide a thorough understanding of the embodiments. However, it will be understood by one of ordinary skill in the art that the embodiments may be practiced without these specific details.

In one embodiment, the present invention is an electronic nose system for determining a human health status that can comprise modules and/or methods for collecting and analyzing the existence and concentration of gaseous volatile organic compounds (VOCs) and other biomarkers found in air samples from a human. The systems and/or methods can comprise the following elements:

(a) A module for receiving the air sample or samples;
(b) A flowmeter;
(c) A temperature sensor;
(d) A humidity sensor;
(e) An array of electronic sensors that produce electrical information responsive to the chemical composition of the breath; and
(f) A discriminator that detects health in response to the electrical information from the sensors.

The array of electronic sensors could comprise one or more of the following sensing technologies:

(a) Metal oxide semiconductor (MOS) sensors that detect the concentration of various vapors by measuring a change in a property of the metal oxide (such as resistance, voltage, capacitance, and/or current) due to a reaction and/or adsorption of the vapors;

(b) Electrochemical sensors, such as electrochemical gas sensors that produce an electrical signal in response to a chemical property of the compound being measured, one example of which is a fuel cell;

(c) Infrared sensors that measure the absorption of infrared light by specific chemical compounds in the sample at specific frequencies/wavelengths based on the fact that each compound has its own absorption spectrum; and (d) Pellistor sensors that consist of small "pellets" of catalyst loaded ceramic whose resistance changes in the presence of a gas.

More specifically:

(a) The module for receiving the exhaled human breath could be a device that a human subject breathes into, such as a breathalyzer.

(b) If MOS sensors are used, the array of these MOS sensors could comprise sensors that differ in reactivity to various gases as a result of the use of different doping and catalyst materials.

(c) The array of MOS sensors could comprise multiple sensors that each have the same chemical composition but are operated at different temperatures by setting their heater voltages at different levels.

(d) The MOS sensors could comprise planar MOS sensors that have a separate wire pair for the heaters and a separate wire pair for measuring resistance, hot wire MOS sensors that have only two wires that both generate heat and measure resistance simultaneously, and or any other MOS sensor configuration.

(e) Filters could be used to selectively expose one or more of the sensors to some chemicals while preventing the exposure of the sensors to other chemicals in the breath.

(f) Catalysts could be used to convert some compounds in the breath to other compounds to facilitate selectivity and sensitivity of the instrument.

(g) The discriminator could be responsive to any characteristics of the output of any sensor or combination of sensors, including but not limited to differences or ratios in sensor output, differences or ratios of sensor output as a function of time, and/or differences or ratios of sensor output as a function of any other sensor output. For example, the discriminator could be responsive to the rate of change of a sensor when another sensor is also responding such as the rate of change of an MOS sensor when there is a sudden or step change in flow rate, as indicated by a flow meter.

(h) The output of any sensor could be a linear function of some chemical or physical characteristic of the breath being analyzed. It could be an exponential, logarithmic, power-law or other mathematically defined function of some chemical or physical property of the breath being analyzed.

Additionally, the systems and or methods can comprise:

(a) A sensor chamber with multiple sensors that generate time-dependent electrical signals in response to the chemical composition of the air that flows through the chamber.

(b) The sensor chamber can also have valves (including check valves or one-way valves) that shut the sensor chamber from off from gas flow so that the sensors in the sensor chamber can measure the composition of a static air sample.

(c) Elements for controlling the environment in the sensor chamber and other parts of the system/method. Such elements can comprise, a heater, a humidifier, a dehumidifier, a fan, and/or associated control components, and other elements for monitoring and modifying the environment of the gas in the sensor chamber.

(d) Elements for performing a vapor-phase separation of the biomarkers in the breath prior to sensing them. This separation could be performed using principles, systems, and methods related to gas chromatography including, but no limited to the absorption/adsorption and subsequent desorption and detection of gaseous molecules from exhaled human breath. For example, the absorption/adsorption can be accomplished using materials such as activated carbon, or one of many other materials for the absorption and absorption of carbon dioxide and volatile organic compounds. As another example, the adsorption of volatile organic compounds can be accomplished using Tenax TA. The desorption can be accomplished by gradual heating of the absorbent/adsorbent, or a gradual heating of the carrier gas in gas chromatography column, which will release different compounds at different temperatures to provide a separation of the compounds that have been absorbed/adsorbed. Such processes can comprise the use of an inert carrier gas such as nitrogen, helium, hydrogen, or argon.

(e) One or more pumps, fans, valves, and controllers to manage the flow of gases at various times during the breath testing process, for purposes such as purging, environmental control, separation (adsorption/desorption), calibration and/or compensation, and the use of modules in the system (such as the sensor chamber) to perform different functions (such as ambient air measurement, breath gas measurement, and absorption/desorption module output measurement) at different times during the testing process.

The configuration of the mechanical aspects of the systems and methods can be optimized to:

(a) Minimize sensor chamber volume while maximizing the number of sensors that access and exhaled breath in the sensor chamber;

(b) Use a modular approach in which it is easy to adapt the mechanical components to correctly position a variety of different sensor packages including the ability to accommodate different sensor package shapes, sizes, and heights;

(c) Be easily reconfigurable by replacing sensor boards that have one type of sensor with sensor boards that have a different type of sensor;

(d) Be as simple, reliable, and low cost as possible, and (e) Be adaptable to systems requiring from as few as 1-2 sensors to up to 36 or more sensor locations, each of which could house multiple sensors, providing the capability of having more than 100 sensors. For reference, humans have about 350 functioning olfactory receptor types, dogs have about 850, and mice have between 1100 and 1200 types.

The configuration of the electronics can comprise:

(a) Sensor boards that are specific to particular sensor packages and pinouts;

(b) Control boards that are generic, and electronically, configurable so that they can be used with a variety of sensor boards;

(c) Standard connectors that connect analog signals between the sensor boards and control boards;

(d) A central processor board that uses multiplexers to read all of the data channels from all of the control units to manage the data from the control boards, configure the control boards, connect with an internal status display (which can display information using a graphical user interface based on HTML and other web browser protocols and interactions);

(e) Standard connectors and cables to connect control boards to a central processor board;

(f) Communications to external devices and the internet for data transfer, further analysis, and external system control; and (g) The provision and distribution of electrical power for the entire system.

The systems and methods can comprise elements and processes for characterization, calibration, and compensation of sensor outputs. This can comprise:

(a) Characterization of the relationship between sensor output and gas composition, gas temperature, and/or gas flow rate. Examples of gas composition can include the concentration of gases such as carbon dioxide, nitric oxide, volatile organic compounds (VOCs), and humidity. Such characterization of sensor output is often provided by the sensor manufacturer. It can also be performed by the instrument manufacturer or in the field, if standard gas mixtures at standard flow rates are available. Such characterization of sensor output may be expressed in the form of a mathematical function or functions and/or graphical curves on data sheets provided by the sensor manufacturer. Such characterization can be used as part of the design process for the electronic nose. The data sheets can also identify limits of the range in which the sensor can be reliably operated and limits in the range in which the sensor response is linear, and/or given mathematical functions can be applied.

(b) Calibration of the sensor to generate a standard output in response to a standard gas composition at a standard temperature and flow rate. This can be used to: (1) verify that a specific sensor is operating in a normal range; (2) to adjust the output of the sensor to be consistent with other sensors of the same type produced by the same manufacturer; and/or (3) recalibrate the output of the sensor as it ages. Calibration of this type can be performed by the manufacturer of the system using the sensors. It can be performed in the field if standards are available. It could also be performed by the sensor manufacturer if there is a way to send the sensors to the manufacturer for calibration. The time interval between calibrations can be established based on tests that characterize the relationship between sensor aging and sensor output.

(c) Compensation of the sensors to provide the same output based on the conditions of the ambient air (such as atmospheric pressure, temperature, and relative humidity) at the time when tests are being run. Compensation is typically performed in the field.

Calibration and compensation can be accomplished using analog electronic devices such as potentiometers, using digital calibration and compensation on the device, or by calibrating and compensating after data has been collected. Characterization, calibration, and compensation can be performed manually, and/or automatically and dynamically. Characterization, calibration, and compensation can be multi-dimensional and can include the use of complex multiple-input-multiple-output (MIMO) formulas using neural networks, machine learning, artificial intelligence, and related technologies. Characterization, calibration, and compensation can further comprise allowing the sensors to stabilize over a long time (such as 4, 6, 8, 12, 24, or 48 hours) before the characterization, calibration, and/or compensation is performed.

Characterization, calibration, and compensation can further comprise grouping a plurality of sensors into sensing arrays of the same type, the plurality of sensors positioned to form a virtual sensor wherein each of the plurality of sensors is in communication with the input/output interface of a processor to generate aggregated sensing outputs for each array that characterize the virtual sensor. The aggregated sensor output could be a weighted or unweighted average of the plurality of the sensor outputs, it could be the median sensor output, or it could be any other combination of the plurality of the sensor outputs capable of being understood by anyone skilled in the art. For example, the highest and lowest sensor outputs could be removed, and the average of the remaining sensor outputs could be taken. As another example, the aggregated sensor output could be the midpoint of the range of sensor outputs.

The systems or methods of the disclosed invention or inventions can comprise the use of processes, algorithms, and/or algorithmic processors that use the data from the electronic sensors to assist in the screening and diagnosis of human health conditions or for determining human performance Such processes, algorithms, and/or algorithmic processors can be used to do the following:

(a) Data preparation, a category of methods that includes normalization, smoothing, baseline and outlier removal, interpolation, and visualization using any methods capable of being understood by anyone skilled in the art. Examples can include kernel regularization for data smoothing, the Hiroshi Akima method of interpolation of missing or irregularly sampled data, deconvolution with the instrument response function, and the RANSAC algorithm, published by Martin Fischler and Robert Boles of the Stanford Research Institute in 1980, which can be used for denoising of data by outlier removal.

(b) Exploratory data analysis, a category of methods that includes dimension reduction and clustering and other similar methods capable of being understood by anyone skilled in the art. Examples can include principal component analysis (PCA), K-means clustering, and image pattern matching methods such as the SIFT (scale invariant feature transform) algorithm described in U.S. Pat. No. 6,711,293.

(c) Machine learning, a category of methods that includes classification and deep learning using neural networks, using methods capable of being understood by anyone skilled in the art. Classification methods typically use training data to identify distinctions between data sets and are therefore considered to be "supervised", e.g., the K-nearest neighbor classifier, support vector machines, or random forests. They can also be "semi-supervised" by using a combination of classification and clustering, e.g., transductive support vector machines (TSVMs) or Bayesian-Gaussian mixtures. Deep learning methods can include recurrent and/or convolutional neural networks (RCNN) and acoustic fingerprints used speech and music recognition, such as Shazam.

The output of the system and method could be a health status score. For example, it could be a risk factor associated with a particular disease or health condition, such as an indication of the risk of having liver disease, lung cancer, diabetes, high blood alcohol, or any other health condition capable of being understood by anyone skilled in the art.

This health status score could be used to control the performance of a medical procedure, such as a recommendation that addition tests or biopsies be performed, or that some more complex surgical procedure be performed.

Referring now to the drawings, FIG. 1 illustrates one embodiment of a system and/or method for health analysis from exhaled human breath. In the embodiment shown in FIG. 1, exhaled breath is received from a human subject 98 in a module as shown at 100. This breath receiving module 100 can comprise elements to isolate the breath, such as a filter or a one-way valve, that help prevent pathogens or undesired items from getting to the human subject. After the breath receiving module 100, the exhaled breath can be converted to electrical signals using an array of metal oxide semiconductor sensors, as shown at 200. The information in these electrical signals can then compared to "patterns" of these signals from other human subjects, as shown at 300, to determine health status and/or performance as shown at 400. The system and method shown in FIG. 1 allow the health status analysis to be performed directly at the time of care and the point of care and for the results to be provided while the human subject is at the point of care. Examples of what is meant by "determine health status and/or performance" can include:

(a) Performance measurements such as whether a healthy individual is under the influence of alcohol or drugs or has a temporary impairment due to something such as fatigue;

(b) Performance measurement such as whether a person is maintaining a certain diet regimen;

(c) Health screening for diseases such as infection by a pathogen, diabetes, COPD, lung cancer, liver disease; and/or (d) Diagnosis for similar conditions to make a definitive determination of a medical condition that might need treatment.

Figure 2:
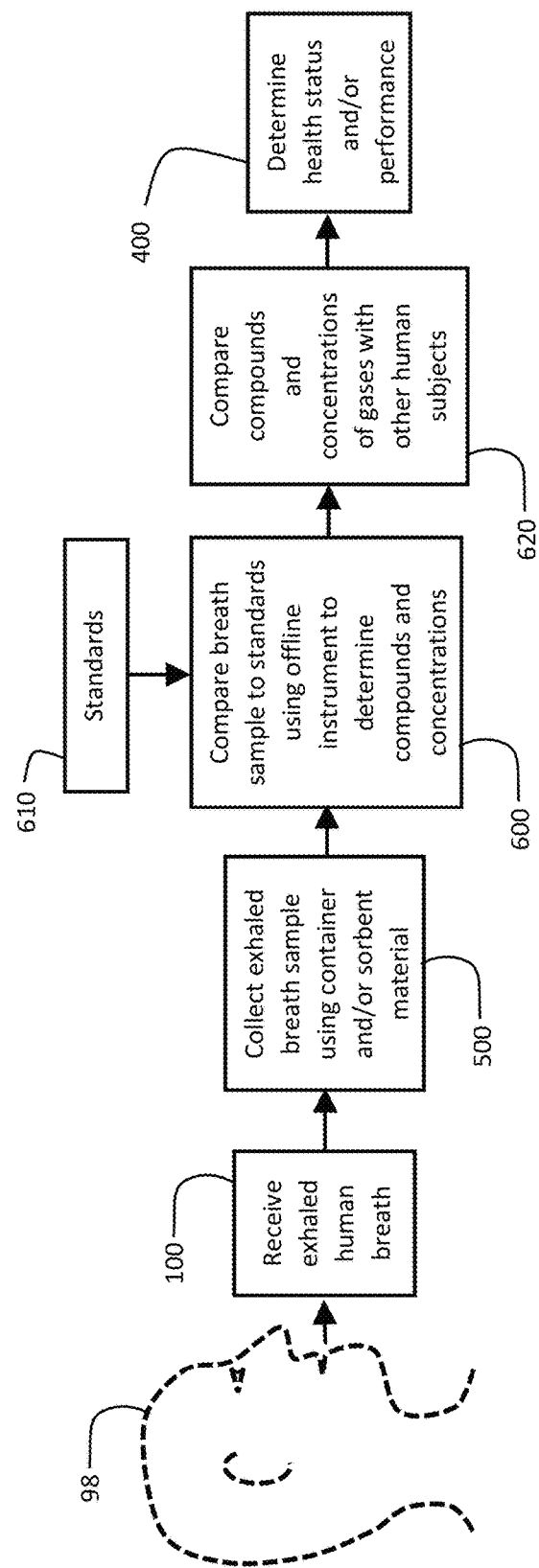
FIG. 2 shows a system and/or method for exhaled breath analysis in which breath compounds are stored and analyzed offline.

FIG. 2 illustrates another embodiment of a system or method for health analysis from exhaled human breath. Like the embodiment shown in FIG. 1, the embodiment shown in FIG. 2 also starts with receiving human breath 100 from a human subject 98. The received human breath 100 is then collected into a container and/or sorbent material, as shown at 500. This container of the human breath is then analyzed offline as shown at 600. This offline analysis typically comprises a comparison of the concentrations of various gases in the breath to a standard, shown at 610. These concentrations of the gases are then compared with similar information from other human subjects, as shown at 620 to determine health status or performance 400, the same end point as for the embodiment shown in FIG. 1. The disadvantage of the embodiment shown in FIG. 2 is that the offline analysis typically requires expensive equipment and therefore the results cannot be provided to human subject at the time of care and the point of care. Therefore, it is more desirable to use the system and/or method shown in FIG. 1 if this can be done accurately and effectively. It should be noted that embodiments of the inventions disclosed herein can comprise combinations of elements of the system and/or method shown and described with reference to FIG. 1 and the system and/or methods shown and described with reference to FIG. 2.

Figure 3A:
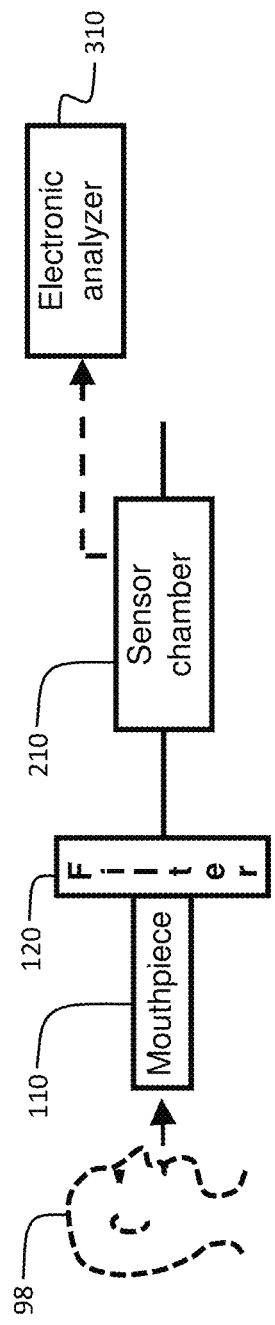
FIG. 3A shows schematic diagram of a simple device for direct breath analysis.

FIG. 3A shows schematic diagram of a simple device for direct health status analysis from human breath that is similar to the first steps that were shown in FIG. 1. Referring to FIG. 3A, the human subject 98 breathes into a mouthpiece 110 and filter 120 that serves the function of step 100 in FIG. 1. The exhaled breath then goes into a sensor chamber, shown at 210, which serves the function of step 200 in FIG. 1. Electronic signals from the sensor chamber are then fed to an electronic analyzer shown at 210, which can serve the same functions as steps 300 and 400 in FIG. 1.

Figure 3B:
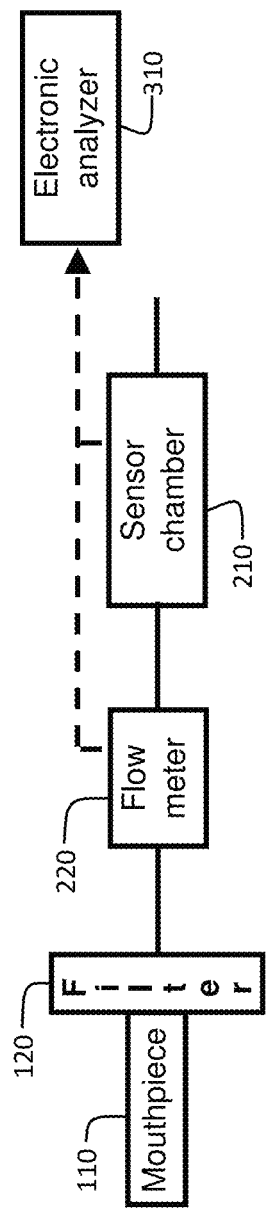
FIG. 3B shows the device of FIG. 3A in which a flow meter has been added between a mouthpiece/filter unit and a sensor chamber.

FIG. 3B shows the device of FIG. 3A in which a flow meter 220 has been added between the mouthpiece 110 and filter 120 unit and the sensor chamber 210. This flow meter 220 can be used to provide flow rate information to the electronic analyzer 310. The flow rate information can facilitate the process of determining human health status and/or performance by the electronic analyzer 310.

Figure 3C:
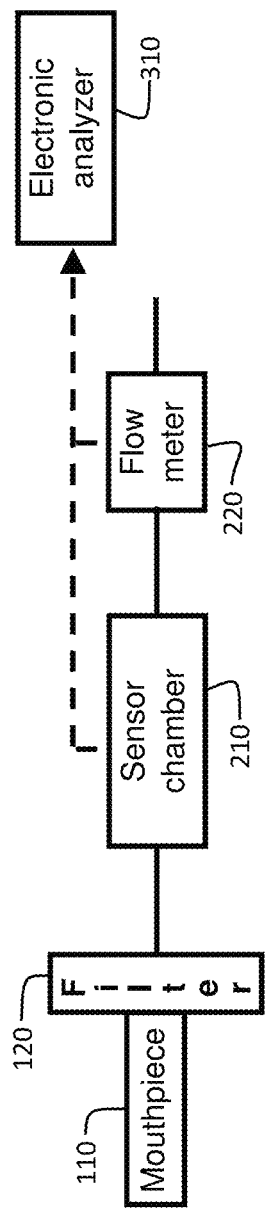
FIG. 3C shows the device of FIG. 3A in which a flow meter has been added downstream of the sensor chamber.

FIG. 3C shows the device of FIG. 3B in which the flow meter 220 has been moved downstream of the sensor chamber 210, with all other elements being the same as in FIG. 3B. One benefit of the configuration shown in FIG. 3C over the configuration shown in in FIG. 3B is that it is possible to get more of the air from the bottom of a human subject's breath if there are fewer components between the mouthpiece 110 and the sensor chamber 210.

Figure 3D:
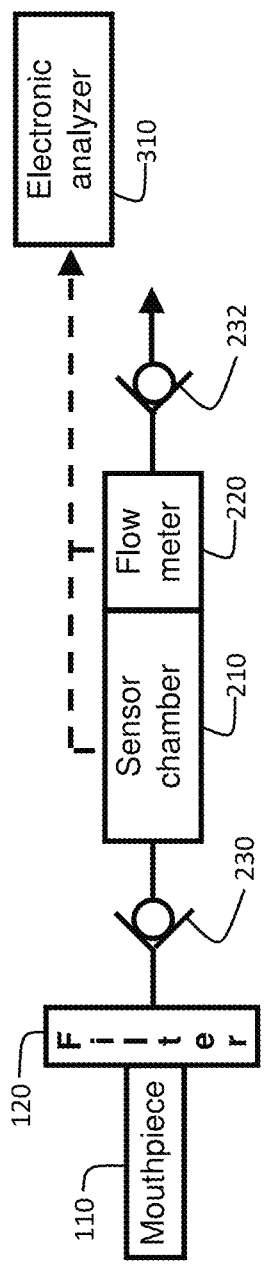
FIG. 3D shows the device of FIG. 3C that further comprises a check valve between the mouthpiece/filter and sensor chamber.

FIG. 3D shows the device of FIG. 3C that further comprises a first check valve 230 between the mouthpiece/filter (110/120) and sensor chamber 210 and a second check valve 232 downstream of the flow meter 220, at the output of breath from the device. In the embodiment shown in FIG. 3D. the flow meter 220 is also further integrated into the sensor chamber 210, which can reduce the amount of breath that is held in the system. This system uses an electronic analyzer 310 that is similar to the systems shown in FIG. 3A, FIG. 3B, and FIG. 3C. By using one or more check valves 230 and 232, the flow of breath through the system will occur in one direction only, from the human subject (98 in FIG. 3A) through the system (110, 120, 230, 210, 220, and 232) and out, as shown by the arrow to the right of the second check valve 232 in this diagram. This first check valve 230 prevents any back flow. The second check valve 232 creates a trapped volume of breath that can be analyzed in its quiescent mode, to provide additional sensor information that can be used to help diagnose health status or human performance. Thus, the system shown in FIG. 3D can be used for measuring sensor output along with flow rate when a person is breathing out, as well as the characteristics of the breath when it is still.

Figure 4A:
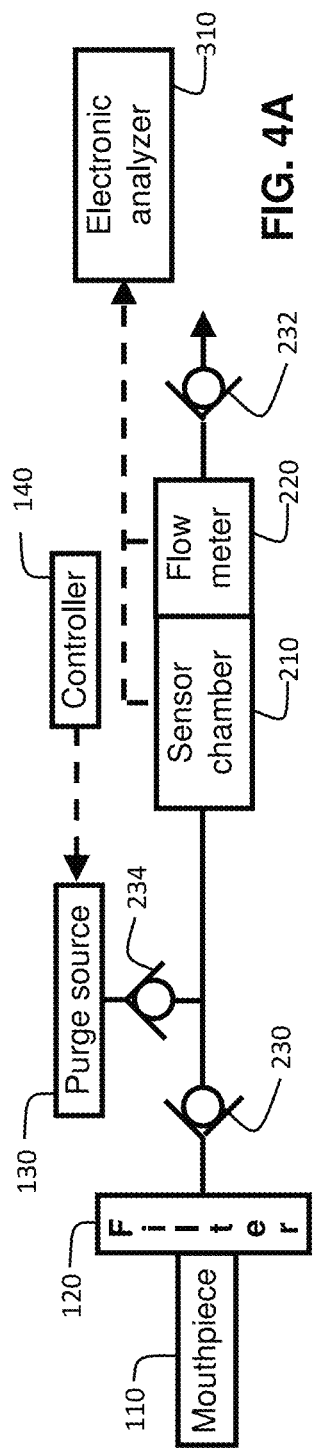
FIG. 4A shows the device of FIG. 3D that further comprises a source for a purge gas between the mouthpiece/filter and sensor chamber.

FIG. 4A shows the system of FIG. 3D that further comprises a source for a purge gas 130. This purge source 130 is in the flow path between the filter 120 and sensor chamber 210. As with the device shown in FIG. 3D, the device in FIG. 4A has a sensor chamber 210, a flow meter 220, and an electronic analyzer 310 that perform similar functions to the similarly-identified devices in FIG. 3D. The system in FIG. 3D has a controller 140 to control the flow of gas from the purge source 130. It also has a purge source check valve 234 to ensure unidirectional flow out of the purge source 130. The purge source shown in FIG. 4A and other embodiments can be any source of a standard gas capable of being understood by anyone skilled in the art. For example, the purge source could be dry compressed air, it could be bottled nitrogen, helium, or argon. It could be a heated gas to help evaporate any volatile compounds, such as organic compounds or water, that might have condensed anywhere in the system. The purge source could also simply be a fan or a pump that pumps ambient air through the system.

Figure 4B:
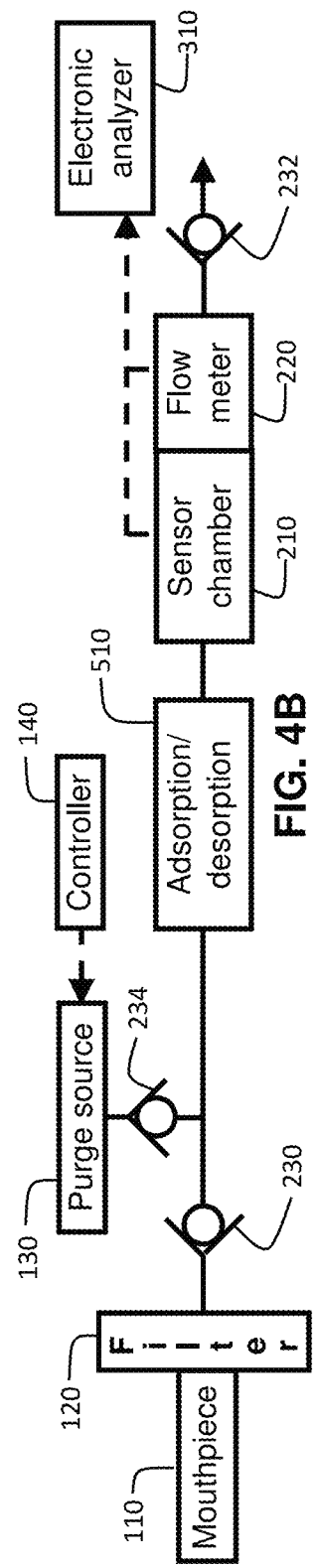
FIG. 4B shows the device of FIG. 4A further comprising an adsorption/desorption module located between the purge source and the sensor chamber.

FIG. 4B shows a system similar to the system of FIG. 4A that further comprises an adsorption and desorption module 510 located between the purge source 130 and the sensor chamber 210. All other items shown in FIG. 4B are similar to the similarly numbered items shown in FIG. 4A. The adsorption/desorption module 510 can comprise sorbent tubes containing a material that adsorbs gases, such as carbon dioxide, and/or volatile organic compounds (VOCs), such as acetone, when breath passes through the adsorption/desorption module 510 and then release those gases and/or VOCs when the sorbent tubes are heated. Heating of the sorbent tubes can comprise a sorbent tube electric heater that could be controlled by an electronic controller (not shown) and coupled to the electronic analyzer 310 to enable time dependent analysis of the gases that are released as a function of the sorbent temperature. These sorbent tubes can comprise adsorbent materials such as Tenax, carbon, molecular sieves, or any other adsorbent material capable of being understood by those skilled in the art. The adsorbent material may have chemical coatings that enhance or suppress the adsorption of specific gases or groups of gases, such as carbon dioxide and/or volatile organic compounds.

Figure 4C:
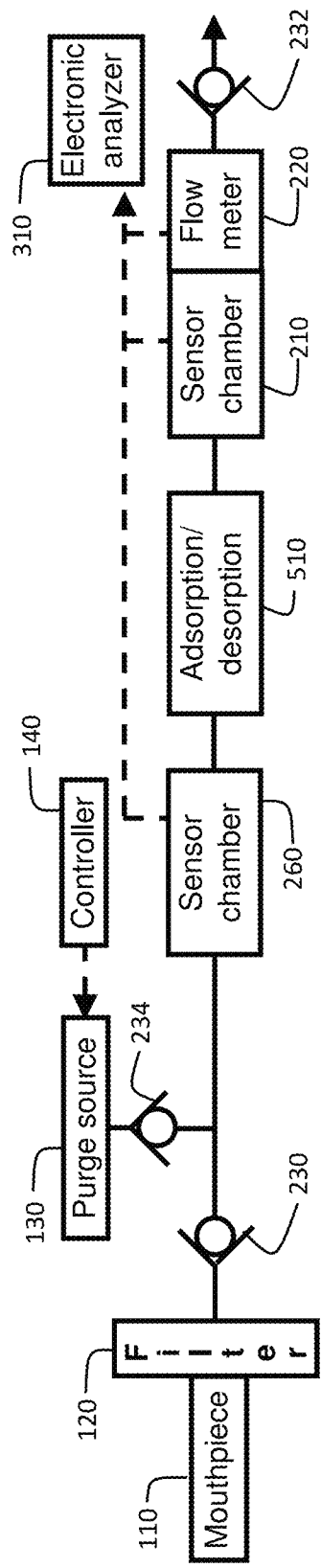
FIG. 4C shows the device of FIG. 4B with two sensor chambers, one upstream and one downstream of the adsorption/desorption module.

FIG. 4C shows the system of FIG. 4B with a second sensor chamber 260 in series with the first sensor chamber 210 and upstream of the adsorption/desorption module 510. All other items shown in FIG. 4C are similar to the similarly number items shown in FIG. 4B. The benefit of having a second sensor chamber 260 is that the gases in the breath can be analyzed both before and after adsorption and desorption to create both a time-varying breath sample and a separation analysis of the gases in the breath sample.

Figure 5A:
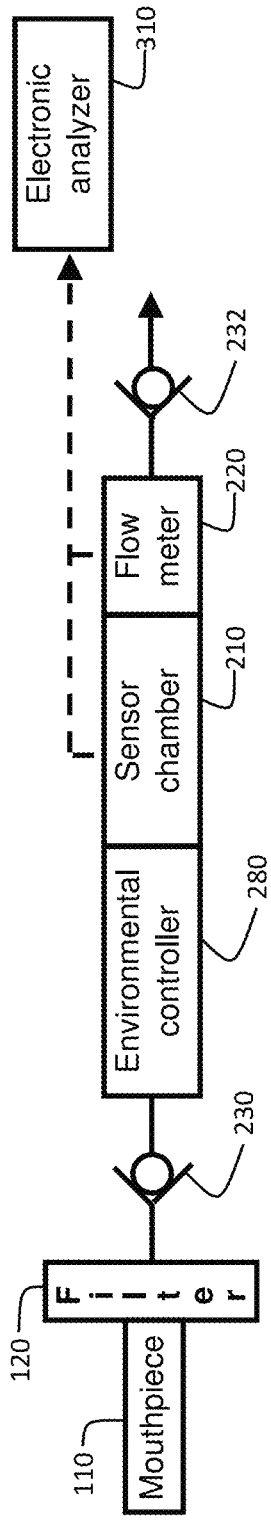
FIG. 5A shows the system of FIG. 3D further comprising an environmental controller upstream of the sensor chamber.

FIG. 5A shows the system of FIG. 3D with an environmental controller 280 added to control the environmental characteristics of the gases that go through the sensor chamber. All other items shown in FIG. 5A are similar to the similarly number items shown in FIG. 3D. Examples of environmental parameters that can be controlled using the environmental controller 280 can include temperature of the breath sample and humidity of the breath sample. This would allow the breath samples to be more uniform when going through the sensor chamber 210. It can also prevent condensation in the sensor chamber 210.

Figure 5B:
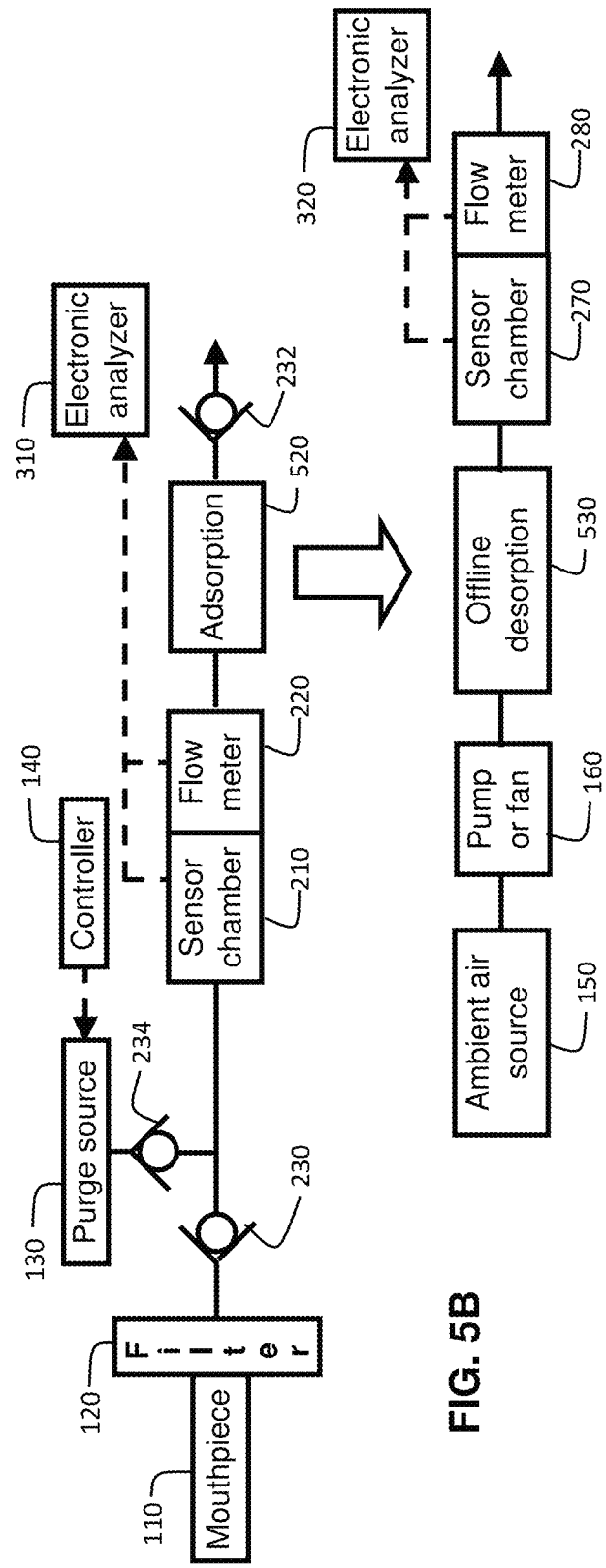
FIG. 5B shows the system of FIG. 4C where analysis of the adsorbed sample is performed offline.

FIG. 5B shows the system of FIG. 4C where analysis of the adsorbed sample is performed offline. In the system of FIG. 5B, the mouthpiece 110, filter 120, purge source, controller 140, check valve at the filter output 230, purge source check valve 234, and flow meter 220 are in the same configuration as the system shown in FIG. 4A. An adsorption module 520 has been placed downstream of the flow meter 220 and upstream of the check valve at the device outlet 232. This configuration allows for the collection of the same information the electronic analyzer 310 as for the system shown in FIG. 4A, while also allowing breath gases to be adsorbed in the same way as for the system shown in FIG. 4C. The adsorbed gases in the sorbent tubes can then be physically moved to an offline desorption module, shown at 530. The gases can be desorbed by using an ambient air source 150 that is propelled by a pump or fan 160 to drive the adsorbed gases out in the offline desorption module 530 as the sorbent material is heated. The adsorbed gases can then be measured in a second sensor chamber 270 and flow rates can be measured by a second flow meter, to be analyzed by a second electronic analyzer 320.

Figure 6A:
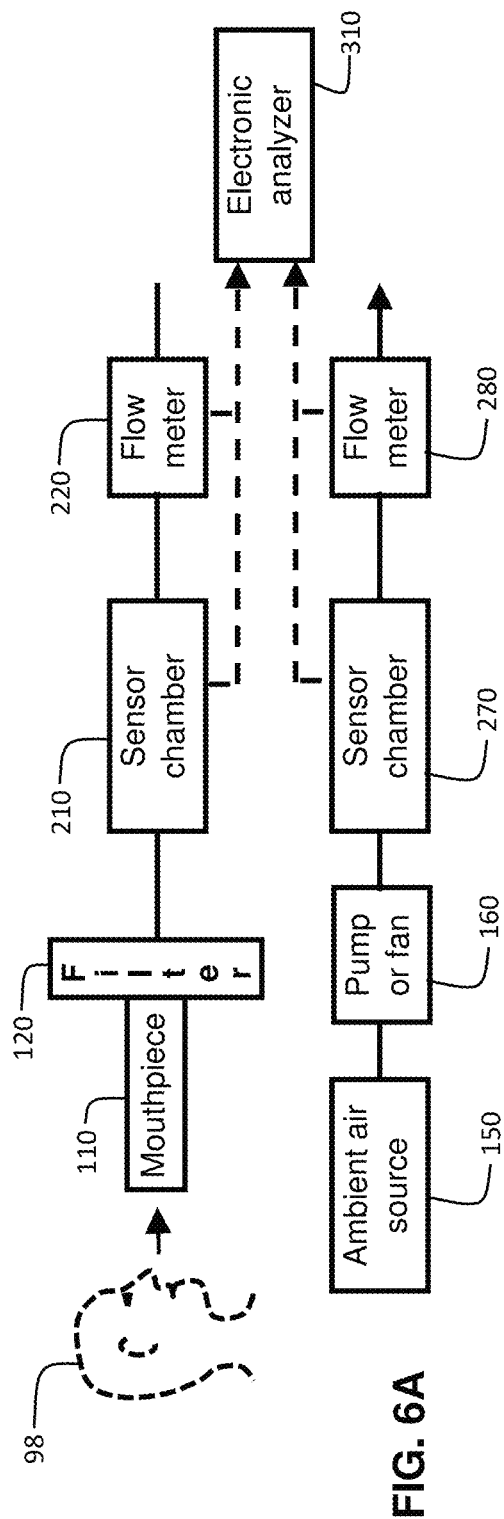
FIG. 6A shows the system of FIG. 3C combined with second sensor chamber and flow meter that simultaneously measures ambient air.

FIG. 6A shows the system of FIG. 3C combined with second sensor chamber and flow meter that simultaneously measures ambient air. In FIG. 6A, the human subject 98, mouthpiece 110, filter 120, sensor chamber 210, and flow meter 220 are the same and serve the same functions as the description of those items with reference to FIG. 3A and FIG. 3C. A parallel flow path for ambient air is provided by an ambient air source 150, pump or fan 160, through a second sensor chamber 270, and second flow meter 280. The benefit of the system shown in FIG. 6A is that parameters of the ambient air 150 and the breath from the human subject 98 can be analyzed simultaneously by the electronic analyzer 310 to identify a relationship between ambient air and the breath sample. This can be advantageous in dynamically producing the data that will be further discussed with reference to Appendix 2.

Figure 6B:
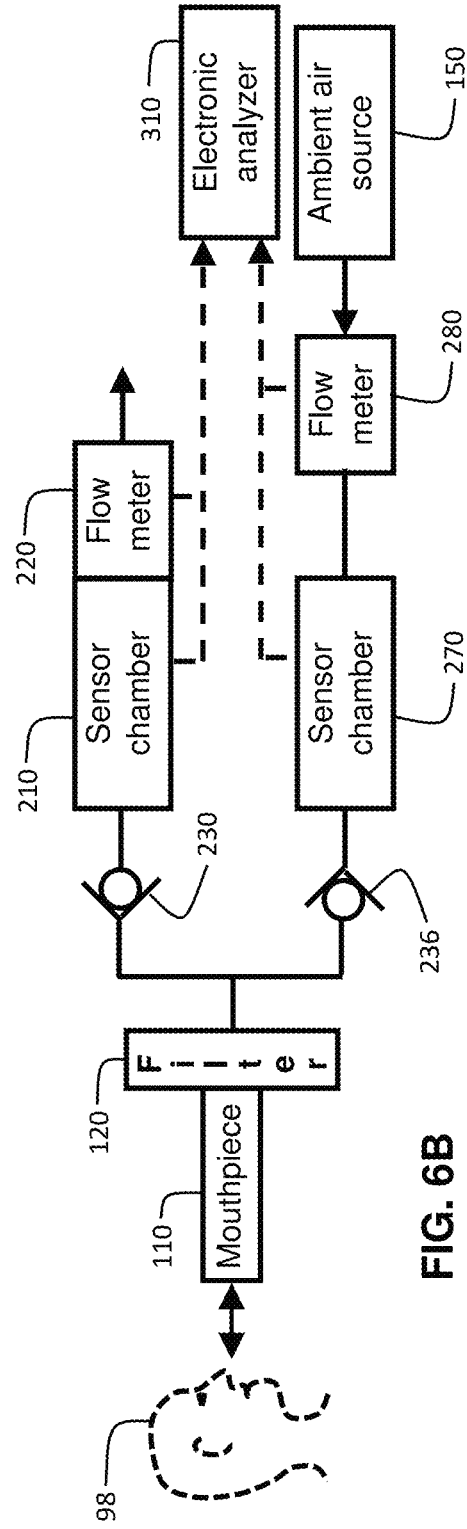
FIG. 6B shows a system in which inspired air is measured in one sensor chamber and flowmeter and expired breath is measured in another sensor chamber and flowmeter.

FIG. 6B shows a system in which expired breath is measured in the first sensor chamber 210 and first flowmeter 220, and inspired ambient air is measured in the second sensor chamber 270 and second flowmeter 280. In this case, the ambient air source 150 does not need a pump or fan, as was the case for the systems shown in FIG. 5B and FIG. 6A. The system does require a first check valve 230 and a second check valve 236 that serve to direct the inspired ambient air through the second sensor chamber 270 and the expired breath through the first sensor chamber 210. The first check valve 230 is in the same location and serves the same function as the similarly numbered check valve at the filter input 230 in FIG. 3D and other previously described drawings. The second check valve 236 is shown between the second sensor chamber 270 and the filter 120. The human subject 98, mouthpiece 110, filter 120, and electronic analyzer 310 serve similar functions to the similarly numbered items in previously described drawings.

Figure 7:
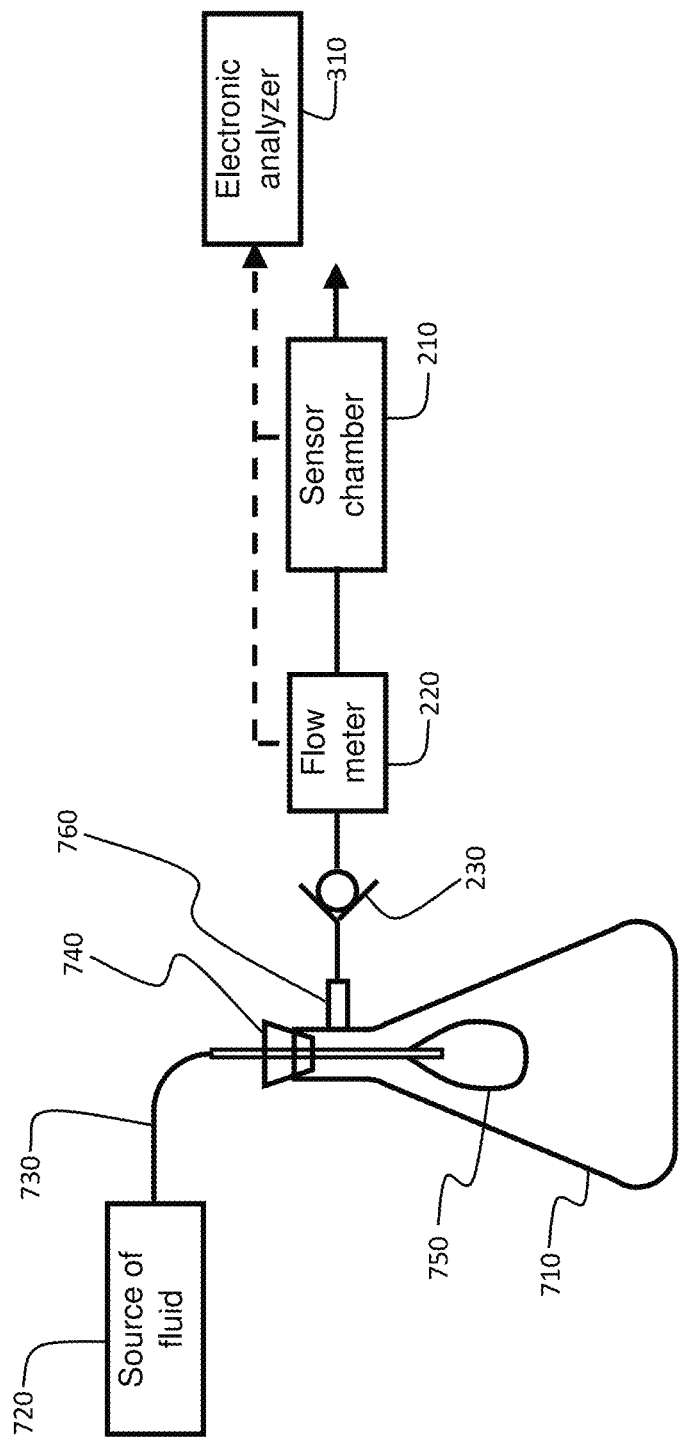
FIG. 7 shows a system for standardized testing of a gas in a flask where the concentration of the gas in the flask does not change as gas in the flask is moved through a flow meter.
Figure 8:
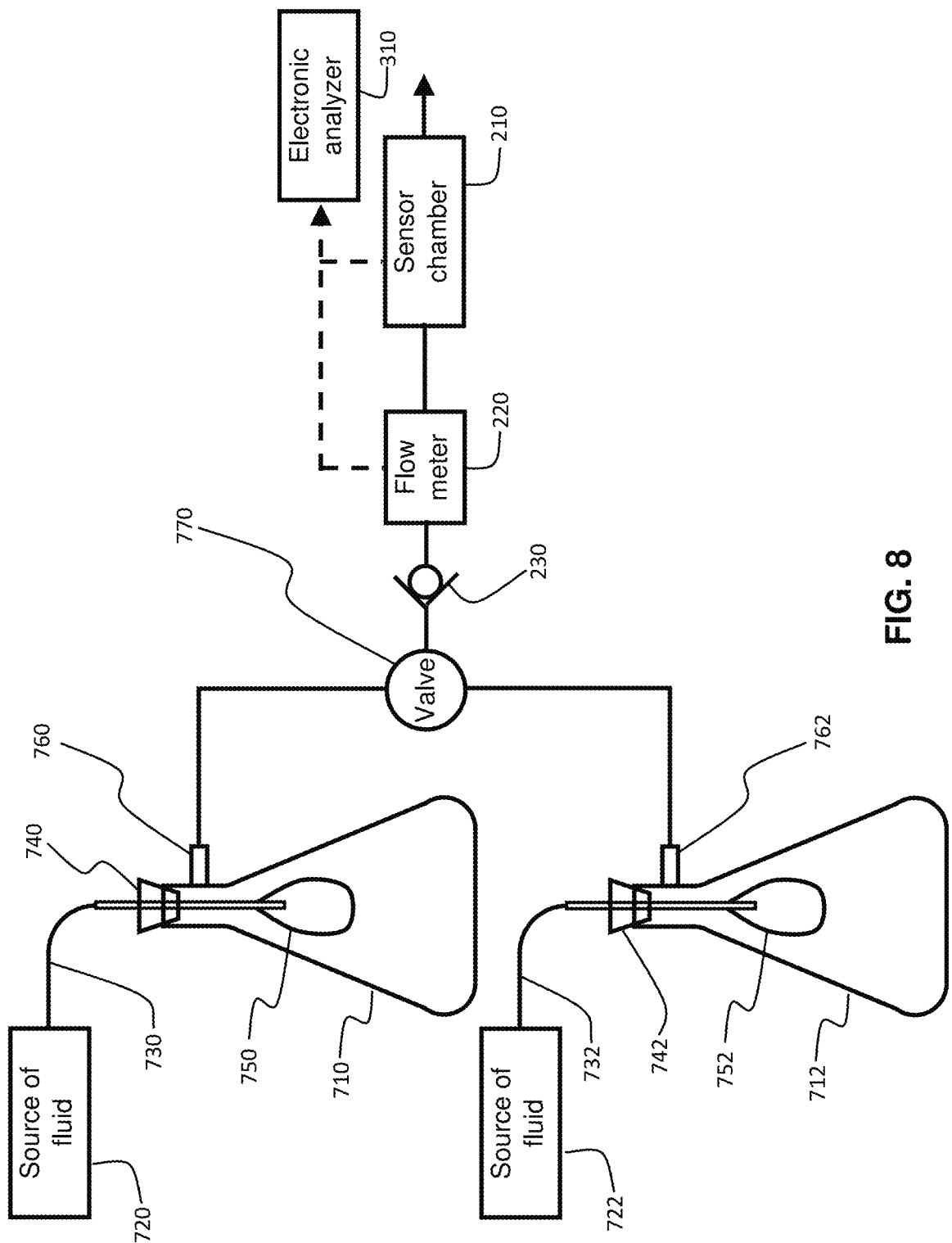
FIG. 8 shows a system similar to the system of FIG. 7 wherein multiple flasks can be used to mix gas samples.

FIG. 7 shows a system for standardized testing of a gas in a flask where the concentration of the gas in the flask does not change as gas in the flask is moved through a flow meter. Such as system is useful for developing and testing flow meters and sensor chambers for both calibration and system development. FIG. 8 shows a more complex test system that further comprises a second source of a test gas. Referring to FIG. 7 and FIG. 8, flow meter 220, sensor chamber 210, and electronic analyzer that were shown previously are configured in the same way as the system shown in FIG. 3B. There is also a check valve 230 upstream of the flow meter 220. Instead of receiving breath from a human subject, as was shown in the previous figures, the systems shown in FIG. 7 and FIG. 8 receive test gases. These test gases from one or more test gas chambers 710 and 720 through one or more test gas chamber outlets, 760 and 762. In the test system configuration shown in FIG. 8, the test gases can be mixed at a valve 770 that is downstream of the test gas chamber outlets 760 and 762. Test gases can be stored in the test gas chambers 710 and 712, and pushed out when the balloons, 750 and 752, are inflated by sources of fluid 720 and 722, that flow through tubing 730 and 732 that are inserted through stoppers 740 and 742 into the test gas chambers 710 and 712. Thus, the systems shown in FIG. 7 and FIG. 8 allow test gases to be pushed through the sensor chamber 210 in a controlled fashion without diluting the test gases.

Figure 9:
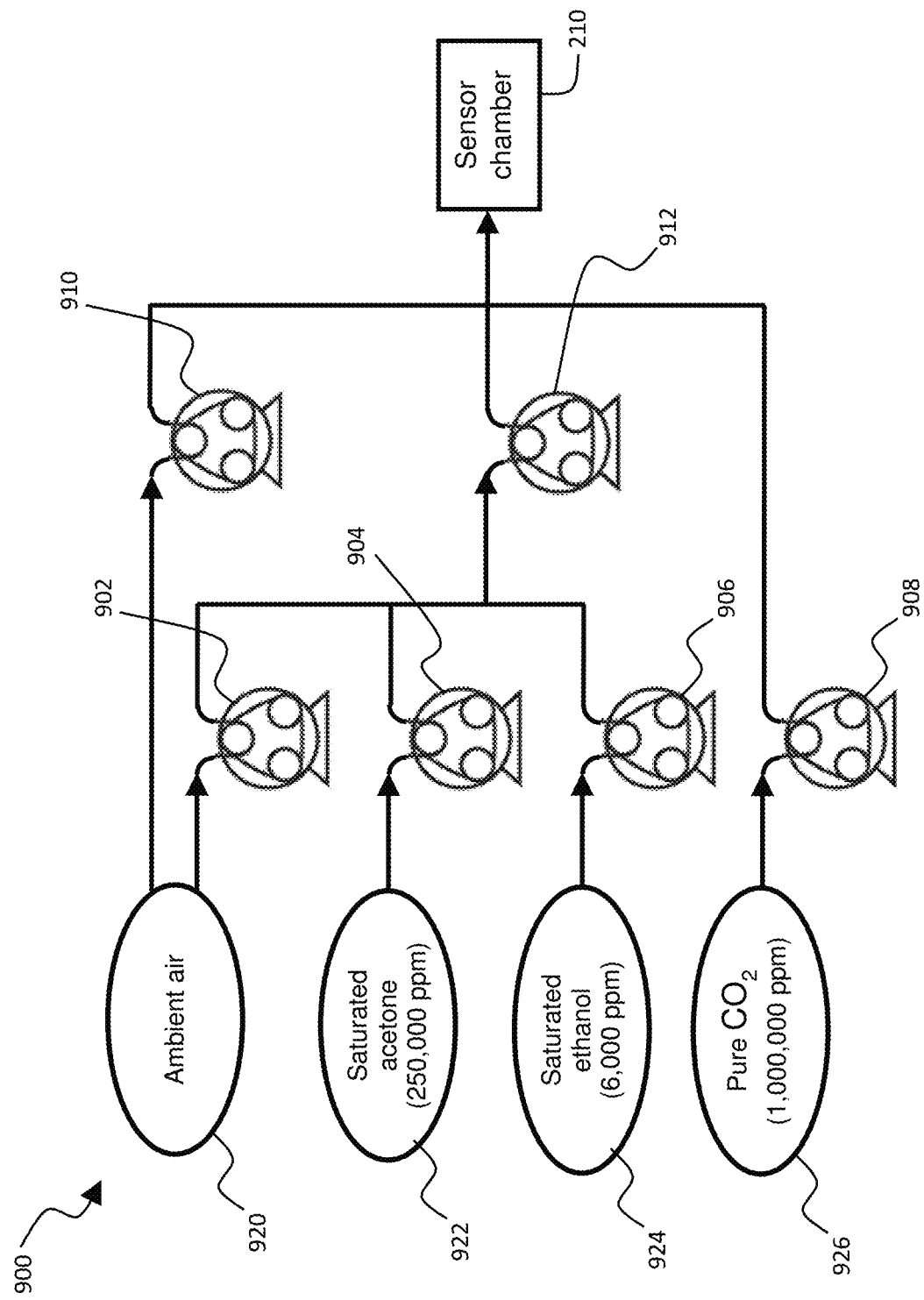
FIG. 9 shows an automated system for compounding multiple gaseous sources to produce "synthetic breath"

Referring to FIG. 7 and FIG. 8, there are multiple ways to create a specified concentration of a breath biomarker in a carrier gas (such as ambient air or nitrogen), such as:

(a) Creating a pure 100% concentration of a substance, such as CO2, by placing solid phase (dry ice) into a test gas chamber (710 in FIG. 7 and 710 or 712 in FIG. 8) and allowing the sublimating CO2 to push out all of the pre-existing gases in the test gas chamber;

(b) Placing more than enough of a volatile substance, such as acetone, into the test gas chamber so that the gas in the test gas chamber becomes saturated to the maximum concentration based on temperature, pressure, and Antione's equation, or analogous calculation based on vapor pressure for the substance at a specific temperature and the pressure of the resulting gas in the test gas chamber;

(c) Calculating the number of moles of a volatile substance, such as acetone, that must be added to the gas in the test gas chamber to achieve a desired concentration; and/or (d) Compounding specific volumes of the contents of multiple test gas chambers for the purpose of creating a dilution and/or a more complex mixture of substances to be used in testing of a breath testing device, as shown in FIG. 9.

FIG. 9, at 900 shows an automated system for compounding multiple gaseous sources to produce "synthetic breath". This gas compounding system 900 uses peristaltic pumps, 902, 904, 906, 908, 910, and 912 to mix different fluid sources (in this case gases) to create "breath" with a prescribed mix of compounds. In the example show in FIG. 9, the fluid sources are ambient air 920, saturated acetone in ambient air (at about 250,000 parts/million) shown at 920, saturated ethanol in ambient air (at about 6,000 parts/million) shown at 922, and pure carbon dioxide shown at 926. These fluid sources are connected by tubing to inlets of the peristaltic pumps. Outlets of the peristaltic pumps are then connected to each other, to mix different compounds and/or to a second stage of peristaltic pumps. The output of the resulting mixture is sent through the sensor chamber in a manner similar to the systems shown in FIG. 7 and FIG. 8. It is possible to create such systems in other ways, such as through the use of syringes, or other devices that allow for the accurate metering of specific volumes of gases to be mixed. The following is a table showing examples of how synthetic breath samples of various types could be produced using the system of FIG. 9.

| Output | Pump 902 | Pump 904 | Pump 906 | Pump 908 | Pump 910 | Pump 912 |
|---|---|---|---|---|---|---|
| 0.5 ppm acetone in ambient air (0.3-0.9 ppm is normal) | 499 | 1 | 0 | 0 | 999 | 1 |
| 200 ppm ethanol in air (equals 0.8% blood alcohol) | 29 | 0 | 1 | 0 | 1 | 1 |
| 2.0 ppm acetone in ambient air (1.8 ppm is diabetic) | 499 | 1 | 0 | 0 | 249 | 1 |
| 40,000 ppm (4%) CO2 in ambient air (normal breath) | 0 | 0 | 0 | 1 | 24 | 1 |
| 0.5 ppm acetone and 4% CO2 in ambient air (normal) | 499 | 1 | 0 | 40 | 959 | 1 |

It should be understood that an automated system of the type shown at 900 could contain as many sources and as many stages as needed and that the concentration of the source gases can be generated in any way described in this document or capable of being understood by anyone skilled in the art.

Figure 10:
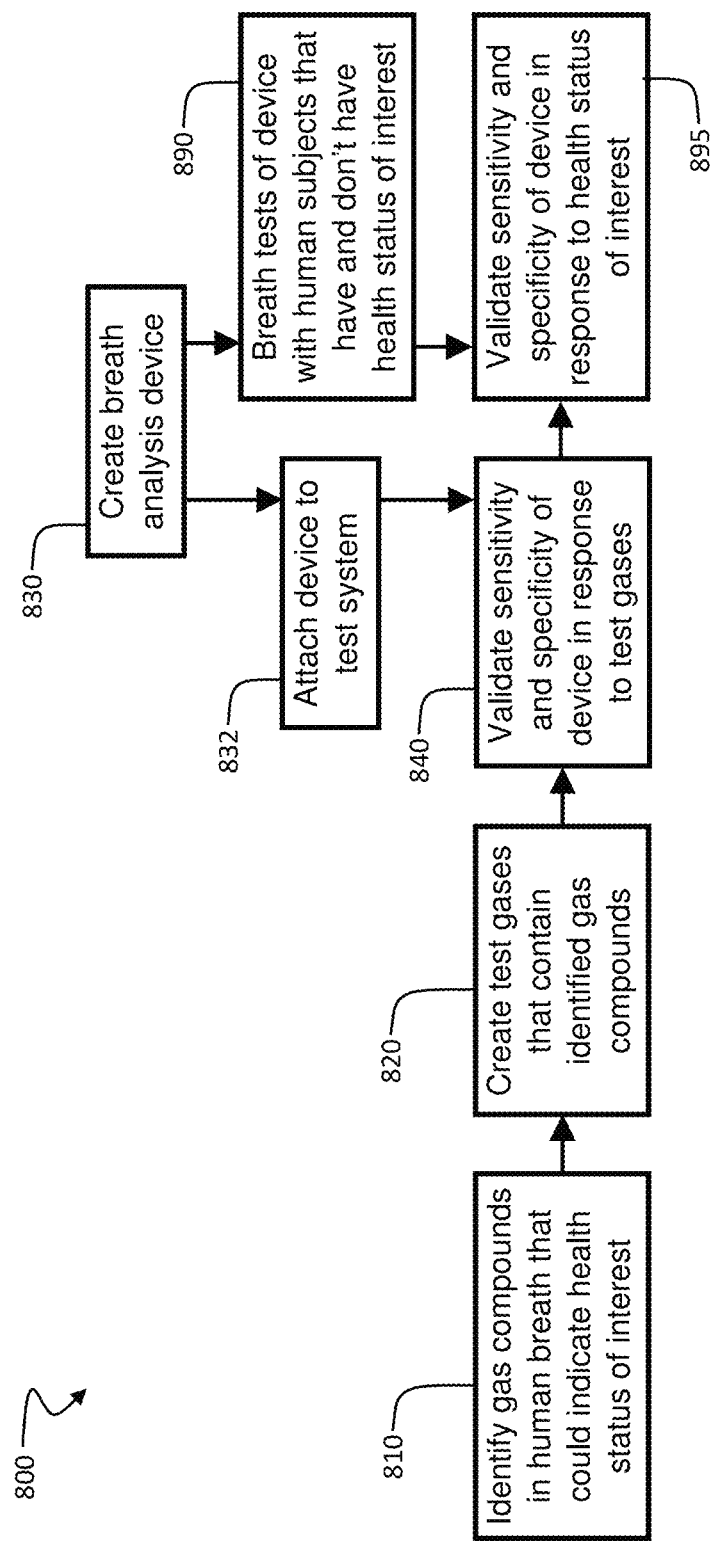
FIG. 10 gives a method for validating breath device response to a health status.

FIG. 10 shows an overview of a method for validating a breath analysis device, system, and/or method at 800. The device/system/method 800 starts by identifying the gas compounds in human breath that could indicate health status of interest, as shown at 810. For example, if the device/system/method is to be used for diagnosis of diabetes or detection of ketosis by someone on a ketogenic diet, one of the gas compounds of interest is likely to be acetone, a volatile organic compound (VOC).

The information about the gas compounds identified in step 810 can then be used to create test gases that contain the identified gas compounds, as shown at 820. One way to acquire such a test gas at a specific concentration is to purchase it. Another way is to mix a gas at one concentration with another gas, such as ambient air, at a specific mix ratio. Another way to create a test gas at a known concentration can be to evaporate a solid, such as dry ice (solid carbon dioxide) in a way that pushes out all other gases or in a vacuum. Yet another way to create a test gas is through a chemical reaction, which could be used to create compounds such as nitric oxide. The amount of the input chemicals could be controlled to produce a specific quantity of output gas. Yet another way that can be used for water, volatile organic compounds (VOCs) or any other volatile compound is to place enough liquid in an enclosed container containing air so that the air in the container becomes saturated with the gaseous form of that compound. The concentration can then be calculated by using Antoine's equations for air and that compound at the temperature of the mixture.

The test gases of interest created in step 820, can then be used to test the sensitivity and specificity of a device in response to the test gases, as shown at 840 and detailed further with reference to FIG. 10. In order to test the device sensitivity and specificity the device must be created, as shown at 830. The creation of a breath analysis device 830 can comprise any of the devices and systems shown and described anywhere in this document, or can comprise any elements of any of the embodiments described or anticipated in this document, including, but not limited to the embodiments shown and described with reference to FIG. 3A, FIG. 3B, FIG. 3C, FIG. 3D, FIG. 4A, FIG. 4B, FIG. 4B, FIG. 4C, FIG. 5A, FIG. 5B, FIG. 6A, and FIG. 6B.

After creating the breath analysis device 830, this device must be attached to a test system, a step shown at 832. Examples of test systems that the breath analysis device 830 could be attached to are shown in FIG. 7 and FIG. 8, but could comprise any test system capable of being understood by anyone skilled in the art.

As part of the method for validating a breath analysis, device, system or method shown in FIG. 10, the breath analysis device 830 also needs to be tested with human subjects who have and don't have the health status of interest, as shown at step 890. The information from this clinical testing of the device 890 can be combined with the laboratory testing 840 to validate the sensitivity and specificity of the device 830 in response to a health status of interest, as shown at 895. For example, the clinical testing 890 might be of human subjects who have/don't have diabetes or who are/aren't on a strict ketogenic diet. The validation in step 895 is then to confirm that the device 830 gives the same result as another way of checking for this health status (such as diabetic yes/no or ketogenic diet yes/no).

Figure 11:
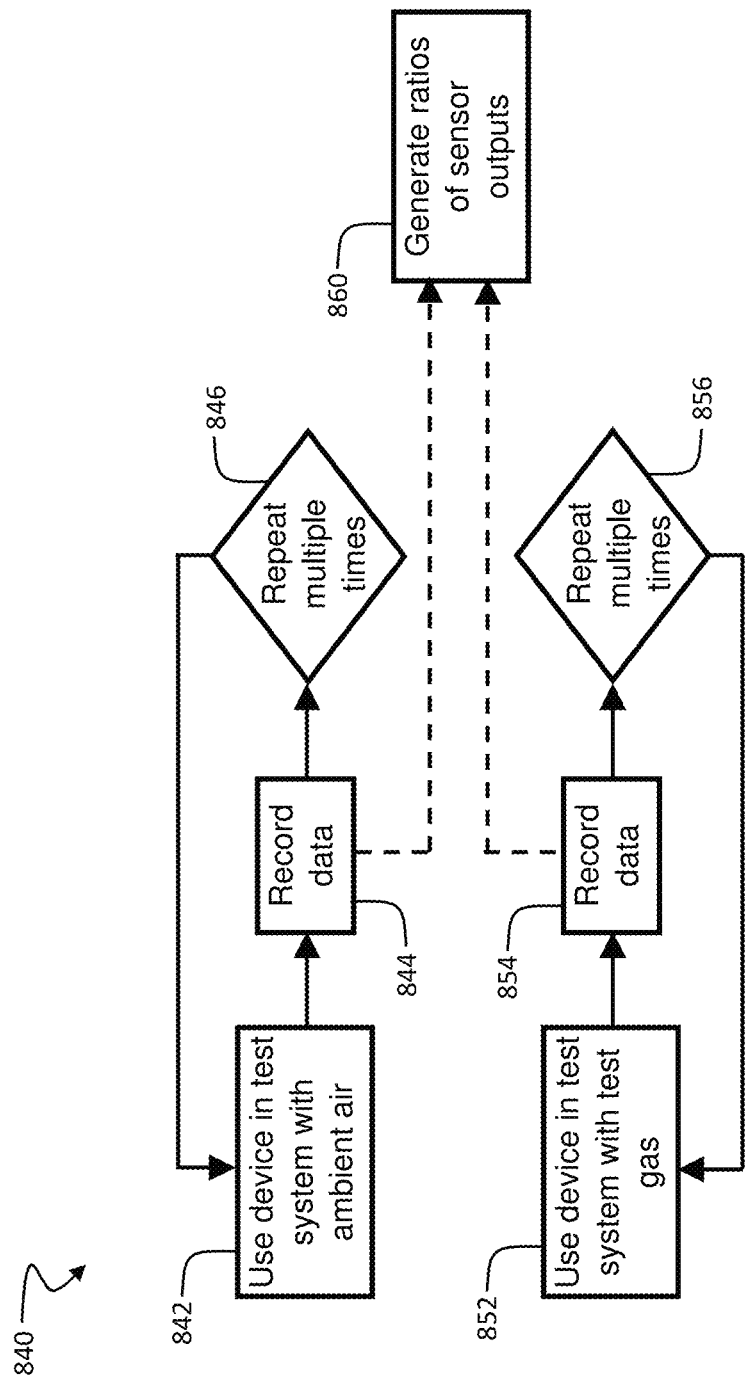
FIG. 11 shows a method for validating a breath device response to a test gas.

FIG. 11 details one example of a method for validating sensitivity and specificity of a breath analysis device in response to a test gas 840, as was shown as one of the steps in FIG. 10. The method shown in FIG. 10 starts with using the device (830 of FIG. 10) in a test system (such as the systems illustrated in FIG. 7 and FIG. 8) with ambient air, as shown at 842. The data from this ambient air test is recorded 844, and the test and recording of data is repeated multiple times 846. Similarly, the device (830 of FIG. 10) is used multiple times 856 with test gas samples, as shown at 852, and this data is recorded 854. The recorded data from ambient air 844 and test gas 854 are then used to generate ratios of sensor outputs, as shown at 860. In one embodiment, those ratios are the sensor outputs with test gas divided by the sensor outputs for ambient air. The reason for performing the test multiple times (steps 846 and 856) is that this provides an indication of the repeatability of the device and its sensors.

Figure 12A:
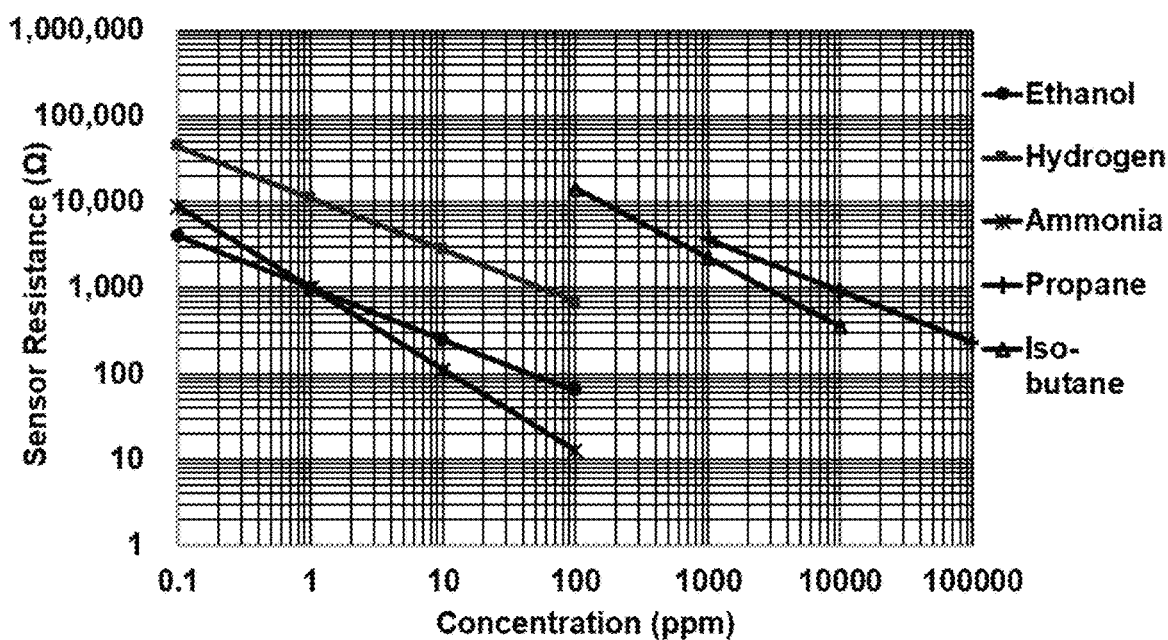
Figure 12B:
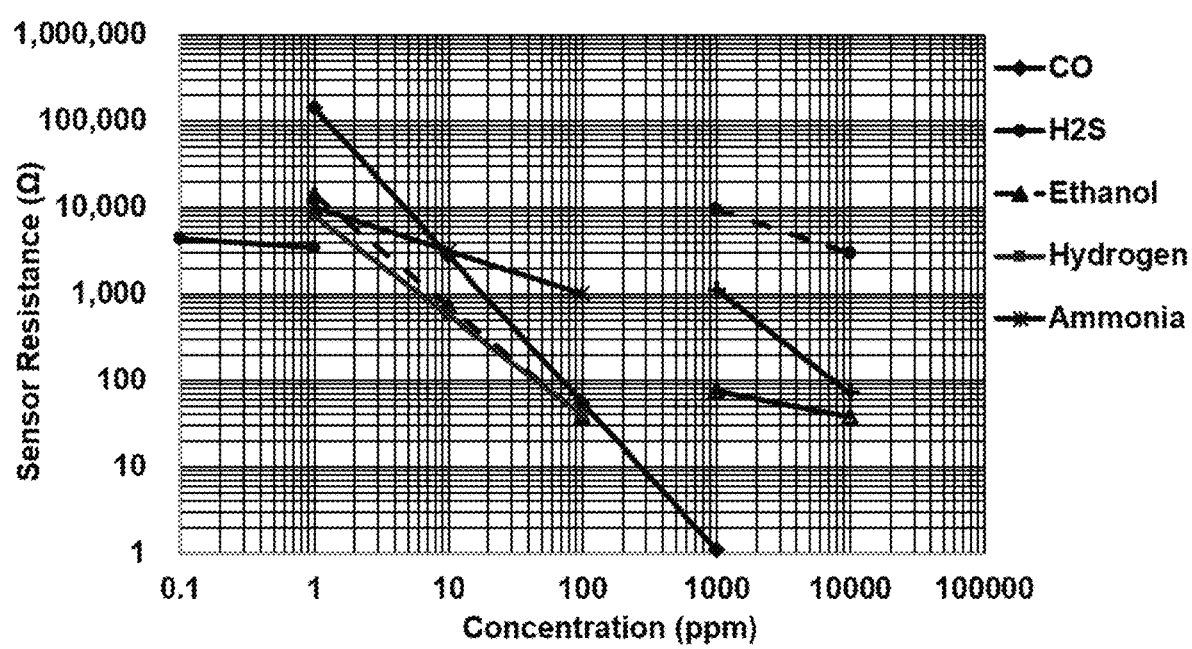

FIG. 12A, FIG. 12B, and FIG. 12C show an example of test data for three sensor types. This data is available in the prior art for commercially-available sensors. More specifically, FIG. 12A shows an example of the relationship between the concentration of five gases in air (Ammonia, Ethanol, Hydrogen, Propane, and Iso-butane) and the sensor resistance (Rs) for a first type of sensor. FIG. 12B shows an example of the relationship between the concentration of eight gases in air (Ammonia, Ethanol, Hydrogen, Propane, Iso-butane, H2S, CO, and Methane) and the sensor resistance (Rs) for a second type of sensor. FIG. 12C shows an example of the relationship between the concentration of three gases in air (NO, NO2, and Hydrogen) and the sensor resistance (Rs) for a third type of sensor. In looking at this data, it should be apparent that each sensor responds differently to different compounds (i.e., the output resistance values for the different types of sensors are dissimilar). It is also noteworthy, that for the three sample sensor types shown, there is a log-log relationship (the logarithm of the concentration is proportional to the logarithm of the resistance) between concentration and sensor output. Stated another way, the relationship between the logarithm of concentration and the logarithm of sensor output (resistance relative to ambient air) is a straight line. The relationship lines between concentration and sensor output shown in FIGS. 12A, 12B, and 12C are for combinations of ambient air and one other compound. It can be understood that such relationships between concentration and output can be more complex when an air sample contains a plurality of added biomarkers at varying concentrations. It can also be understood that having a large number of different types of sensors that each respond differently to different compounds will be beneficial in trying to analyze the compounds and concentrations that might be in a real breath sample or the odors coming from sweat, urine, or feces.

FIG. 12D shows an example of actual test data from a breath analysis device that comprises three sensor types and a flow meter. This test data could come from a human or from a test system of the type illustrated in FIG. 7, FIG. 8, or FIG. 9. For simplicity in presentation, the test data shown in FIG. 12D is from a test in which the concentration of compounds varies as a function of time, as would be the case for human breath. This test data can thus be used to illustrate the concept illustrated in FIG. 11. If we assume that that Sample 1 is from ambient air (at the top of a person's breath) and that Sample 2 is from the bottom of a person's breath, we can see the changes in output that occurred between the time when Sample 1 and Sample 2 were recorded by the sensors, as shown by the curves of values of the Type 1, Type 2, and Type 3 sensors between the time of Sample 1 and Sample 2.

FIG. 12E shows a sample calculation of the output ratios (Step 860 in FIG. 11) for the three sensors types at the two sampling times in the test data shown in FIG. 12D. From this, it can be seen that these ratios are different for each sensor. This concept of having multiple sensor types to detect complex mixtures of multiple compounds and concentrations can be applied much larger combinations of compounds and sensors. For example, the system could use at least 5 sensor types, at least 10 sensor types, at least 20 sensor types, at least 50 sensor types, at least 100 sensor types, at least 200 sensor types, at least 500 sensor types, and at least 1000 sensor types. Some research has shown that dogs have on the order of 1000 different biological sensor types. Thus, the system illustrated herein could be applied to such large arrays of different sensor types in order to be equally tuned to the subtle differences in odors for different health conditions.

The response of a sensor, such as a MOS sensor, can be modified in many different ways as has been described in other parts of this document. One of those modifications can be the result of the materials chosen. Tin dioxide and tungsten oxide is examples of a base material that can be used for MOS sensors. These base materials can be doped with a variety of other chemicals to change the resulting response of the sensors to various gaseous compounds as was illustrated in FIG. 12A, FIG. 12B, and FIG. 12C. The response of a particular sensor type to a test gas can also be changed by altering the temperature of the metal oxide semiconductor (MOS) layer. These temperature changes can be made by changing the power going through a heating element that is proximate or part of the MOS semiconductor layer. The power going through the heating element can be controlled through changes in the voltage or current going through the heater element.

FIG. 12F, FIG. 12G, FIG. 12H, and FIG. 12I show an example of the ratios of sensor outputs that can be generated at step 840 in FIG. 10, as further detailed in FIG. 11. More specifically, this is an example of the output of step 860 in FIG. 11. In the example shown in these data tables and graphs, the average output of three different metal oxide semiconductor (MOS) sensors (Sensor 1, Sensor 2, and Sensor 3) is shown with those sensors at 5 different heater voltages (3.7 Volts, 3.3 Volts, 2.9 Volts, 2.5 Volts, and 2.0 Volts), for two different test gases (Gas 1 and Gas 2) with those sensor outputs for those test gases being divided by the equivalent sensor outputs for ambient air. Note that FIG. 12F and FIG. 12G are for Gas 1 and that FIG. 12H and FIG. 12I are for Gas 2. To highlight the differences as a visible pattern, the ratios shown in FIG. 12F and FIG. 12H have been converted to bar charts in FIG. 12G and FIG. 12I, respectively. Thus, one can see that the ratios of outputs vary based on the gas, the sensor, and the heater voltage, which means that the instrument will have different sensor outputs depending upon the mix of gases in a sample. These variations in sensor output can be used to determine the compounds in an air sample emitted by a human, and/or to compare breath signatures from a test subject with similar data from other healthy and unhealthy human subjects in order to develop a health status score and/or control the performance of a medical procedure as described previously.

The ratios calculated in FIG. 12E, FIG. 12F, and FIG. 12H are simply the output generated when the test gas is flowing over the sensor divided by the output generated by this same sensor when ambient air is flowing over the sensor. Because concentration as a function of sensor output is typically shown as straight lines on a log-log plot (as was shown in FIG. 12A, FIG. 12B, and FIG. 12C with output being the resistance of the MOS sensor), it is easier from an analytic standpoint to work with and display the logarithm of the ratio of sensor outputs. This sensor output ratio logarithm can then be used to predict the exponent of the concentration over the "linear" range of an MOS sensor's response to the concentrations of a particular compound.

Figure 13:
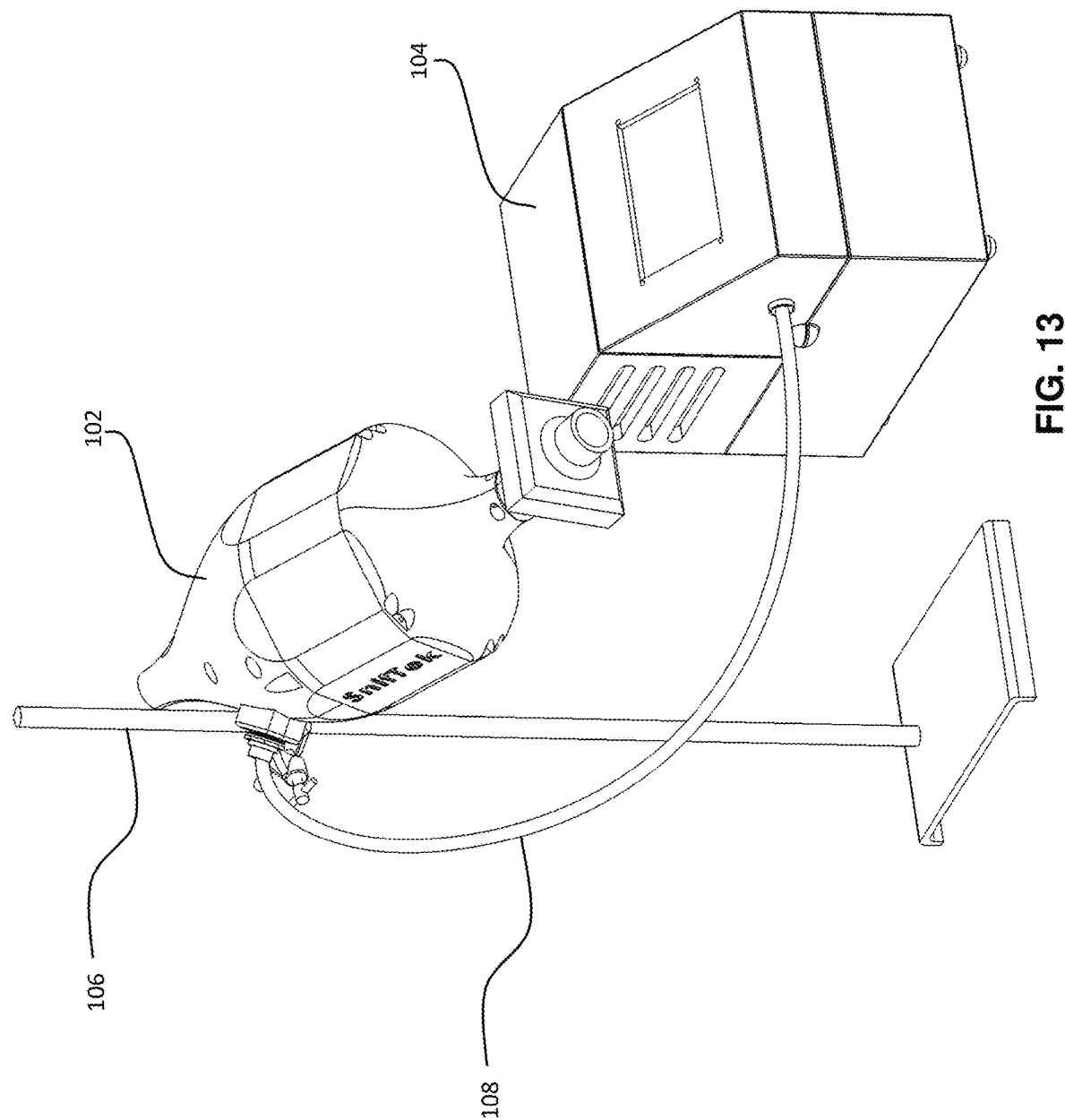
FIG. 13 shows an isometric view of one embodiment of a system for direct health status analysis from human breath.

Moving now to the physical mechanical details of one embodiment, FIG. 13 shows an isometric view of a system for direct health status analysis from human breath. This system comprises a breath device 102 (also called a sensor unit) mounted on a retort stand 106, a system computer 104 unit, and a cable 108 that connects the breath device 102 to the system computer 104 unit. The system computer 104 unit comprises a housing that holds a power source, a power distribution board, and a system computer (2300 in FIG. 23) that controls the breath device 102 via the cable. Although the breath device in FIG. 13 is mounted on the retort stand 106, the mounting for the breath device 102 can vary depending on the application.

Figure 14:
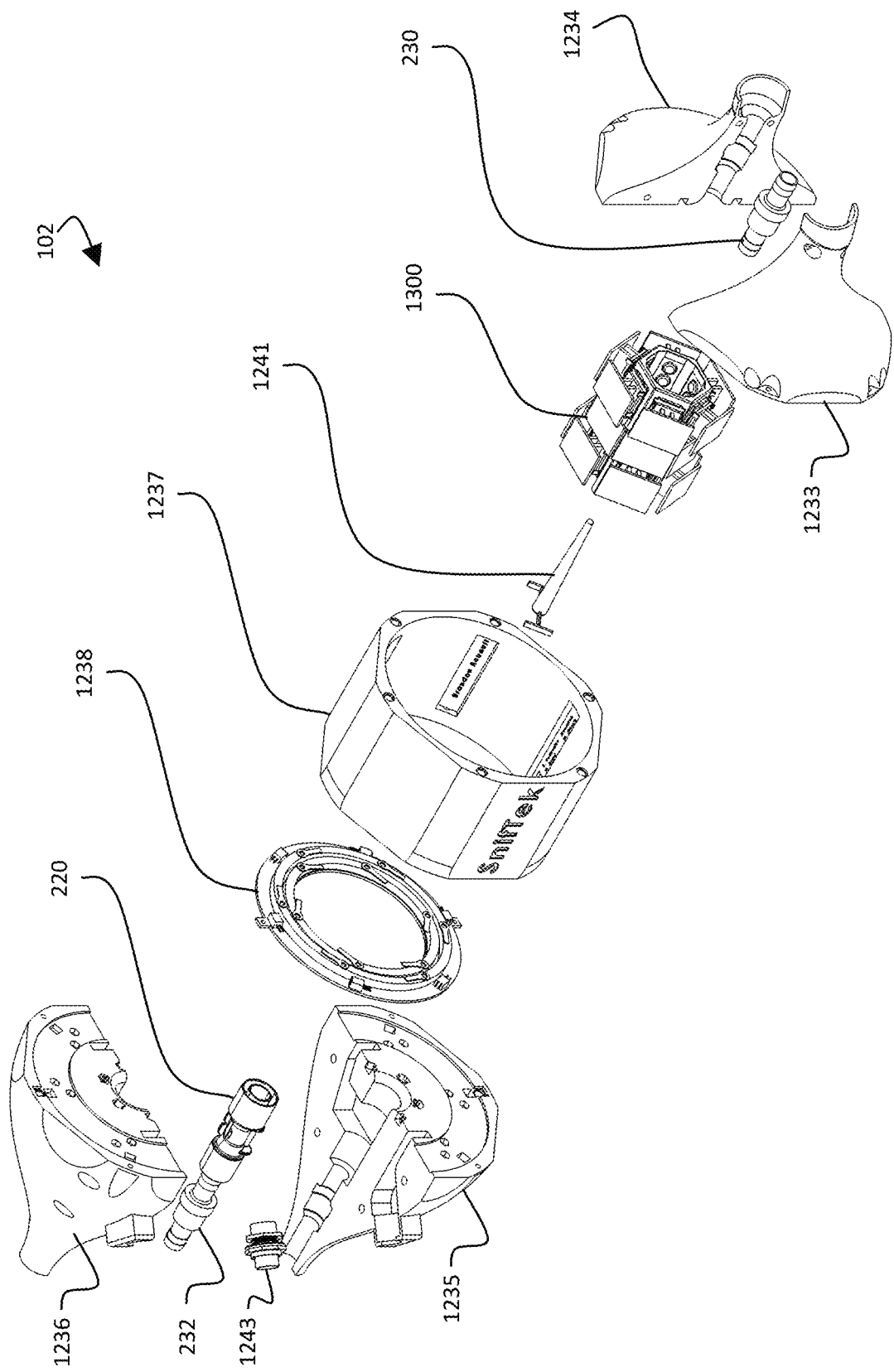
FIG. 14 shows an exploded view of the sensor unit of the system of FIG. 13.

FIG. 14 shows an exploded view of the sensor unit (breath device) of the system of FIG. 13. This shows two back halves of the sensor casing (1235 and 1236), which surround the outlet one way valve 232 and flow meter 220. A cable connector 1243 for attaching the cable (108 in FIG. 13) is also assembled into the two back halves of the casing (1235 and 1236). A circular shaped bus board 1238 distributes power and communication signals from the cable connector 1243 to other electronic components in the sensor unit 102. A flow director 1241 is inserted into the sensor chamber assembly 1300, which is then slotted into the back half of the casing (1235 and 1236). The middle of the device casing 1237 then surrounds the sensor chamber assembly 1242. Finally, after inserting the front one-way valve 230 into the two front halves of the device casing (1233, 1234), the front half is screwed on to the other components to create a fully-assembled breath device (or sensor unit) 102.

Figure 15:
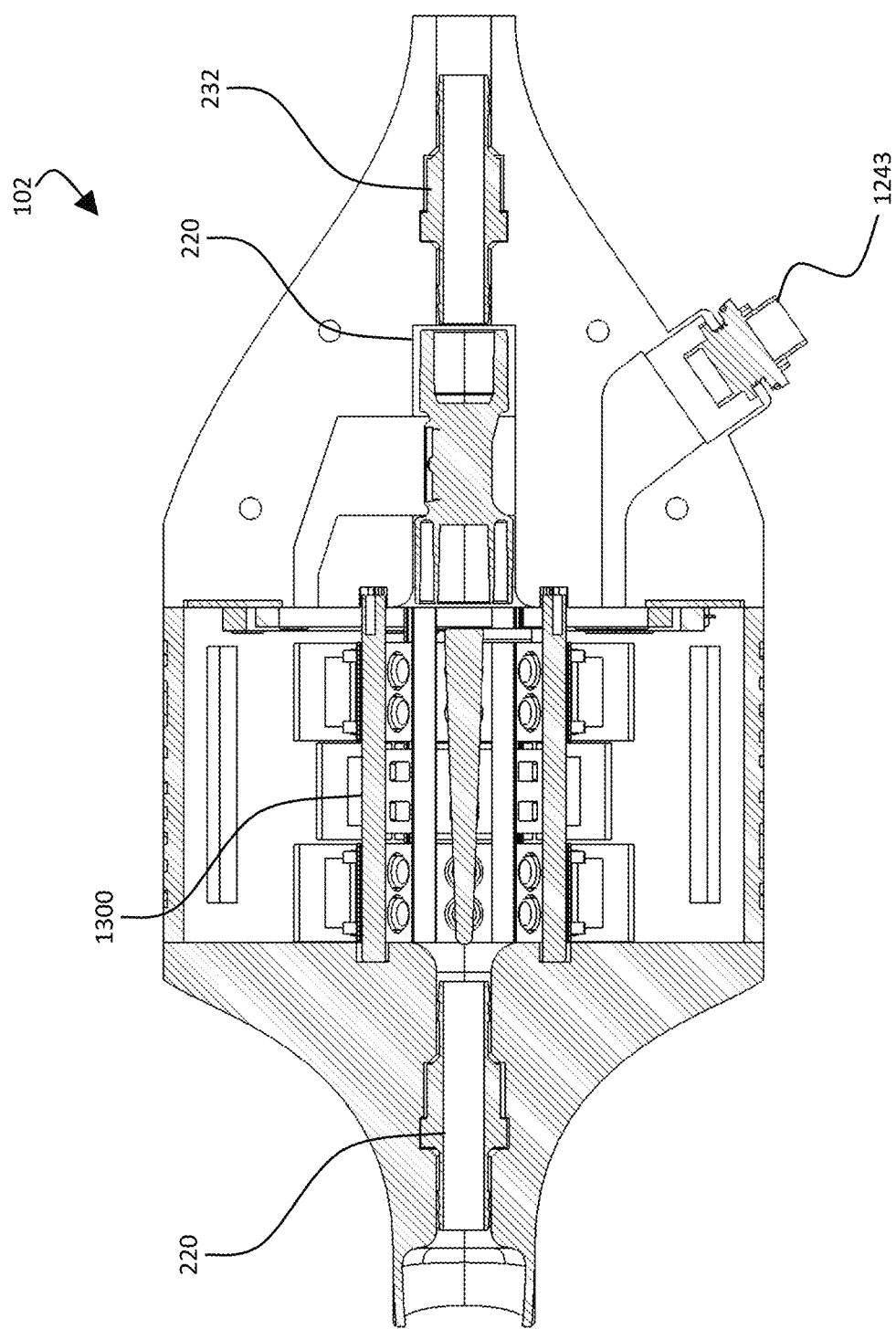
FIG. 15 shows a section of view of the sensor unit of the system of FIG. 13.

FIG. 15 shows a section of view of the sensor unit of the system of FIG. 13. Breath enters on the left of the view shown through an entry check valve (one-way valve) 230. The breath then passes through the sensor chamber assembly 1300, followed by the flow meter 220, and finally through the rear one-way (check) valve 232. The cables controlling the device and providing power pass through a cable connector 1243 and also connect to the flow meter 220 through a separate passage in the interior of the breath device (or sensor unit) 102.

Figure 16:
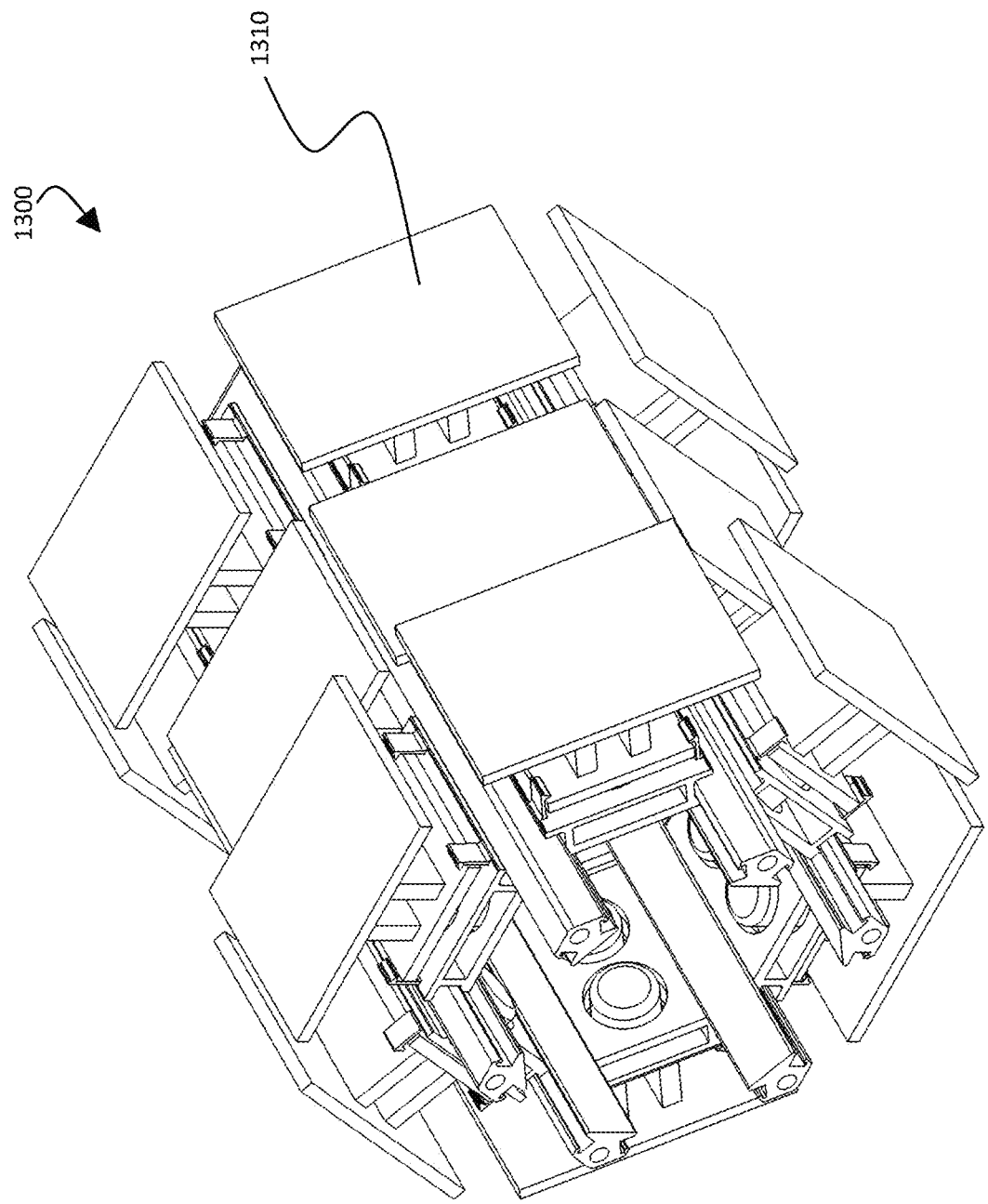
FIG. 16 shows an isometric view of the sensor chamber of the sensor unit of FIG. 14 and FIG. 15.

FIG. 16 shows an isometric view of the sensor chamber 1300 of the sensor unit of FIG. 13, FIG. 14 and FIG. 15. Sensor boards of various heights can slide into a rail system as will be shown in greater detail with reference to later drawings. Control boards 1310 can be seen on the exterior of the sensor chamber assembly 1300.

Figure 17:
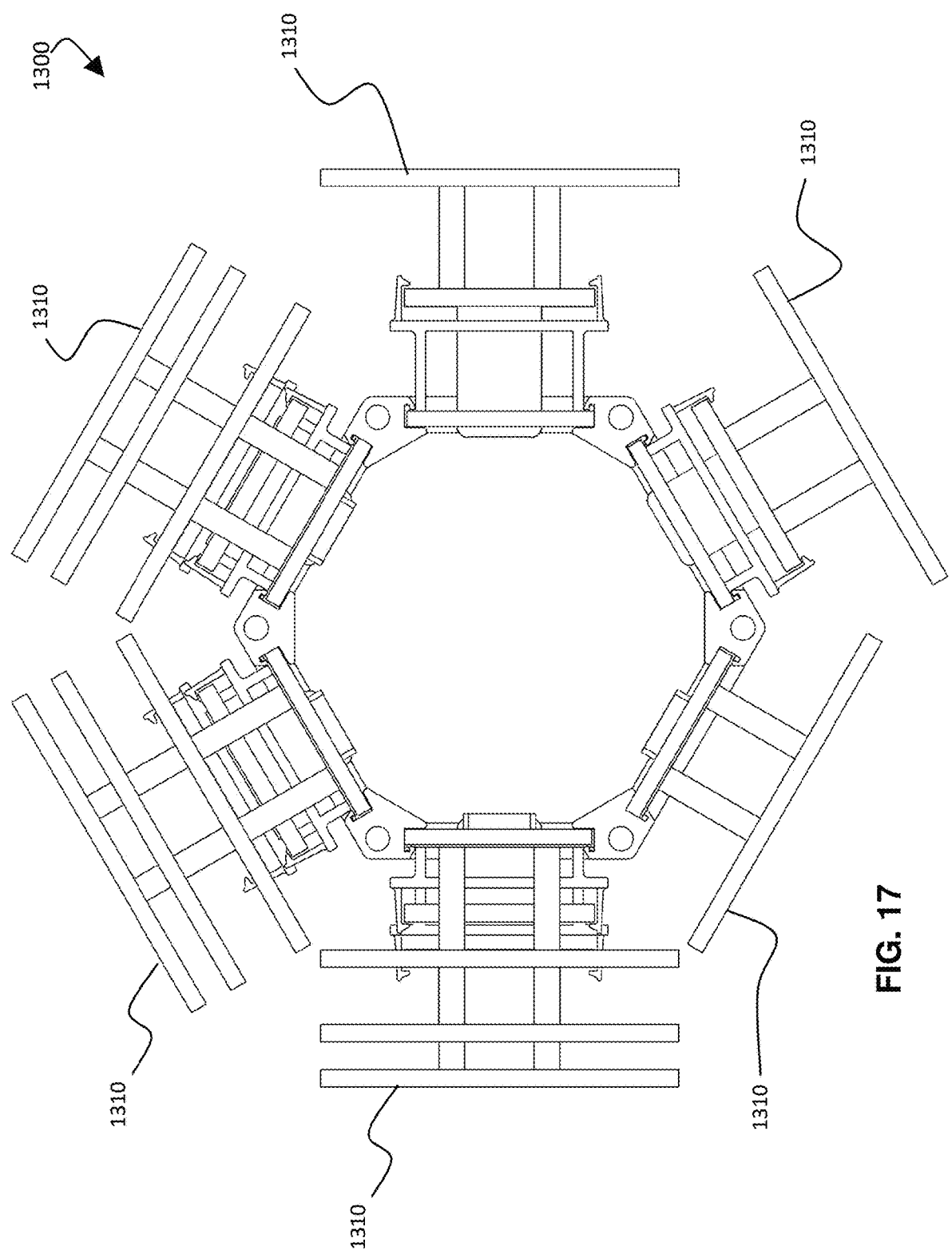
FIG. 17 shows an end view of the sensor chamber of FIG. 16.

FIG. 17 shows an end view of the sensor chamber 1300 of FIG. 16 and the control boards 1310. The sensor chamber assembly 1300 can hold various sizes of sensors on sensor boards in a manner that the tops of the sensors are at the same height on the inner opening of the sensor chamber 1300. Each rail of the sensor chamber assembly 1300 can hold any height of sensor without interrupting flow within the interior of the sensor chamber 1300. There are slider-clips that vary in height. These slider-clips can be designed as 3D CAD models that are easily edited using 3D modeling programs. This allows for a wide variety of sensors to be used in the sensor chamber assembly 1310. In this illustration there are three sensor heights shown. This creates variations in the locations of the control boards 1310 relative to the inside of the sensor chamber assembly 1310.

Figure 18:
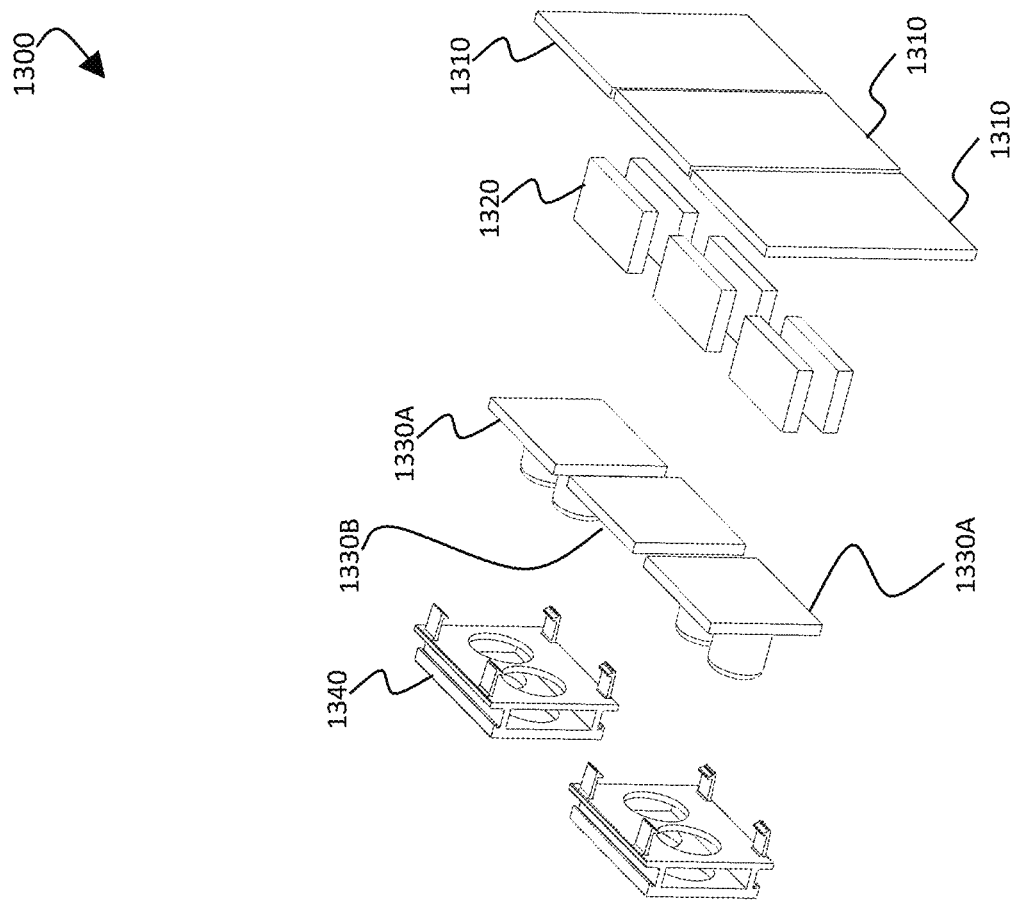
FIG. 18 is a partially exploded view of the sensor chamber of FIG. 16 and FIG. 17.
Figure 18:
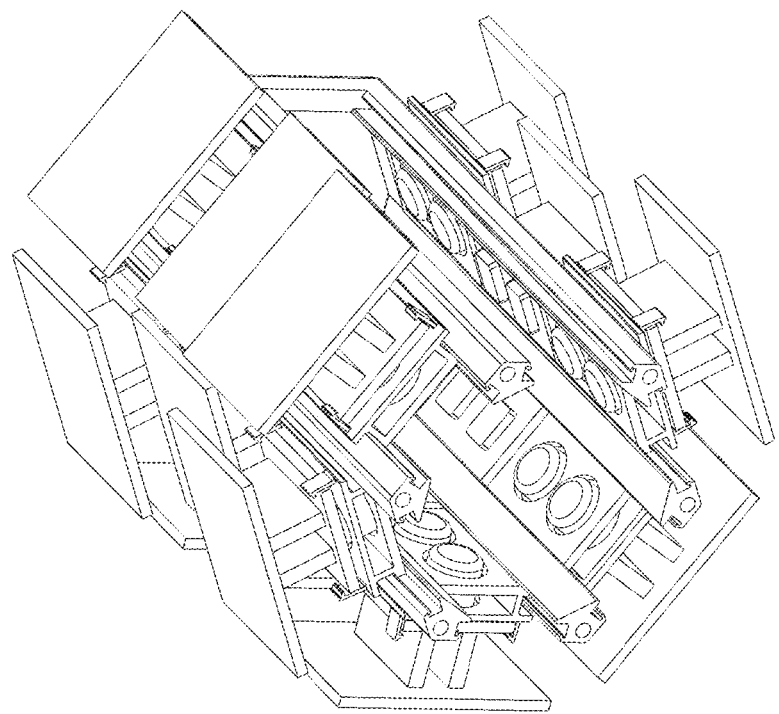

FIG. 18 is a partially exploded view of the sensor chamber assembly 1300 of FIG. 16 and FIG. 17. This illustrates how components are attached to the rail system and how the control boards 1310, connectors 1320, sensor boards (1330A and 1330B), and slider-clips 1340 connect together. It should be noted that the middle sensor board 1330B uses a low-profile surface mount sensor which does not require a slider-clip 1340 because the sensors are the minimum height and are flush with the inside of the sensor chamber assembly without needing a slider-clip 1340.

Figure 19:
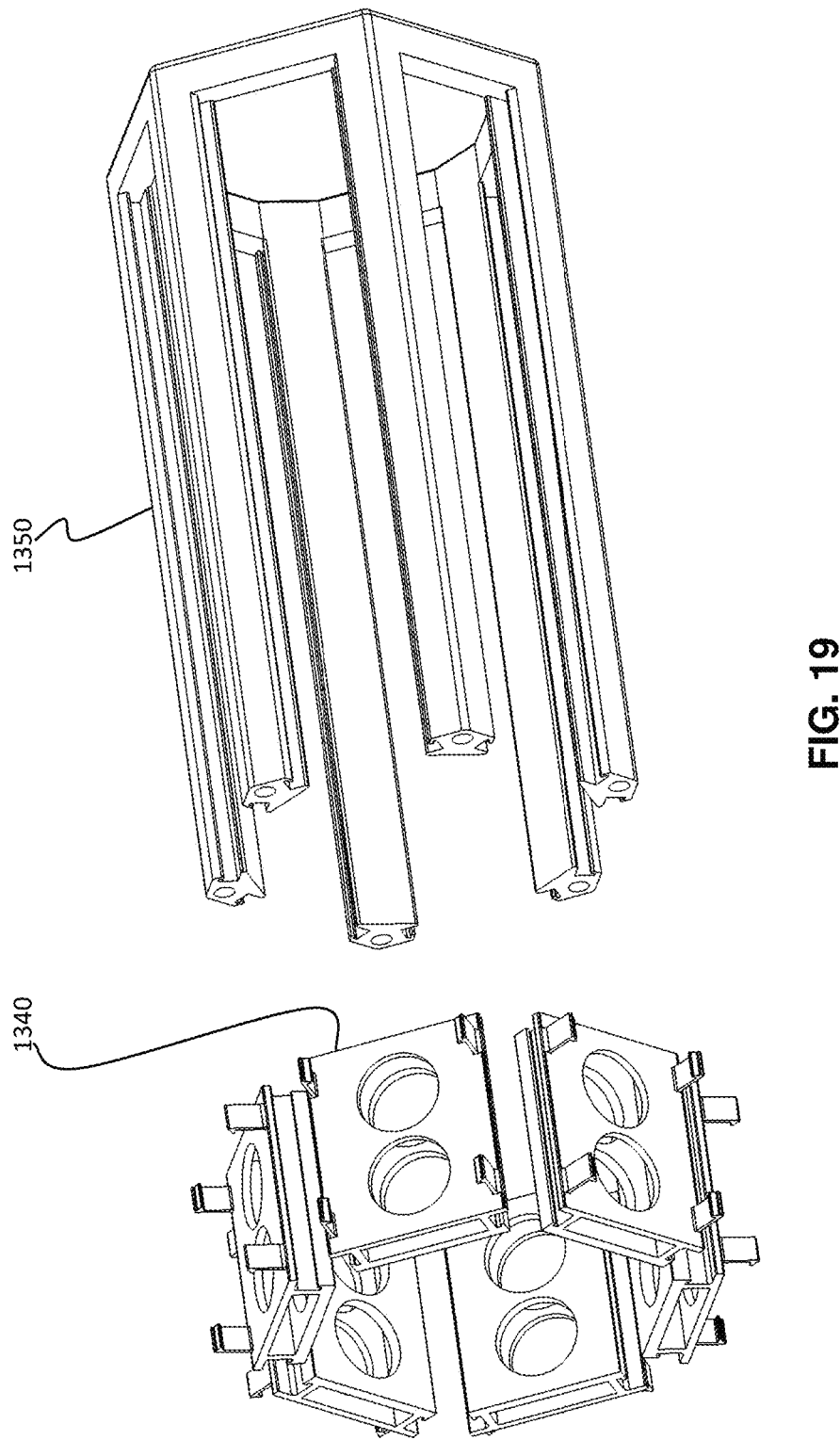
FIG. 19 shows mechanical details of the clips and sliders of the sensor chamber of FIG. 16.

FIG. 19 shows mechanical details of how the slider-clips 1340 and the rail system chamber frame 1350 fit together Each slider-clip 1340 has a notch that matches the railing system on the chamber frame 1350 and ensures the slider-clips do not fall out and also assist in holding the frame legs together.

Figure 20B:
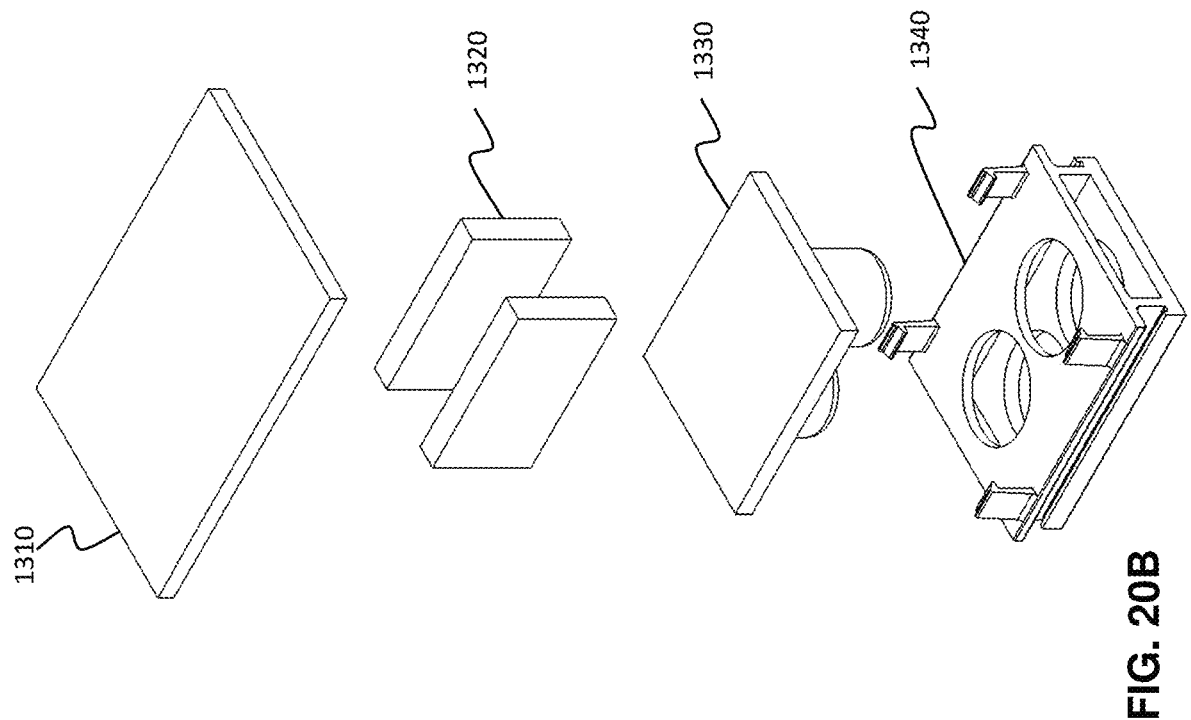
FIG. 20B shows an exploded view of FIG. 20A.
Figure 20A:
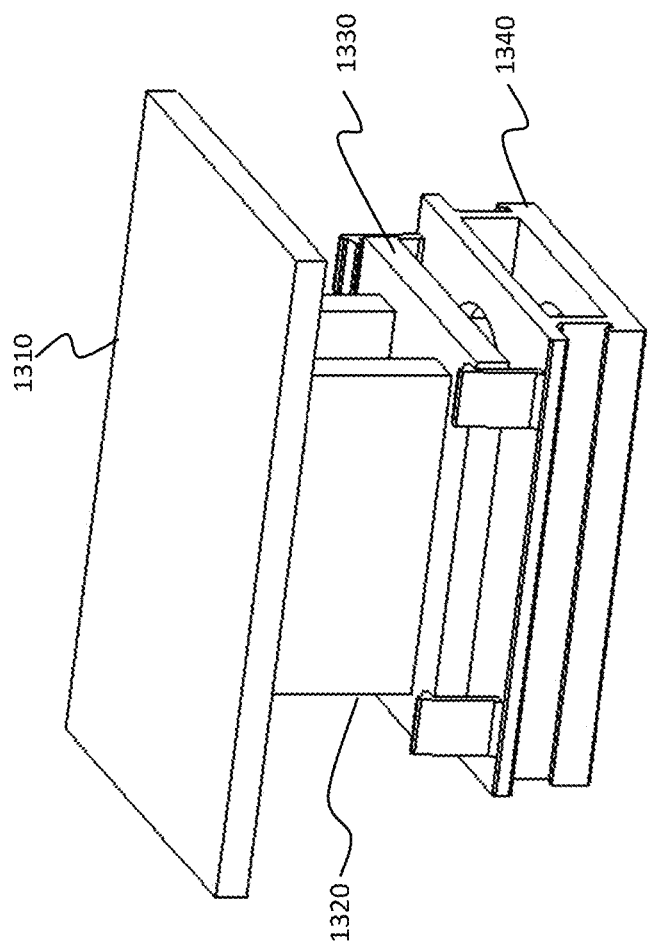
FIG. 20A shows an isometric view of the clips, circuit boards, and spacers used in the sensor chamber of FIG. 16, FIG. 17, and FIG. 18.

FIG. 20A shows an isometric view of the slider-clips 1340, control boards 1310, connectors 1320, and sensor boards 1330 used in the sensor chamber of FIG. 16, FIG. 17, and FIG. 18. FIG. 20B shows an exploded view of FIG. 20A, and illustrates these same components. The slider-clips 1340 contain holes for sensors that are located on the sensor boards 1330 to pass through. Flexible clips in the slider clips 1340 attach to the sensor boards 1310. In this configuration, the sensors protrude just past the interior of the interior-oriented face of the slider-clips 1340. This allows for proper interaction with gaseous compounds while still allowing laminar flow within the sensor chamber of FIG. 16, FIG. 17, and FIG. 18. The through hole shape may be configured to incorporate many different sensor shapes while only being limited by the size of the slider-clips.

Figure 21B:
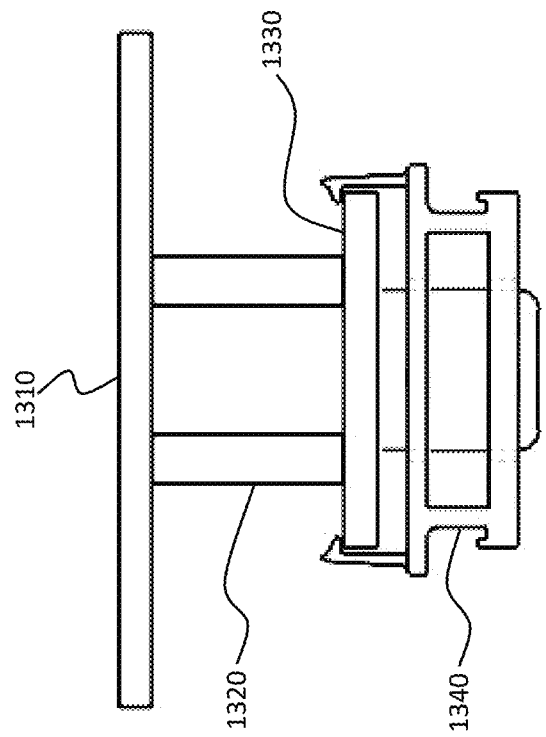
FIG. 21A and FIG. 21B show end views of two different sensor assemblies that vary in having different sizes of clips to accommodate different sensor heights.
Figure 21A:
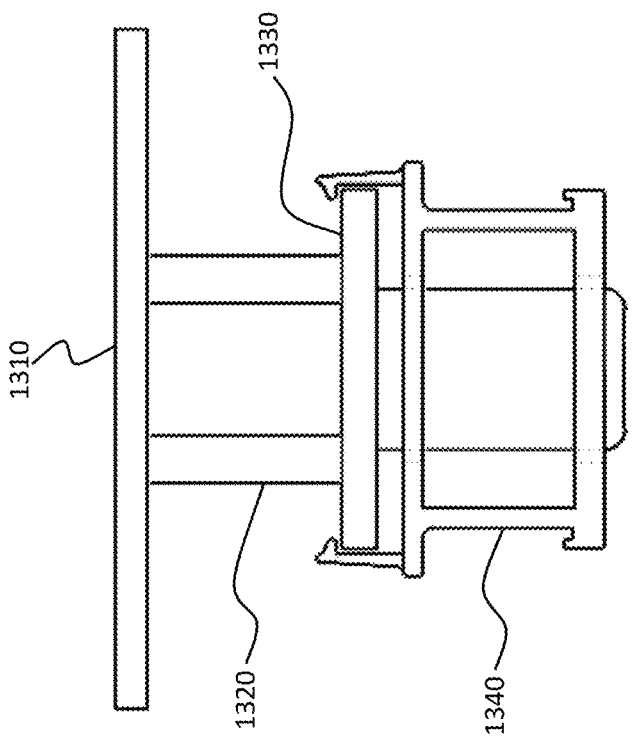
Figure 22B:
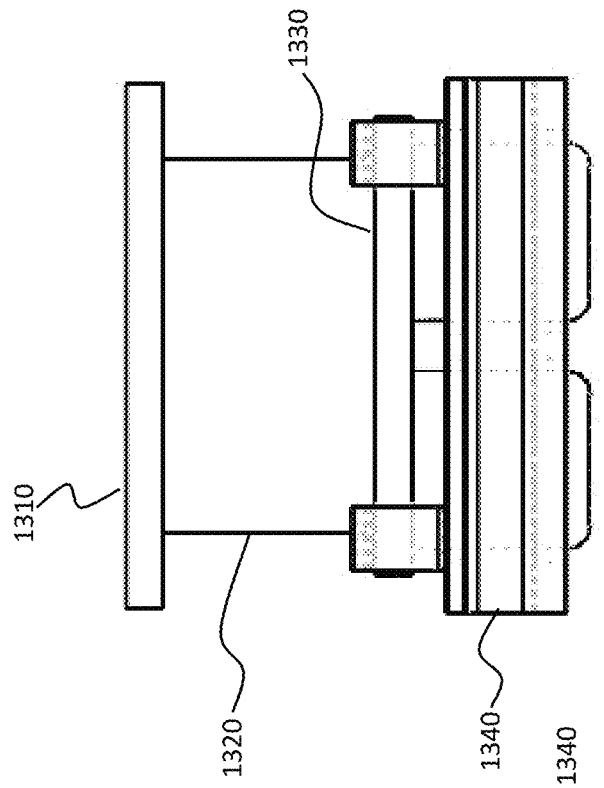
FIG. 22A and FIG. 22B show side views of the two different sensor assemblies of FIG. 21A and FIG. 21B.
Figure 22A:
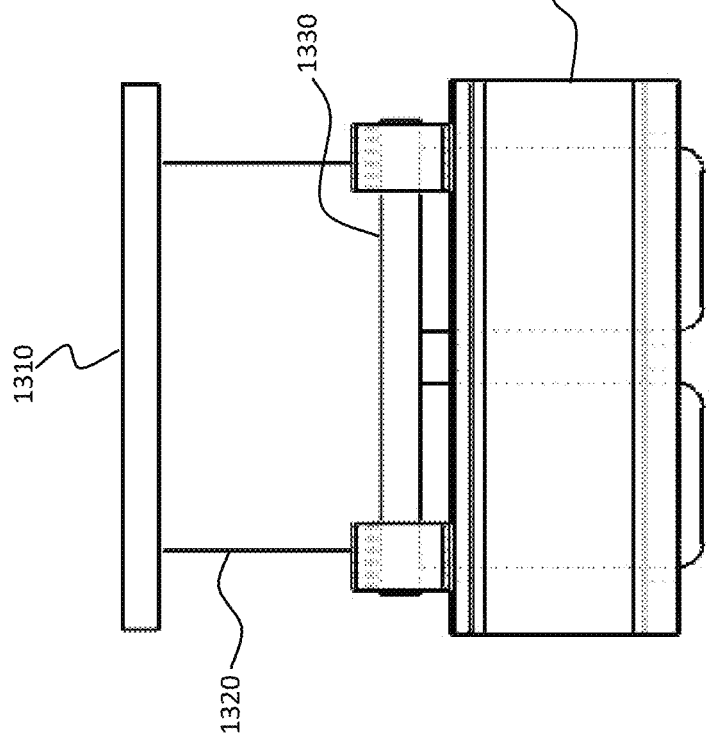

FIG. 21A and FIG. 21B show end views of two different sensor assemblies that vary in having different sizes of slider-clips to accommodate different sensor heights while maintaining a relatively smooth inner sensor chamber face. The varied height is limited by the size of the device casing as shown in FIG. 15. FIG. 22A and FIG. 22B show side views of the two different sensor assemblies of FIG. 21A and FIG. 21B. All of these illustrations show the slider-clips 1340, control boards 1310, connectors 1320, and sensor boards 1330.

Figure 23:
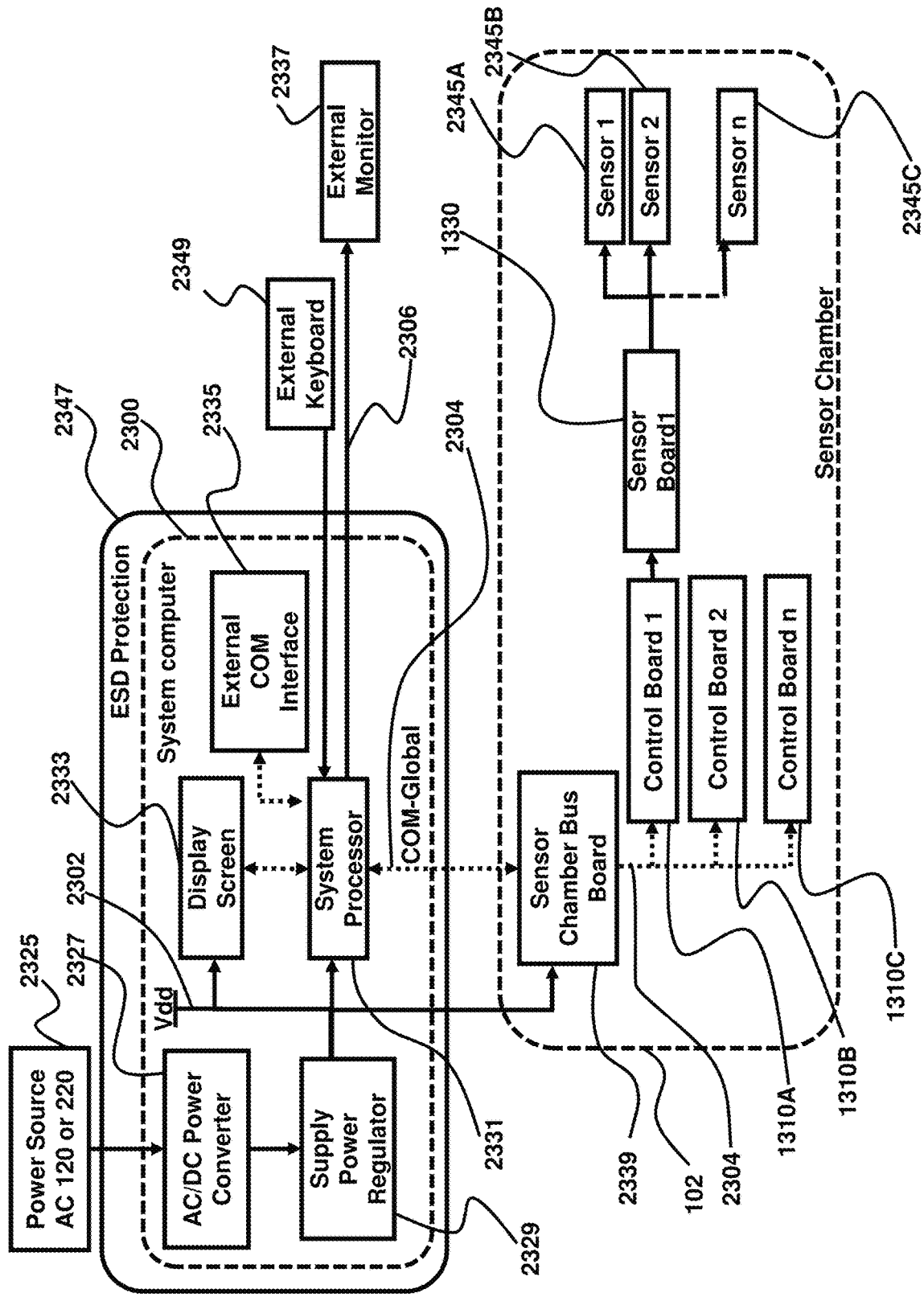
FIG. 23 is a generalized block diagram of the electronics of the system of FIG. 13.

FIG. 23 is a generalized block diagram of the electronics of the system of FIG. 13. This system electronics can comprise:

(a) A system computer shown at 2300, which is inside the system computer unit shown at 104 in FIG. 13;

(b) A power source shown at 2325, typically in the form of a connection to a standard wall outlet;

(c) A device to convert the alternating current (AC) from the power source 2325 to direct current (DC), as shown at 2327;

(d) A power supply regulator shown at 2329 that generates a stepped down supply voltage, labeled as Vdd and shown at 2302 in FIG. 23 and other electronics diagrams in this document;

(e) A system computer processor 2331;

(f) A display screen 2333 mounted inside the system computer unit (104 in FIG. 13);

(g) An external communications interface 2335, which could use any technology understood by those skilled in the art, such as Bluetooth, Ethernet, or WiFi;

(h) An external monitor, shown at 2333;

(i) A connection 2306 to the external monitor;

(j) An external keyboard, shown at 2349;

(k) An electrical interconnect assembly 2339 (which can be in the form of the circular shaped bus board shown at 1238 in FIG. 14) for communication between the system computer processor 2331 and the control boards 1310A, 1310B, and 1310C in the sensor chamber 102 (previously shown in FIG. 13);

(l) One or more sensor boards 1330 connected to each control board; and (m) one or more sensors, 2345A, 2345B, and 2345C connected to the sensor boards.

Further referring to FIG. 23, it should be noted that there can be multiple sensors 2345 for each sensor board 1330, multiple sensor boards for each control board 1310, and multiple control boards attached to the sensor chamber bus board 2339. The connection between the control boards 1310 and the sensor chamber bus board 2339 is over a global communication bus shown at 2406. The system can also comprise electro-static discharge protection as shown at 2347. This ESD protection can be added to any part of the electronics as can be understood by anyone skilled in the art and can take the form of shielding, diodes, and any other devices capable of understood by anyone skilled in the art.

FIG. 24, FIG. 25, FIG. 26, FIG. 27, FIG. 28, FIG. 29, and FIG. 30 show different embodiments of the control boards that were shown at 1310A/B/C and sensor boards 1330 that were shown in FIG. 23. Generally speaking, most or all of these control boards comprise the following signaling and communicating elements:

(a) The use of a supply voltage shown at 2302 and/or labeled as Vdd;
(b) The use of a global communication bus shown at 2406 and/or labeled as COM-Global;
(c) The use of an internal communication bus shown at 2304 and/or labeled as COM;
(d) The use of an analog voltage supply shown at 2404 and/or labeled as Vdda;
(e) The use of a sensor output voltage signal shown at 2410 and/or labeled as V-sense;
(f) The use of a heater voltage signal shown at 2412 and/or labeled as VH;
(g) The use of a heater current signal shown at 2414 and/or labeled as Current Sense; and
(h) The use of a select signal shown at 2416 and/or labeled as SEL.

Further referring to FIG. 24, FIG. 25, FIG. 26, FIG. 27, FIG. 28, FIG. 29, and FIG. 30, these embodiments can share the following circuit elements:

(a) A system connector 2425;
(b) A voltage regulator 2427;
(c) A communication level shifter 2429;
(d) A power amplifier 2431;
(e) One or more fixed resistors 2433;
(f) One or more externally controlled variable resistors (e.g., digital potentiometers) shown at 2437 and/or labeled as ECVR;
(g) A board-to-board connector 2435 between a controller board and a sensor board that is also labeled B2B;
(h) A multiplexer with eight analog input channels and one analog output channel 2439, which is typically labeled as a MUX;
(i) A multiplexer with two analog input channels and one analog output channel 2441, which has been labeled as a 2:1 MUX;
(j) A voltage reference 2451;
(k) An output amplifier 2453;
(l) A plurality of analog to digital converters 2455, also labeled as ADC; and a
(m) A control board processor 2457; such as a microcontroller, FPGA (field programmable gate array), CPLD (complex programmable logic device) or similar device.

Further referring to these drawings, there can be multiple sensors on any sensor board. The sensor boards that were described generically as 1330 in previous illustrations can have the specific embodiments shown as 2481 (in FIG. 24, FIG. 25, FIG. 26, and FIG. 27), 2981 (in FIG. 28), 2991 (in FIG. 29), and 3081 (in FIG. 30), and these sensor board embodiments can comprise the following elements:

(a) The board-to-board connector 2435 for connection to the control board;
(b) One or more sensor packages 2447 that further comprises a heating element (heater) 2443 and metal oxide semiconductor (MOS) 2445; and
(c) a temperature sensor 2449.

Further referring to the power amplifier 2431, this could be implemented using a Current DAC (digital to analog converter) or a Voltage DAC followed by an NPN transistor in a closed loop. The output of the power amplifier 2431 is the voltage input for the heater 2443. When there are multiple sensors on the sensor board, in some configurations, it is beneficial to have different heater voltage values (Vh, as shown at 2412) for the different sensors 2447 on the sensor board 2481.

Figure 25:
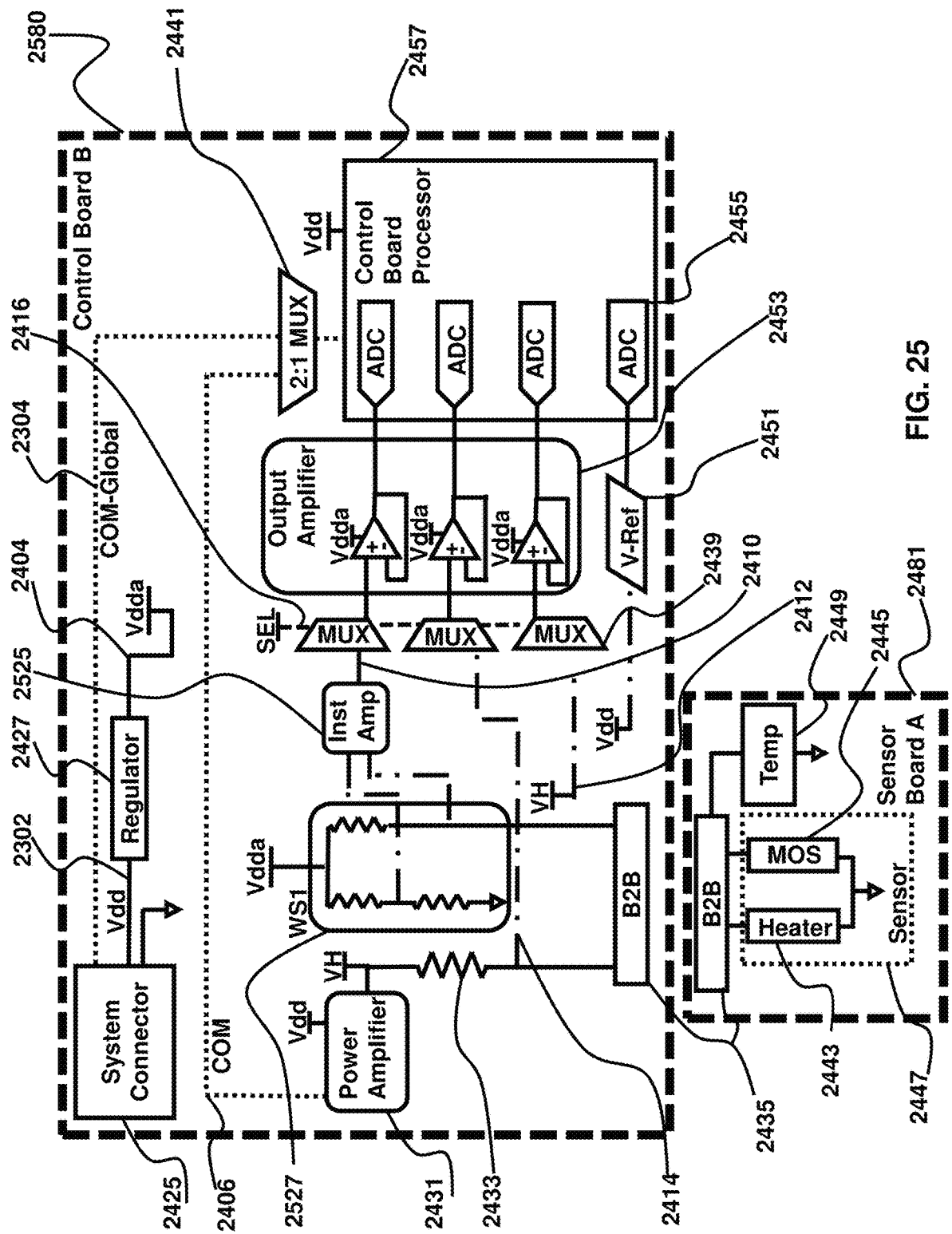
FIG. 25 shows an alternate embodiment of the circuit of FIG. 24 in which the voltage divider circuit has been replaced by a Wheatstone bridge circuit.

Referring now specifically to the different control board configurations, FIG. 25 shows a control board configured for voltage division sensor measurement at 2480. One or more sensors configured for one or more a four-wire analog MOS sensors 2481 can be connected to this voltage divider control board 2480. The voltage divider control board shown 2480 uses a voltage divider circuit comprising an externally-controlled variable resistor 2437 to generate a sensor output signal 2410 from a sensor 2447. If there is more sensor, the voltage divider control board 2480 will have more than one voltage divider circuit.

Figure 24:
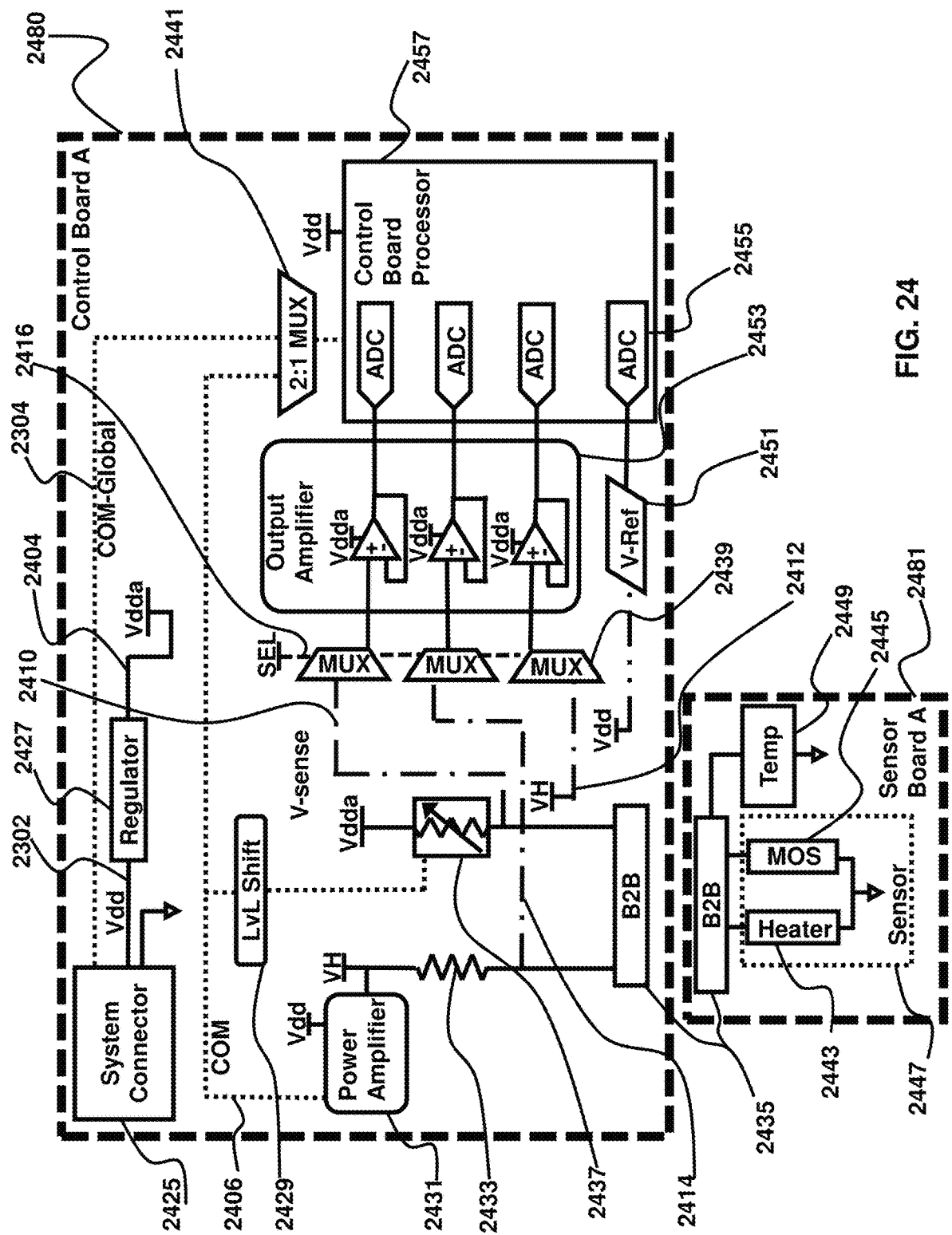
FIG. 24 shows a typical voltage divider circuit for a MOS sensor when used in embodiments of the invention.

FIG. 25 shows an alternate embodiment of the circuit of FIG. 24 in which the voltage divider circuit has been replaced by a Wheatstone bridge circuit shown at 2527, and also labeled as WS1. In the configuration shown in FIG. 25, the control board for Wheatstone bridge sensor measurement 2580 works with the same four-wire analog sensor board 2481 as was shown in FIG. 24. It should be noted that the specific Wheatstone bridge circuit shown at 2527 comprises three fixed resistors, with the fourth resistor being the MOS sensor 2445. The output from the Wheatstone bridge circuit passes through an instrumentation amplifier 2525 before going into a multiplexer 2439.

Figure 26:
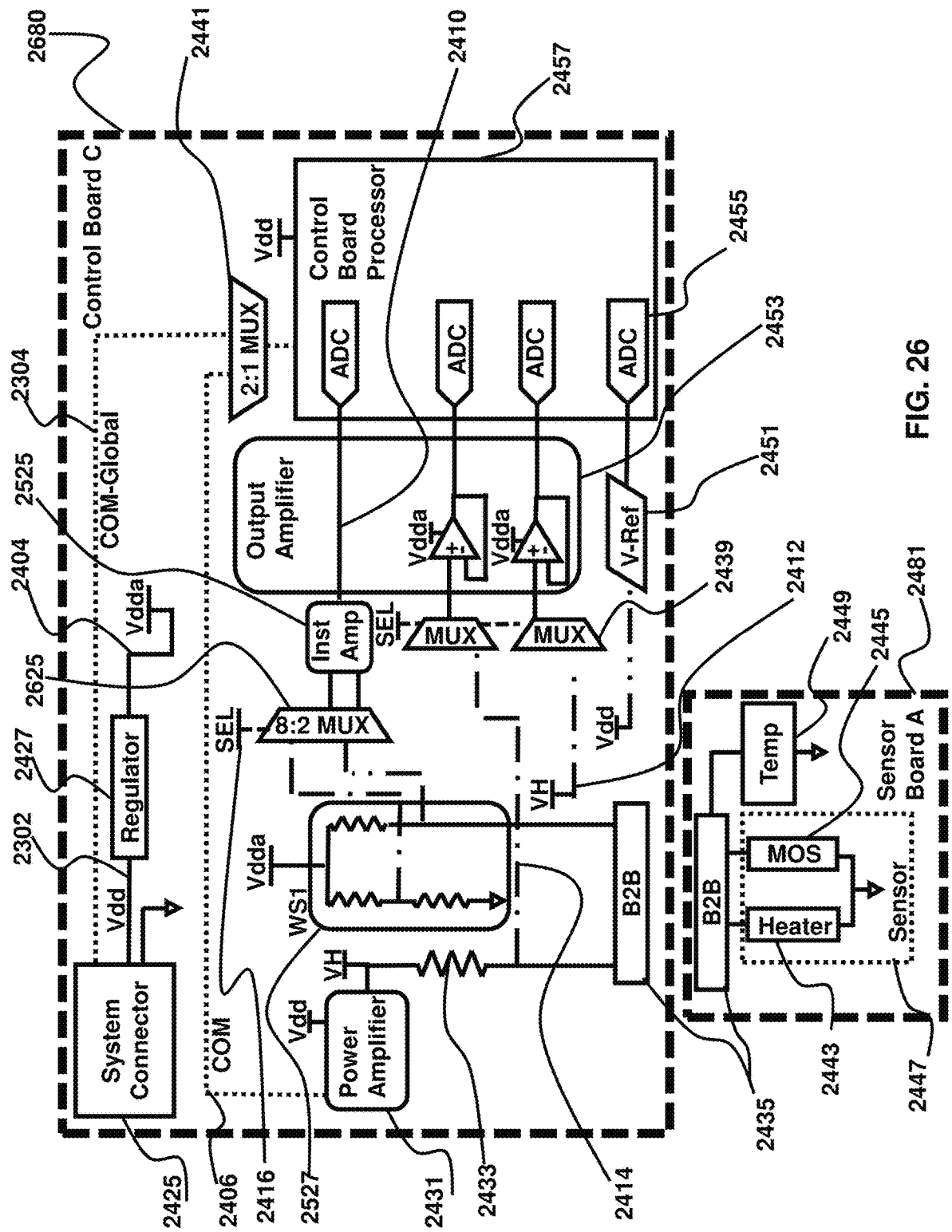
FIG. 26 shows the embodiment of FIG. 25 with a Wheatstone bridge integrity protection feature.

FIG. 26 shows the embodiment of FIG. 25 with a Wheatstone bridge integrity protection feature. This integrity is provided by having a multiplexer with eight pairs of input channels and one pair of output channels 2625 between this Wheatstone bridge 2527 and the instrumentation amplifier 2525. This keeps the current signal from the Wheatstone bridge 2527 protected from the current that maintains the sensor signal integrity.

Figure 27:
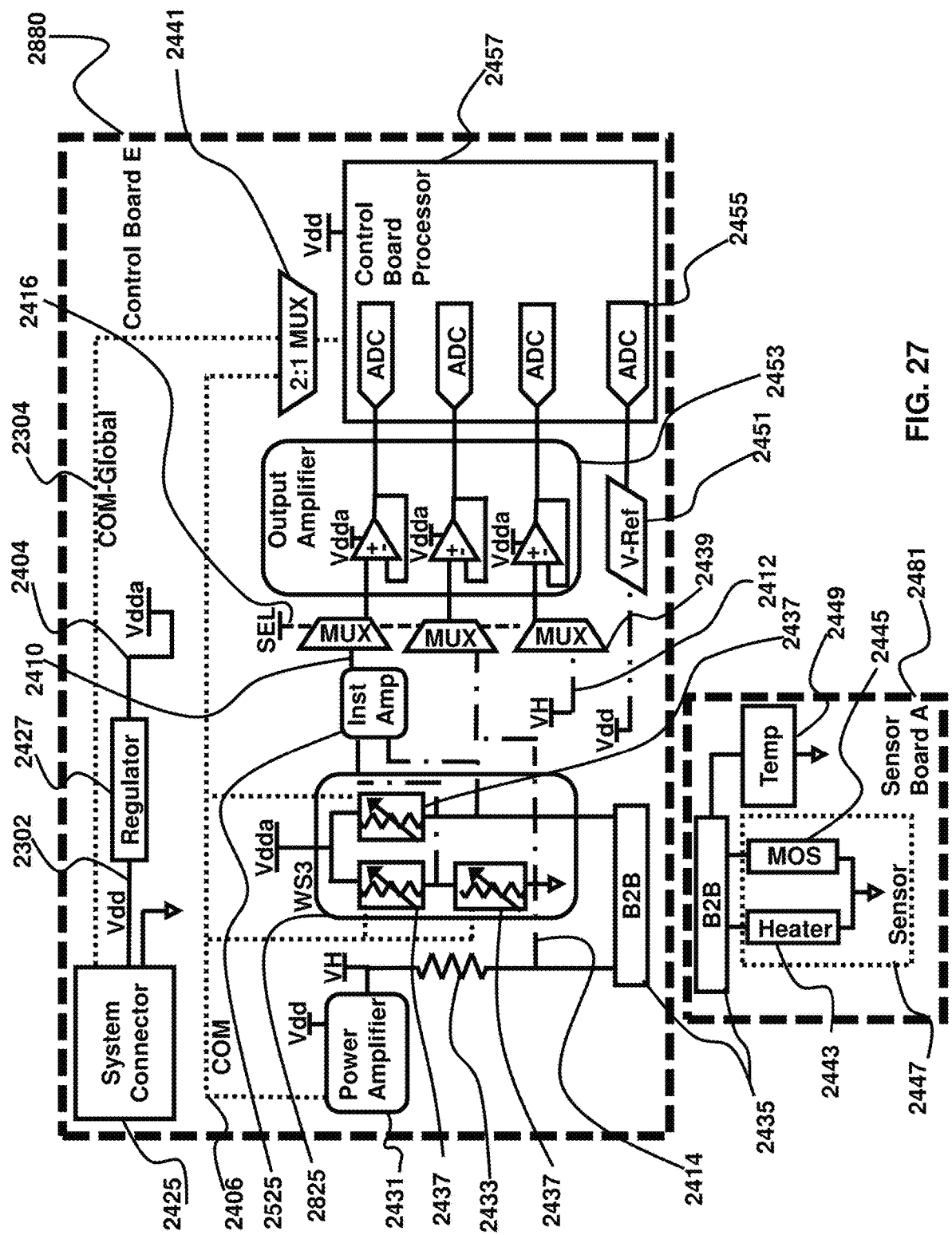
FIG. 27 shows the embodiment of FIG. 25 with the Wheatstone bridge circuit comprising three controlled variable resistors.

FIG. 27 shows the embodiment of FIG. 25 in which the controller board 2880 comprises a Wheatstone bridge circuit, shown at 2825, that comprises three controlled variable resistors, shown at 2437, and the MOS sensor, shown at 2445. The benefit of this arrangement is that the amplification and detection range of the resistance reading of the MOS sensor 2445 can be fully adjustable by changing the resistance values of the controlled variable resistors.

Figure 28:
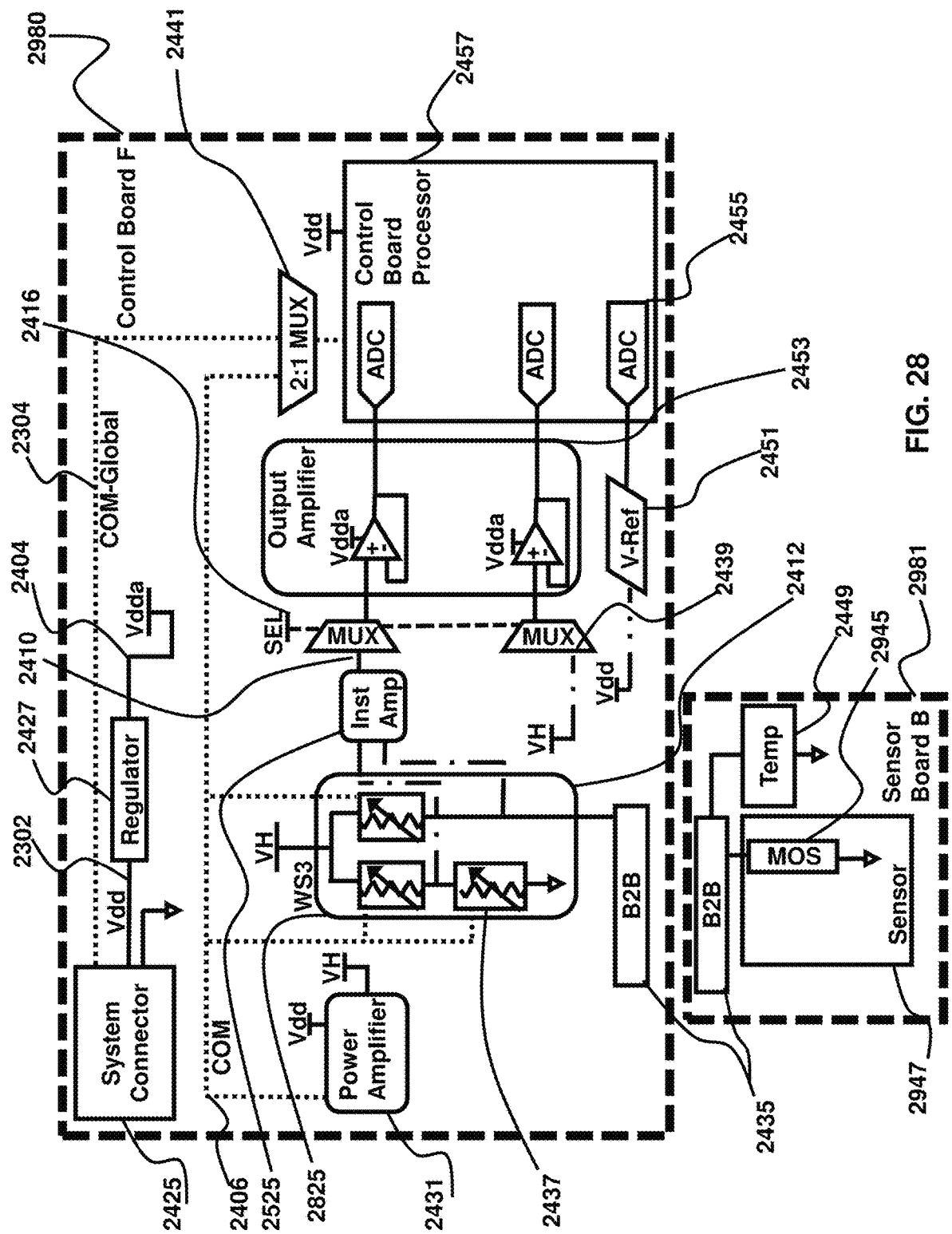
FIG. 28 shows the embodiment of FIG. 27 using an alternate sensor board configured for a two-wire digital metal oxide semiconductor sensor.

FIG. 28 shows the embodiment of FIG. 27 that uses a controller board 2980 for an alternate sensor board 2981 that is configured for a two-wire analog metal oxide semiconductor sensor 2947 that comprises a hot wire metal oxide semiconductor 2945. The principle of operation of these hot wire sensors 2947 is that heating and sensing occurs over the same two-wire circuit element 2945. As shown in FIG. 28, a Wheatstone bridge can be used to respond to changes in resistance of the two-wire circuit element.

Figure 29:
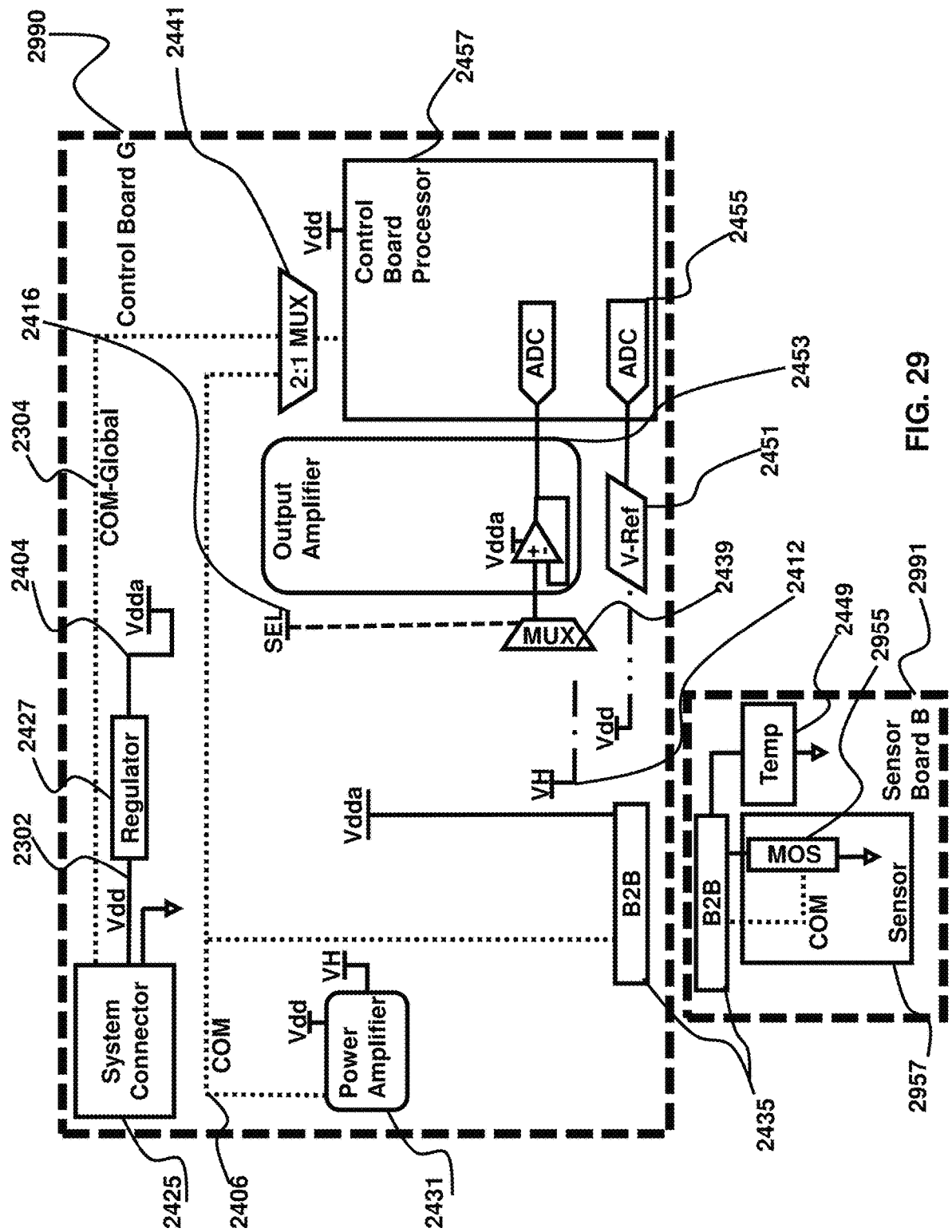
FIG. 29 shows the embodiment of FIG. 27 using an alternate sensor board configured for a two-wire digital metal oxide semiconductor sensor.

FIG. 29 shows an alternate embodiment of FIG. 24 that uses a controller board 2990 for an alternate sensor board 2991 that is configured for a digital metal oxide semiconductor sensor 2957 which comprises a metal oxide semiconductor (MOS) sensing element 2955, analog to digital circuitry, and a digital interface. The principle of operation of these MOS sending elements 2955 is the same as described previously, but the analog sensing of the MOS sensing element 2955 is embedded in the digital MOS sensor 2957. Accessing the resistance value of the MOS sensing element 2955 is done via commands through the digital interface that is connected to the internal communication bus 2406 through the board-to-board connector 2435.

Figure 30:
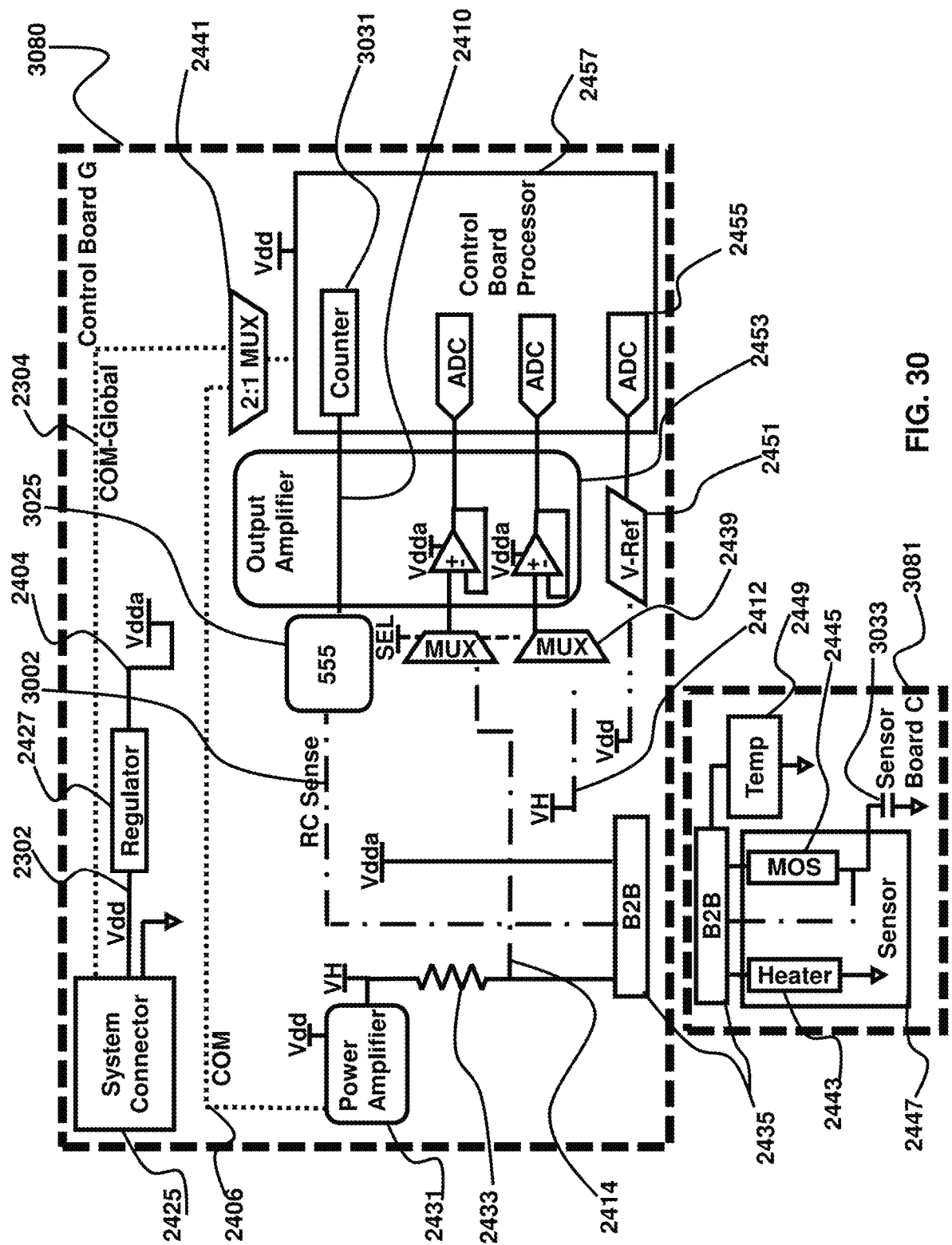
FIG. 30 shows an alternate embodiment of the circuit of FIG. 24 in which an RC (Resistor-Capacitor) circuit is used to generate a digitally timed logarithmic decay.

FIG. 30 shows an alternate embodiment of the circuit of FIG. 24 in which the logarithmic decay of an RC (Resistor-Capacitor) circuit is used to generate a digital output that is proportional to the logarithm of the resistance of a metal oxide semiconductor sensor. For the embodiment shown in FIG. 30, the RC sensor board 3081 comprises the same 4-wire MOS sensor 2447 and temperature sensor 2449 that were shown with reference to FIG. 24, FIG. 25, FIG. 26, and FIG. 27. A fixed capacitor 3033 has been added in series with the metal oxide semiconductor 2445 of the MOS sensor 2447 to produce a voltage divider with a logarithmic response. This logarithmic response is captured as an RC (resistor-capacitor) sense signal 3002 in the control board 3080 for this RC based circuit. This RC sense signal 3002 is fed into a 555 timer 3025 (or equivalent circuit) that generates a digital square wave output as the RC sense signal to reaches a preset value. The length of the square wave is measured by counting the number of clock cycles that have occurred. Those cycles are counted by a counter 3021, and this digital information is used to determine the logarithm of the resistance for the metal oxide semiconductor 2445.

Figure 31:
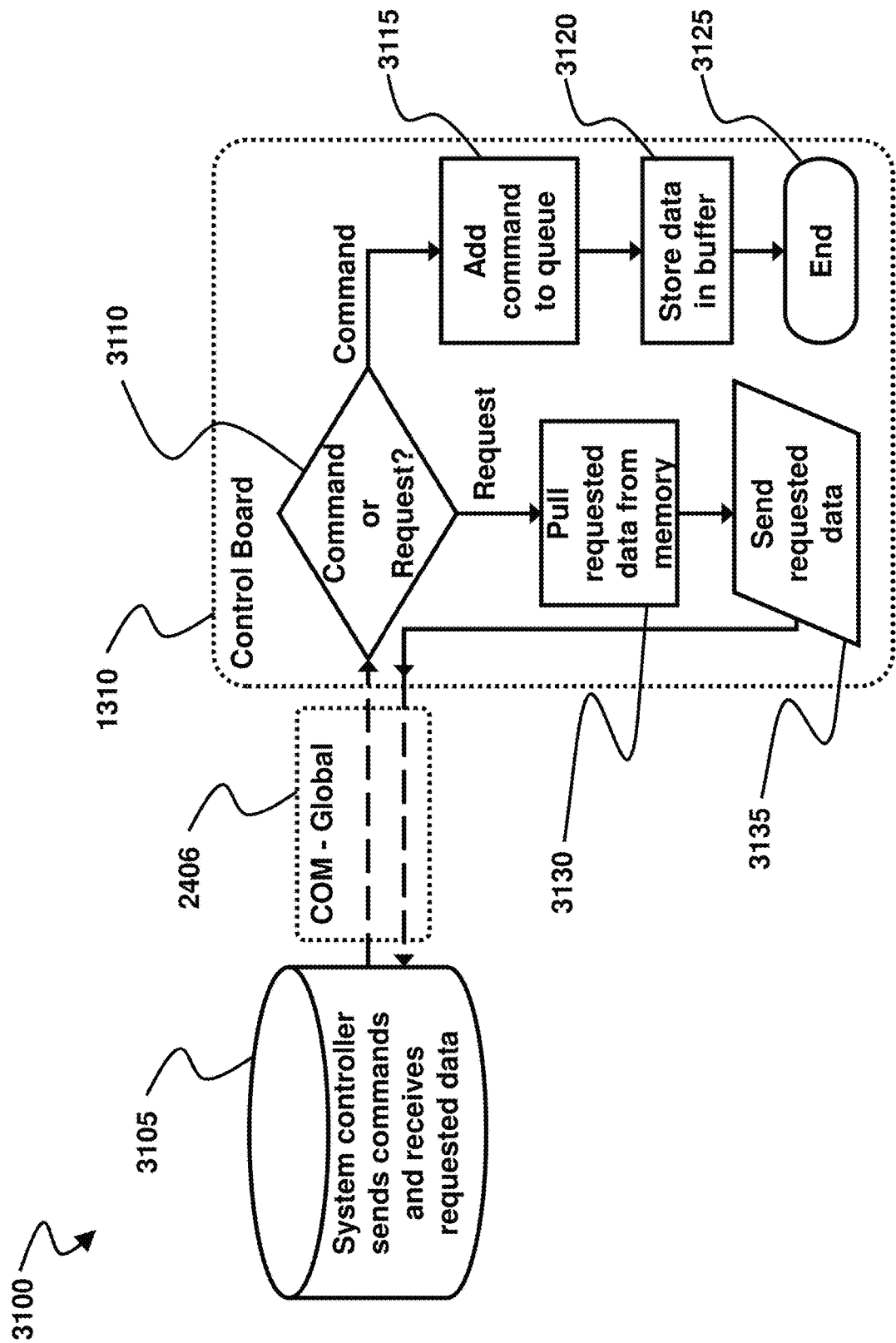
FIG. 31 shows the data flow between the system controller and control board(s) for the system of FIG. 23.

In FIG. 31, the data flow between the system controller and control board(s) 1310 for the system of FIG. 23 is shown at 3100. Generally speaking, the system controller sends commands and receives requested data, as shown at 3105, and this communication occurs over the COM-Global bus, as shown at 2406. The control board(s) 1310 identify whether this is a write command or a read request, as shown at 1310 and execute accordingly. If this is a write command, this command is added to the control board queue 3115, data is stored in a buffer 3120 and the process ends 3125. If this is a read request, the requested data is pulled from memory 3130 and sent to the system controller 3135.

Figure 32:
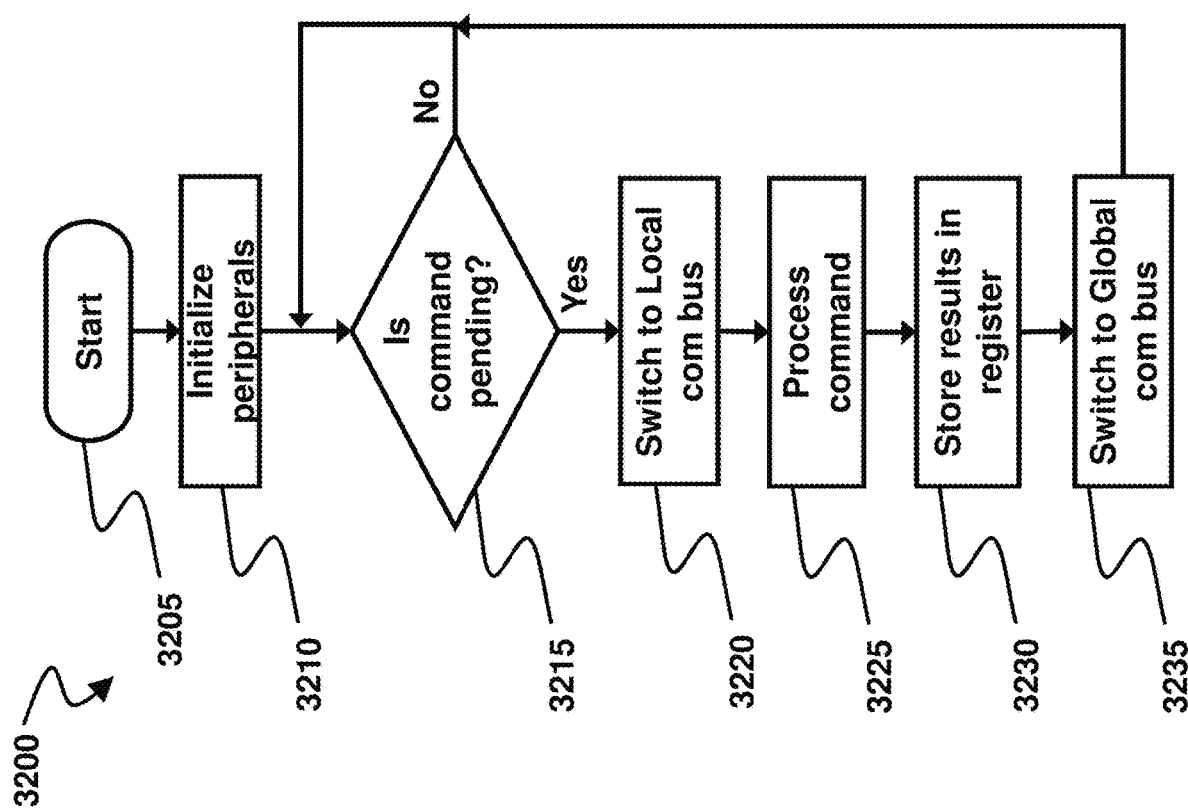
FIG. 32 shows the main process flow for the firmware on the control boards shown in FIG. 24, FIG. 25, FIG. 26, FIG. 27, FIG. 28, FIG. 29, and FIG. 30.

FIG. 32 shows the firmware main process flow 3200 for the control boards of FIG. 24, FIG. 25, FIG. 26, FIG. 27, FIG. 28, FIG. 29, FIG. 30, FIG. 39, FIG. 41 and FIG. 42. When this firmware 3200 is first started 3205, the peripherals are initialized 3210. Then the firmware waits until a command is pending 3215. If a command is pending, attention switches to the local communication bus 3220, the command is processed 3225, the results of this process are stored in a register 3230, and the firmware switches back to the global communication bus 3235 to wait for the next command.

Figure 33:
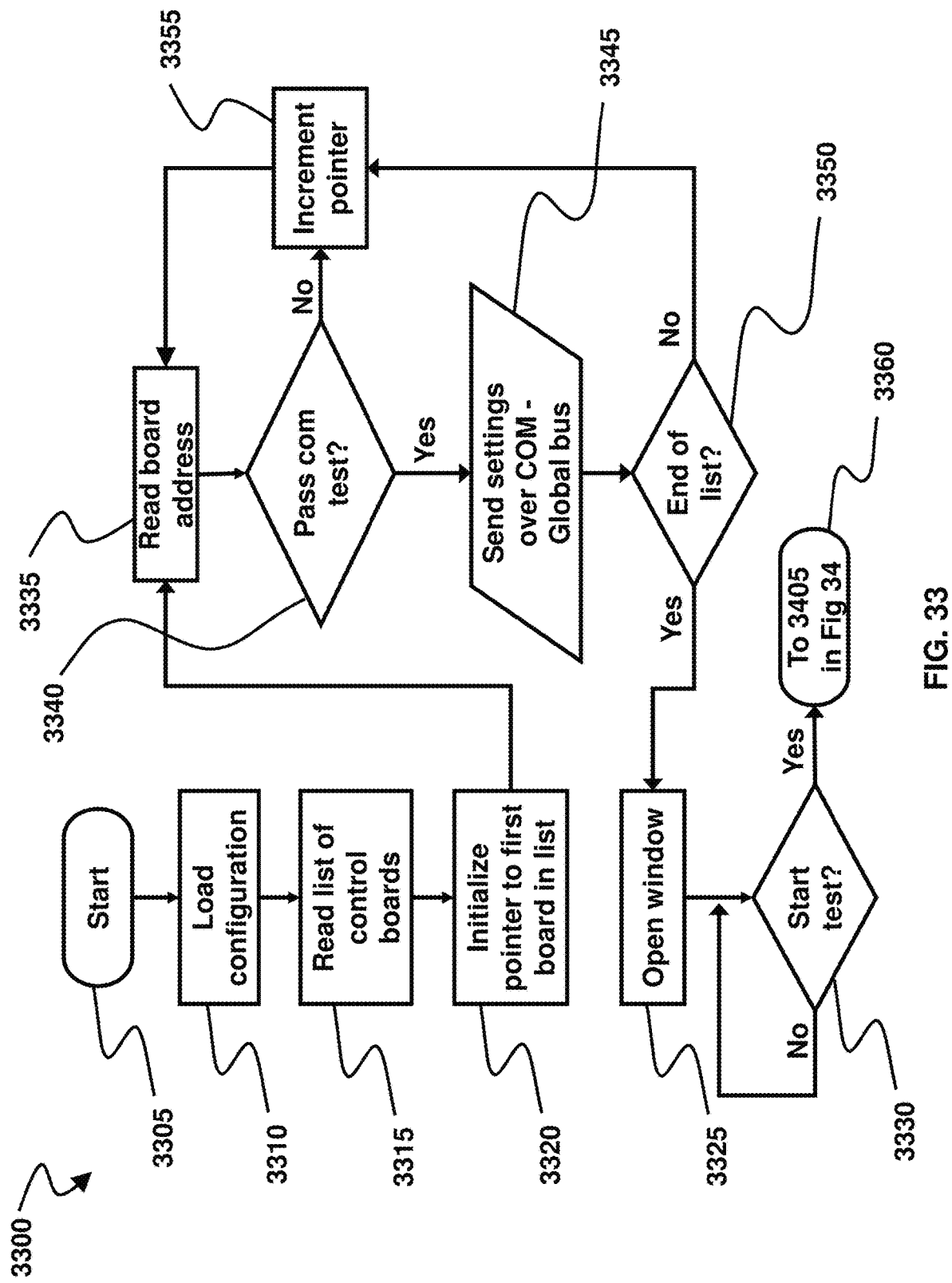
FIG. 33 shows the main process flow for the system controller shown in FIG. 23.

FIG. 33 shows the main process flow for the system controller shown in FIG. 23. When this software is first started 3305, a configuration file that contains details on the operating settings for each control board is loaded 3310. All control boards listed in the configuration file are read into local memory 3315. Starting at the first control board in the list 3320, the communication address is read from the configuration file 3335. Communication to the control board is tested. If the control board responds 3340, all control boards settings are transferred to the control board via the global communication bus 3345. If the control board does not respond, attention switches to the next control board in the list 3355. Steps 3335, 3340, 3345, 3355 are repeated for each control board in the list. Once, the end of the list has been reached 3350, the software displays the graphical user interface on the monitor 3325 and waits for a test to be started 3330. If a test is initiated by the user, the software starts the process shown at 3400.

Figure 34:
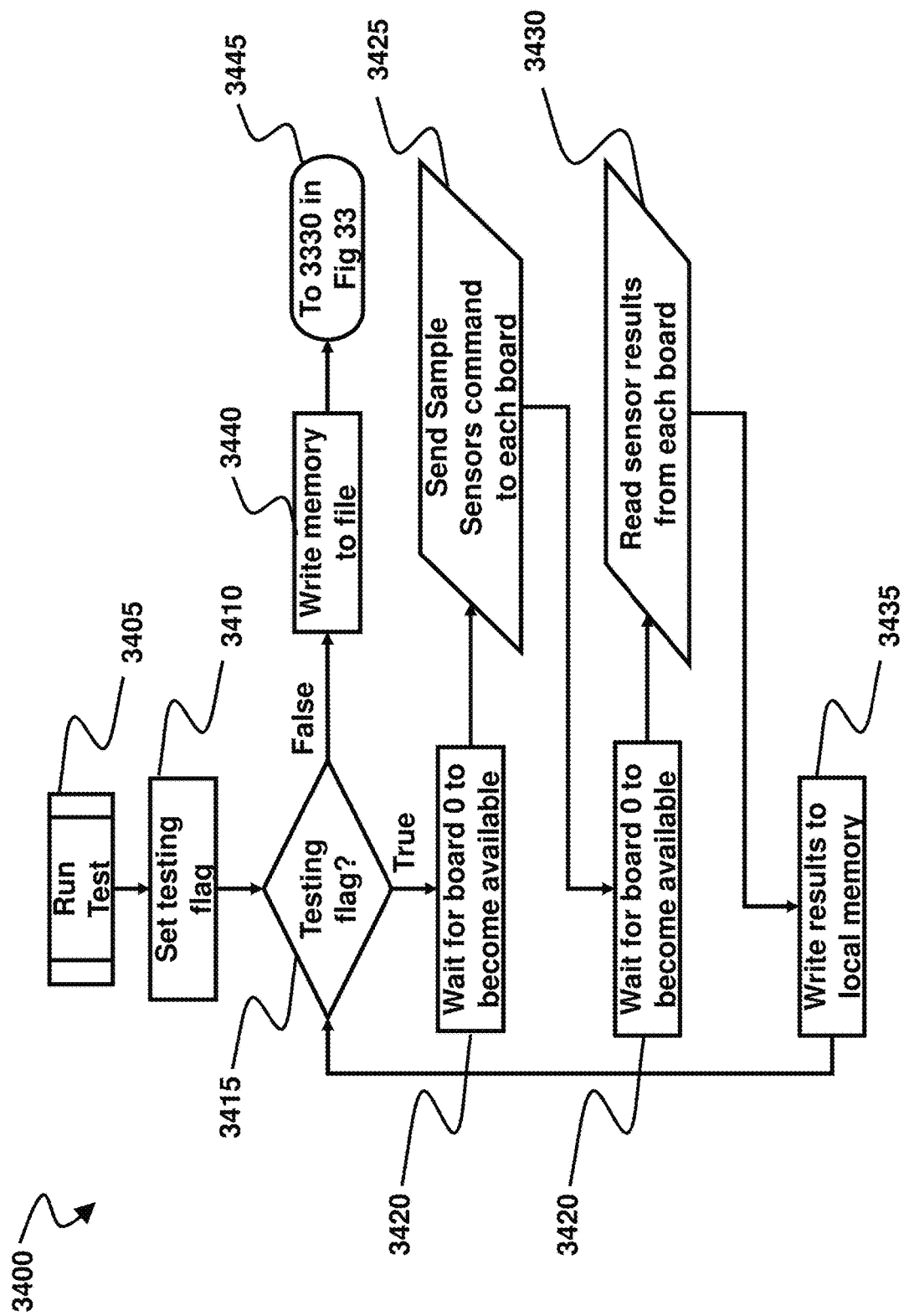
FIG. 34 shows the process flow for the system controller when running a test.

FIG. 34 shows the process flow for the system controller when running a test 3400. This process 3400 starts at 3405, then setting a testing flag 3410 which can be set false by the user via the graphical user interface. Next the testing flag is checked 3415. If the testing flag is true, the software waits for first control board to become available 3420. Once the first control board is ready, the Sample Sensors command is sent to each control board 3425. Next, the software again waits for the first control board to become available 3420. Afterwards, the software requests the sensor results from each control board 3420. All results returned from the control boards are stored into local memory 3435. Steps 3415, 3420, 3425, 3430, 3435 are repeated until the testing flag check 3415 returns false. Then, results stored in local memory are written to a file 3440. After the file has been written, the process returns to step 3330 and awaits another test 3445.

Figure 35:
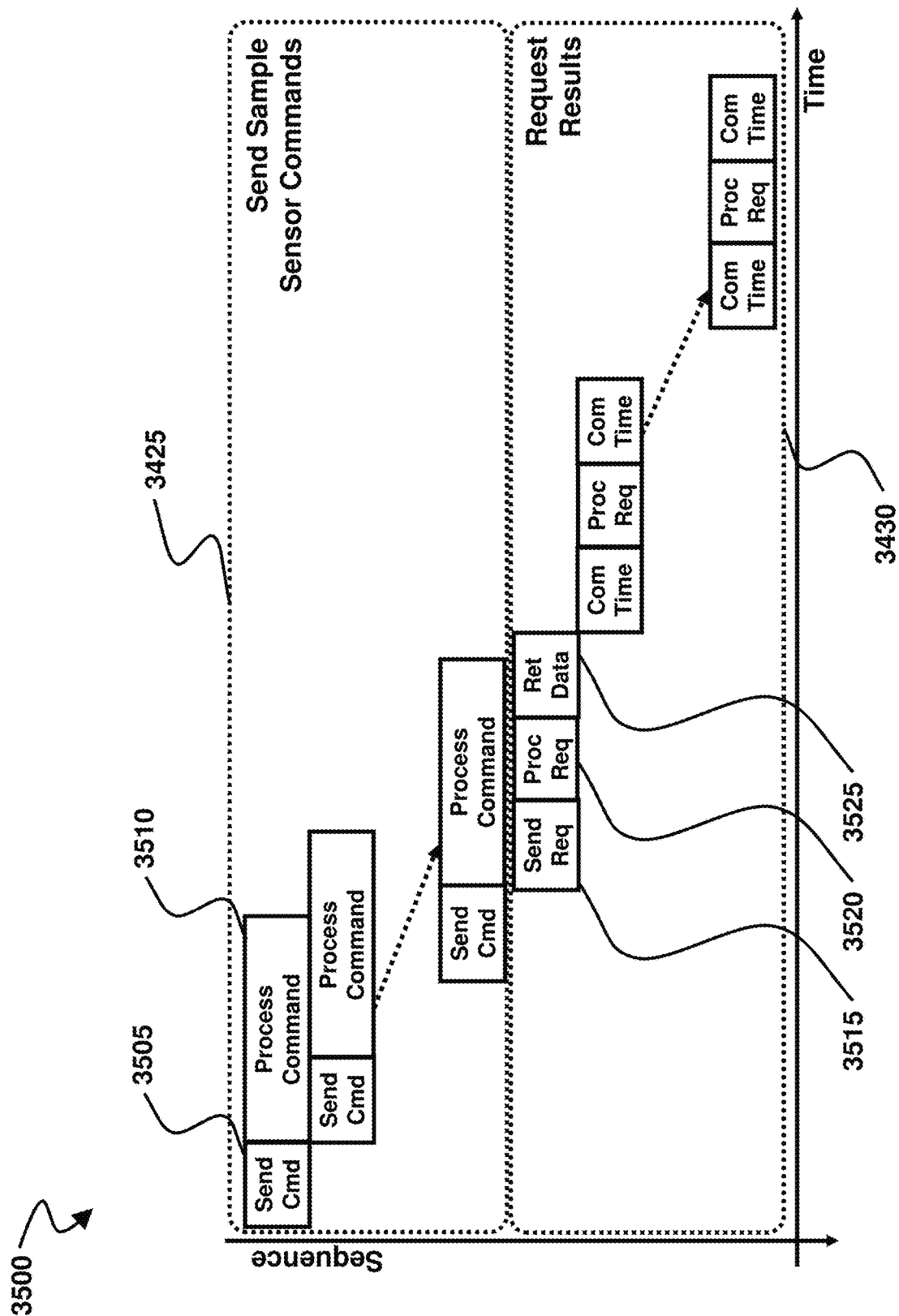
FIG. 35 shows the communication sequence between the system controller and control boards when running a test.

FIG. 35 shows the communication sequence between the system controller and control boards when running a test 3500. In general, the process of sampling and retrieving all sensor results 3500 is broken up into two major sequences Send Sample Sensor Commands 3425 and Request Results 3430. The details of Send Sample Sensor Commands 3425 show a portion of time required to send the command to a single control board 3505 and a portion of time required for that control board to process that command 3510. These steps (3505 and 3510) are repeated for each active control board and sent in a time interleaved fashion. The graph of the Request Results sequence 3430 shows
 (a) the portion of time needed to send the request to the control board 3515;
 (b) the portion of time for the control board to pull the requested result from local memory 3520; and
 (c) the portion of time for the control board to send results back to the system controller 3525.

These steps are repeated for each active control board and processed in a serial fashion.

Figure 36:
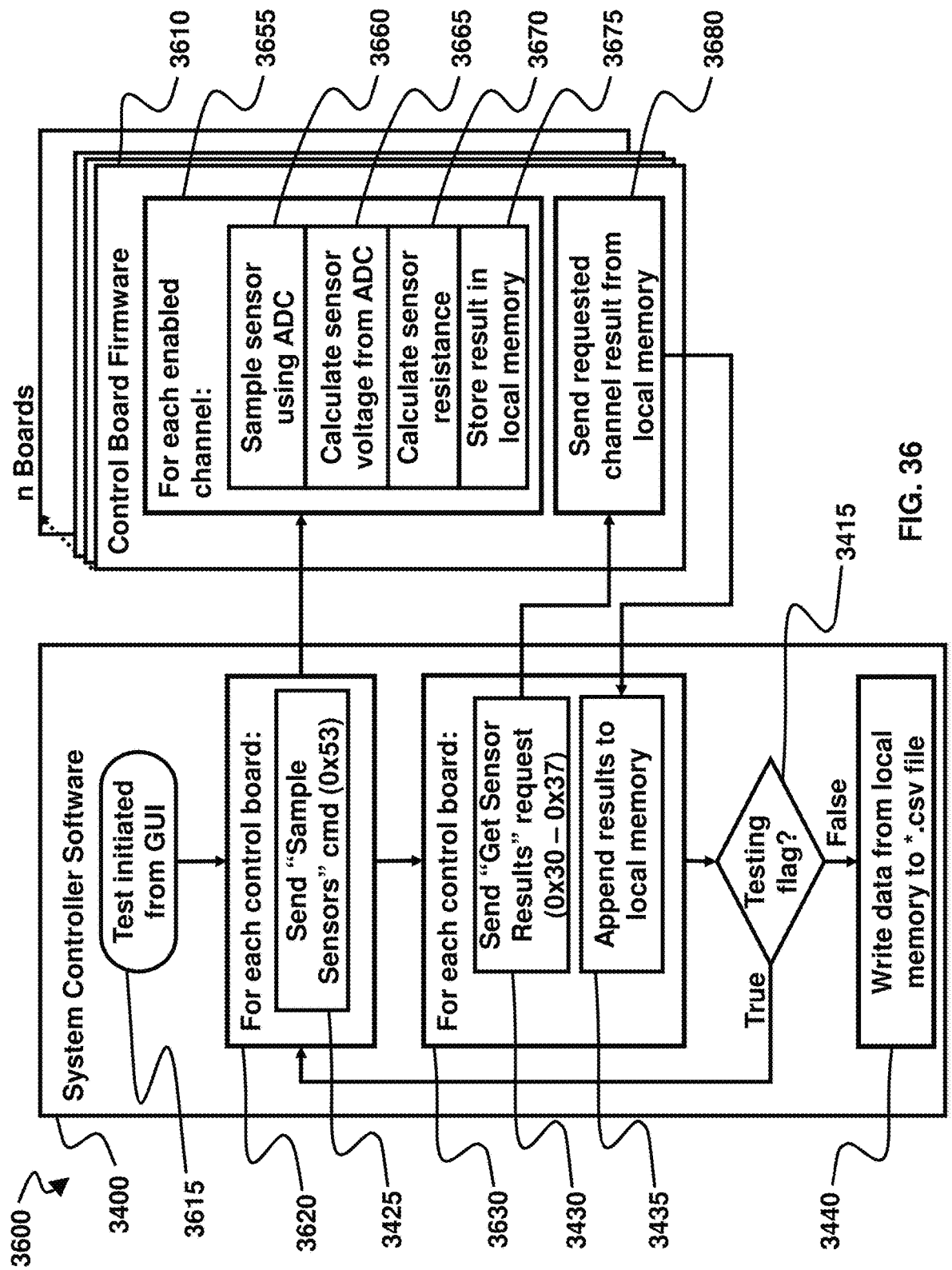
FIG. 36 provides an overview of how data from the system of FIG. 23 is processed.

FIG. 36 provides an overview of how data from the system of FIG. 23 is processed. First, a test is initiated via the graphical user interface 3615. Next, the Sample Sensors command 3425 is sent to each control board 3620 as described in FIG. 35. The control board firmware 3610 processes the command for each enabled sensor channel 3655. The Sample Sensors command first uses the analog to digital converter to obtain a binary value representing the ratio of sensor voltage relative to the supply voltage on a scale of $2^{nbits}$ 3660. Where nbits is the resolution of the ADC. Using the obtained ADC value, the sensor voltage is calculated 3665, then the sensor resistance is calculated 3670. After resistance is calculated for a given channel, the result is stored in local memory in the control board. 3675. After software sends Sample Sensor commands to all control boards, it then requests the results from each control board 3630. The sensor results for a given control board can be requested by sending a Get Sensor Results request 3430. The control board firmware responds by pulling the requested result from local memory and sending it back to the software running on the system controller 3680. The software appends each result in local memory. Steps 3620 and 3630 are repeated until the testing flag check 3415 returns false. Once the testing flag is false, the results in local memory are written to a file 3440.

Figure 37:
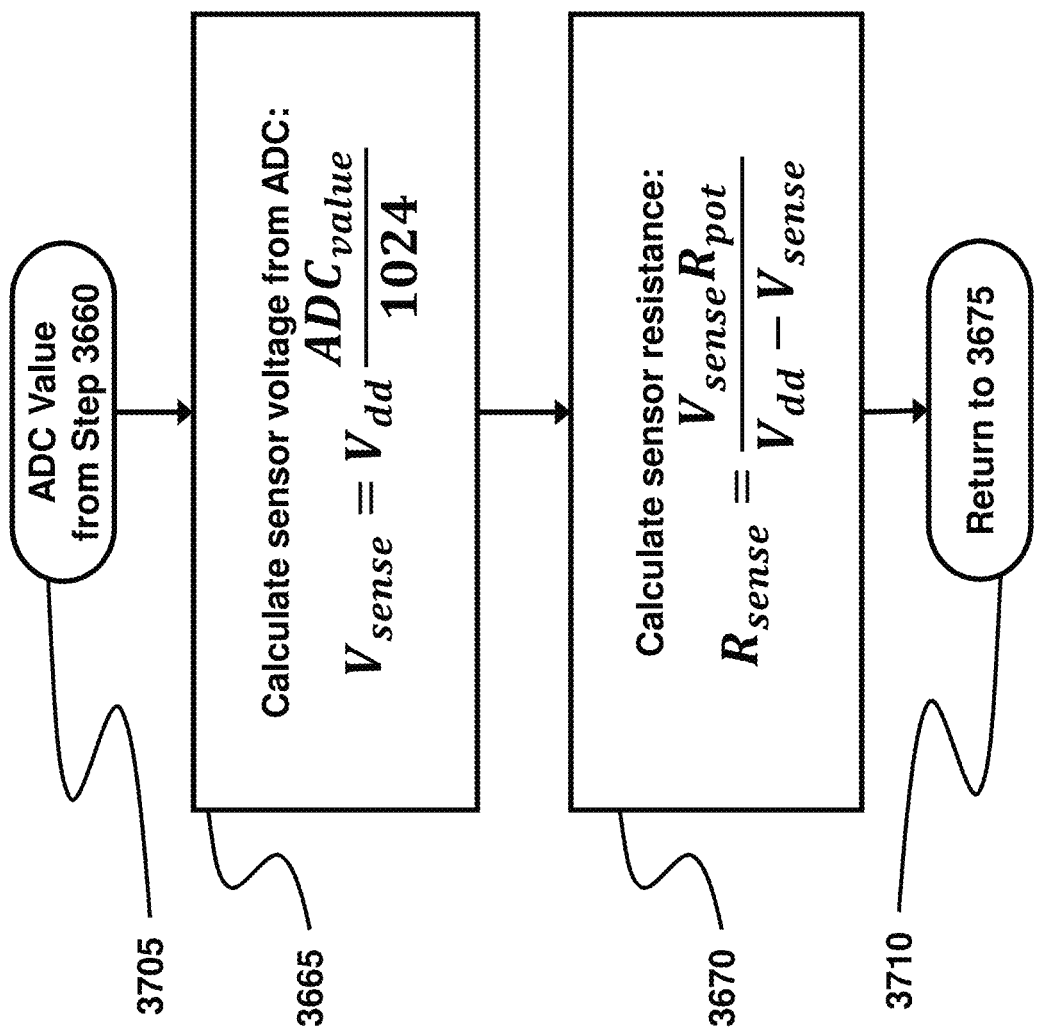
FIG. 37 details the conversion calculation of step 3670 in FIG. 36.

FIG. 37 details the conversion calculation of step 3670 in FIG. 36 by using an example ADC (analog to digital conversion) with 10 bits of resolution. First, sensor voltage (Vsense) is calculated by dividing the ADC value by 1024 ($2^{10}$), and multiplying by the supply voltage (Vdd) 3665 as shown by the following formula:

$$V_{sense} = V_{dd} \frac{ADC_{value}}{1024}$$

Next, sensor resistance (Rsense) is calculated by multiplying Vsense and potentiometer resistance (Rpot) and then dividing by supply voltage (Vdd) minus Vsense, as shown by the following formula:

$$R_{sense} = \frac{V_{sense} R_{pot}}{V_{dd} - V_{sense}}$$

Finally, at step 3710, the process returns to step 3675 in FIG. 36.

Figure 38:
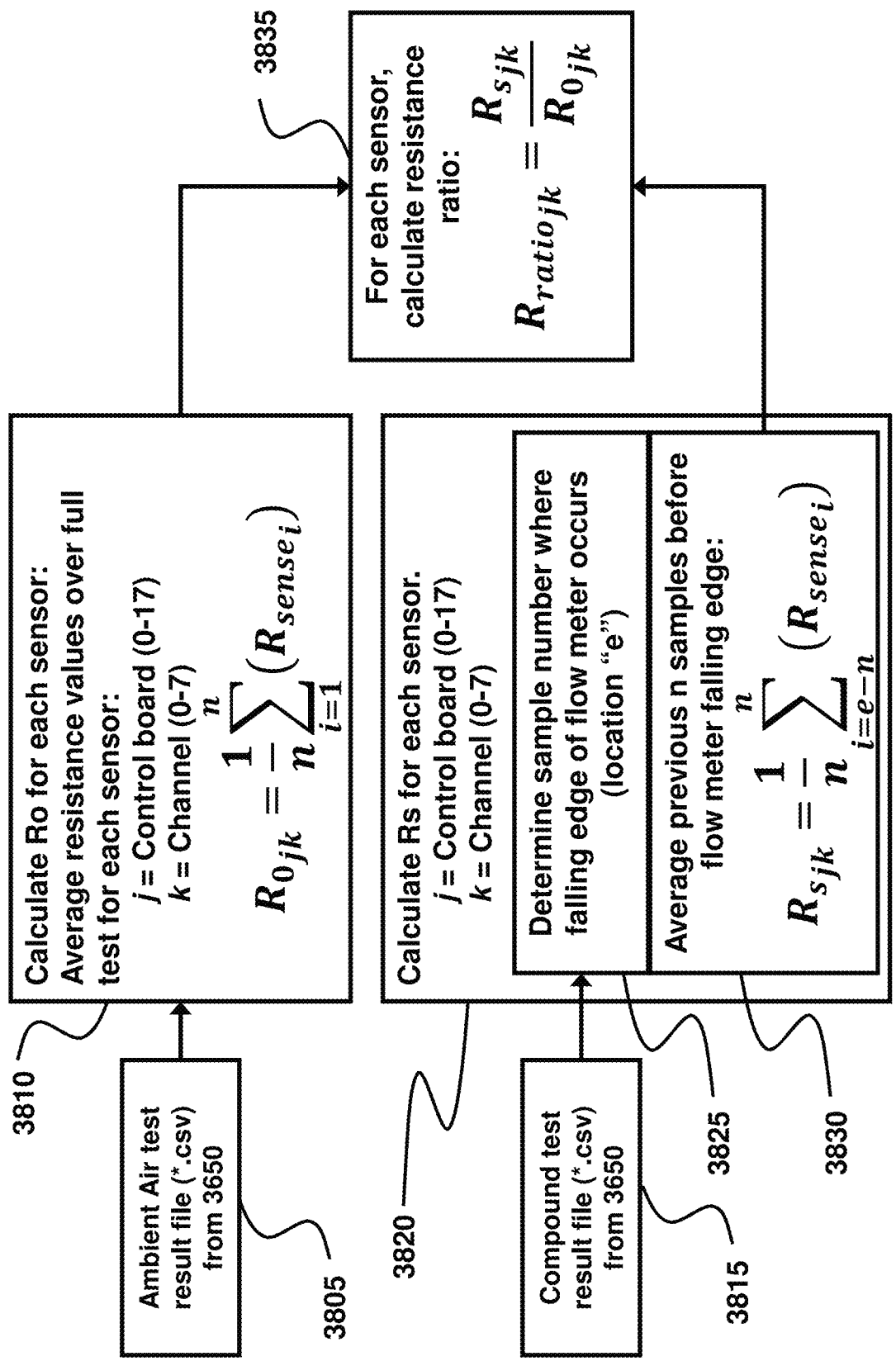
FIG. 38 shows the post-processing calculations that occur when converting resistance ratios as shown in FIG. 36 and FIG. 11.

FIG. 38 shows the post-processing calculations that occur when converting resistance ratios as shown in FIG. 36 and FIG. 11. This requires the results file from an ambient air sample 3805, and a results file from a specimen sample (isolated compound, breath, urine headspace, or feces headspace) 3815. The reference resistance of a given sensor (Ro) is calculated by averaging each sensor's resistance over all samples 3810 as shown by the following formula:

$$R_{0_{jk}} = \frac{1}{n} \sum_{i=1}^{n} (R_{sense_i})$$

The sensor resistance when exposed to the sample (Rs) is calculated by first finding where the flow through the system ends, marked by location "e" in calculations 3825. Next, a subset of n samples from location "e" are averaged for each sensor 3830 as shown by the following formula:

$$R_{s_{jk}} = \frac{1}{n} \sum_{i=e-n}^{n} (R_{sense_i})$$

Finally, the ratio of Rs/Ro is calculated for each sensor 3835 as shown in the following formula:

$$R_{ratio_{jk}} = \frac{R_{s_{jk}}}{R_{0_{jk}}}$$

Figure 39:
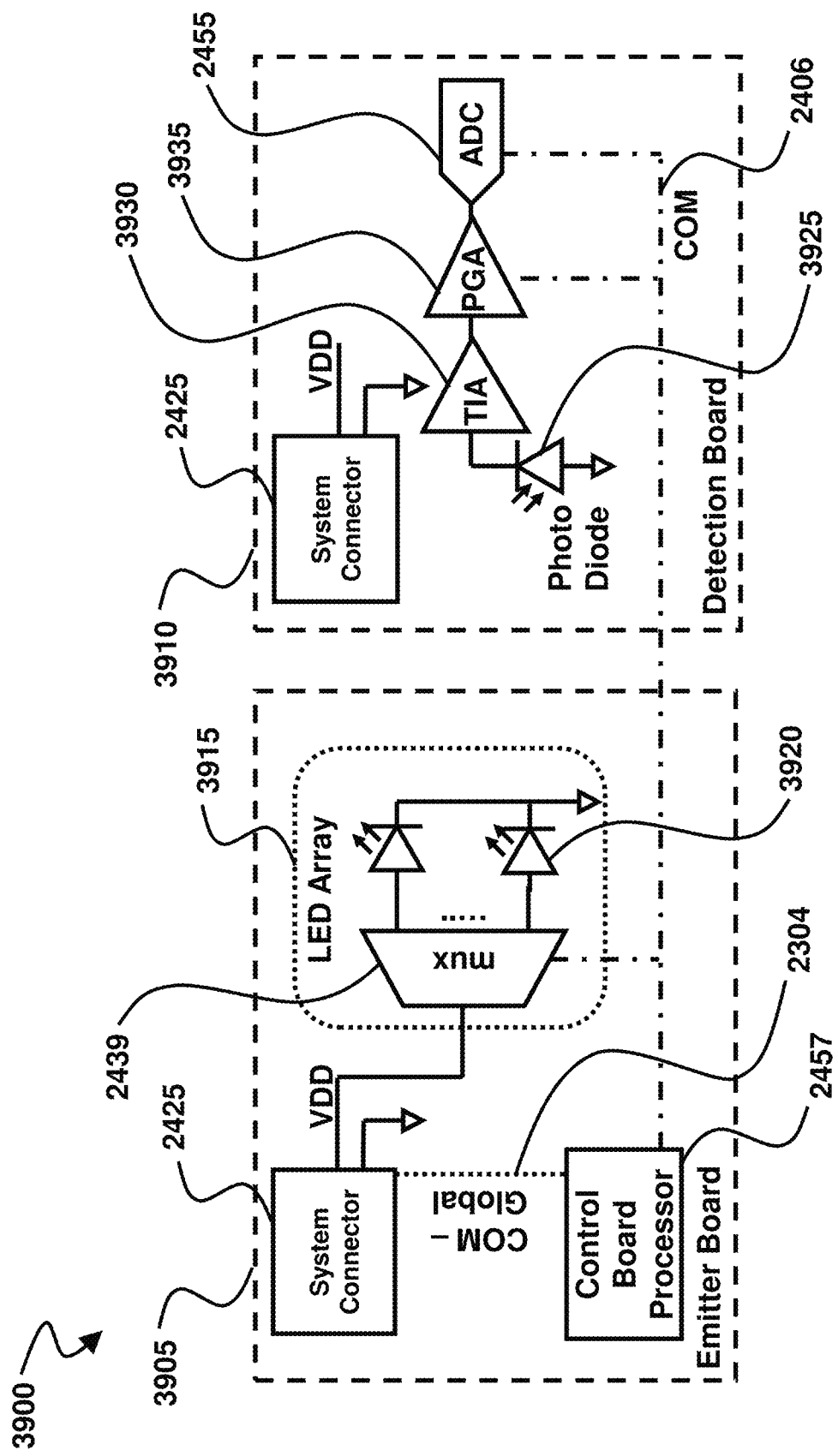
FIG. 39 shows an infrared (IR) absorption spectroscopy circuit that can be used in embodiments of the invention.

Referring to FIG. 39, the infrared (IR) absorption spectroscopy gas sensor system shown at 3900 is an alternative to the control boards that were shown in FIG. 24 to FIG. 30. This IR spectroscopy system 3900 comprises an emitter board 3905 and a detection board 3910. The emitter board (3905 in FIG. 39) is configured to connect to the system processor (2331 in FIG. 23) through the same communication bus 2304 and sensor chamber bus board 2339 that were shown in FIG. 23 using the system connector 2425 that was shown in FIG. 24 to FIG. 30. The emitter board 3905 comprises an array of LEDs (light emitting diodes) shown at 3915 and this LED array 3915 comprises a plurality of LEDs 3920 and a multiplexer 2439. A control board processor 2457 on the emitter board 3905 managed the emitter board 3905 and detection board 3910. The detection board 3910 also comprises a system connector 3910 and a photodiode for measuring the light from the LED array 3915 as it passes through the gases in the sensor chamber, 1300 in FIG. 14. Some of the wavelengths emitted by the LED array 3915 will be absorbed by the gases in the sensor chamber, which indicates the presence and concentration of specific gaseous compounds. This photodiode 3925 output is then passed through a trans-impedance amplifier (TIA) 393 and a programmable gain amplifier (PGA) 3935 before the resulting analog signal is converted to a digital signal by an analog to digital converter (ADC) 2455, which can then be read by the control board processor 2457.

Figure 40:
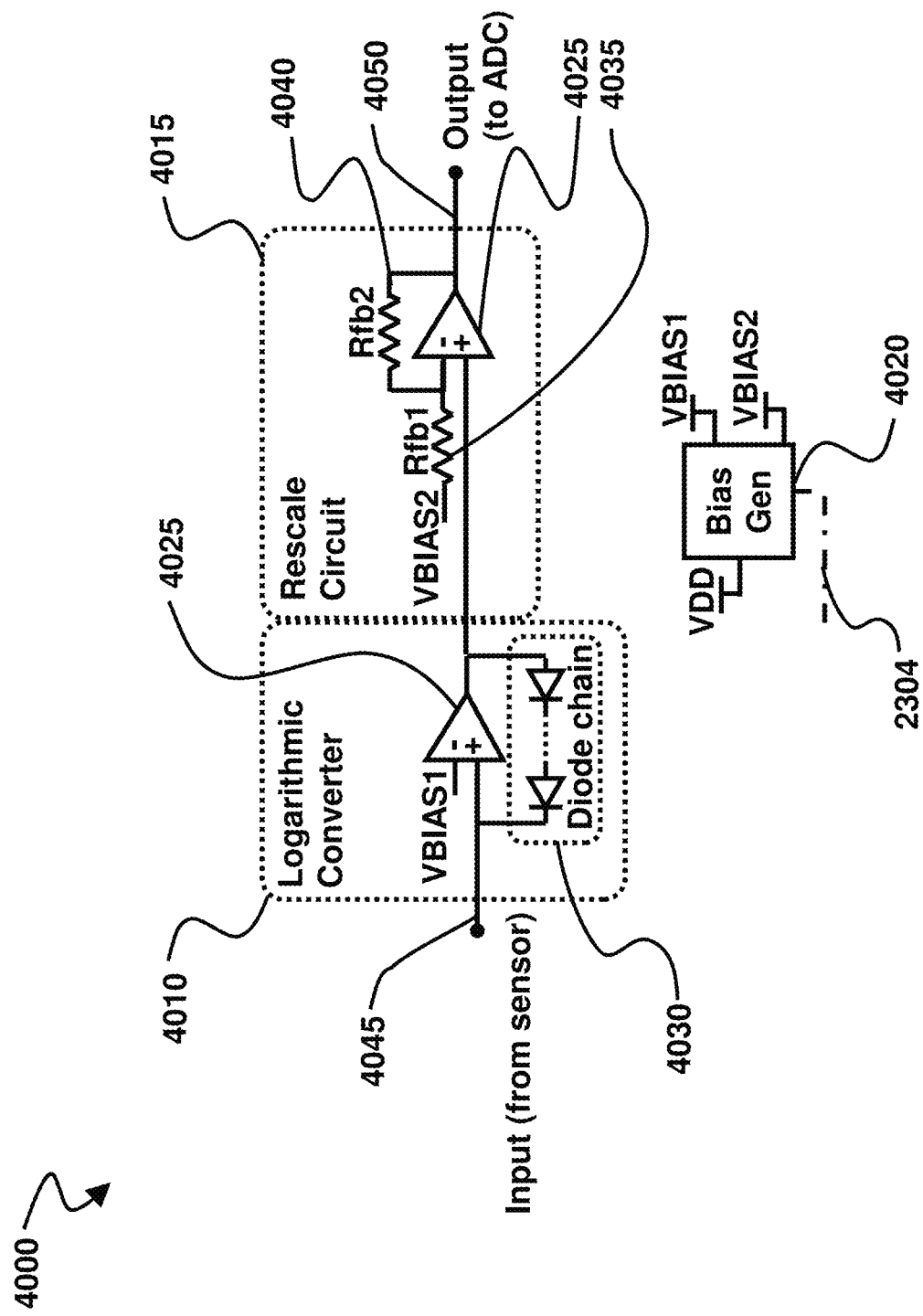
FIG. 40 shows a logarithmic amplifier that can be used in embodiments of the invention.

Referring to FIG. 40, the logarithmic amplifier shown at 4000 has been designed to convert an analog input signal from a sensor 4045 into an output signal 4050 that is the logarithm of that input signal 4045. This can be accomplished by using a logarithmic converter shown at 4010 and a rescale circuit shown at 4015. The logarithmic converter comprises an operational amplifier 4025 with a diode chain 4030 between the output and the non-inverting input, which has the analog input signal 4045 connected to it. Note that, the diode chain 4030 must be at least one diode long. There are tradeoffs in choosing the number of diodes in the range of output voltages produced. It is also dependent on the exact model of diode used. Diodes can be implemented using discrete devices, MOSFETs, BJTs, or other semiconductor devices. The inverting input of the operational amplifier 4025 is connected to a first VBIAS signal from a bias generation circuit 4020 that is controlled by the internal communication bus 2406. A bias voltage is considered to be any voltage level that is not supply or ground that us used to enable active devices to operate properly. Bias voltages not only ensure the connected circuitry is operating in the correct voltage ranges, but also offer further adjustability to circuit output. A bias voltage can be implemented in many ways including voltage division, one or more diodes, the use of an DAC (digital to analog converter), and/or any combination of the above or any other technique capable of being understood by anyone skilled in the art. The output of the logarithmic converter 4010 is then fed into the non-inverting input of an operational amplifier 4025 in the rescale circuit 4015 where it is adjusted based on the use of a second VBIAS signal applied to feedback resistors 4035 and 4040 that connect the output signal 4050, the inverting terminal of the operational amplifier and the second VBIAS signal in the configuration shown in FIG. 40.

Figure 41:
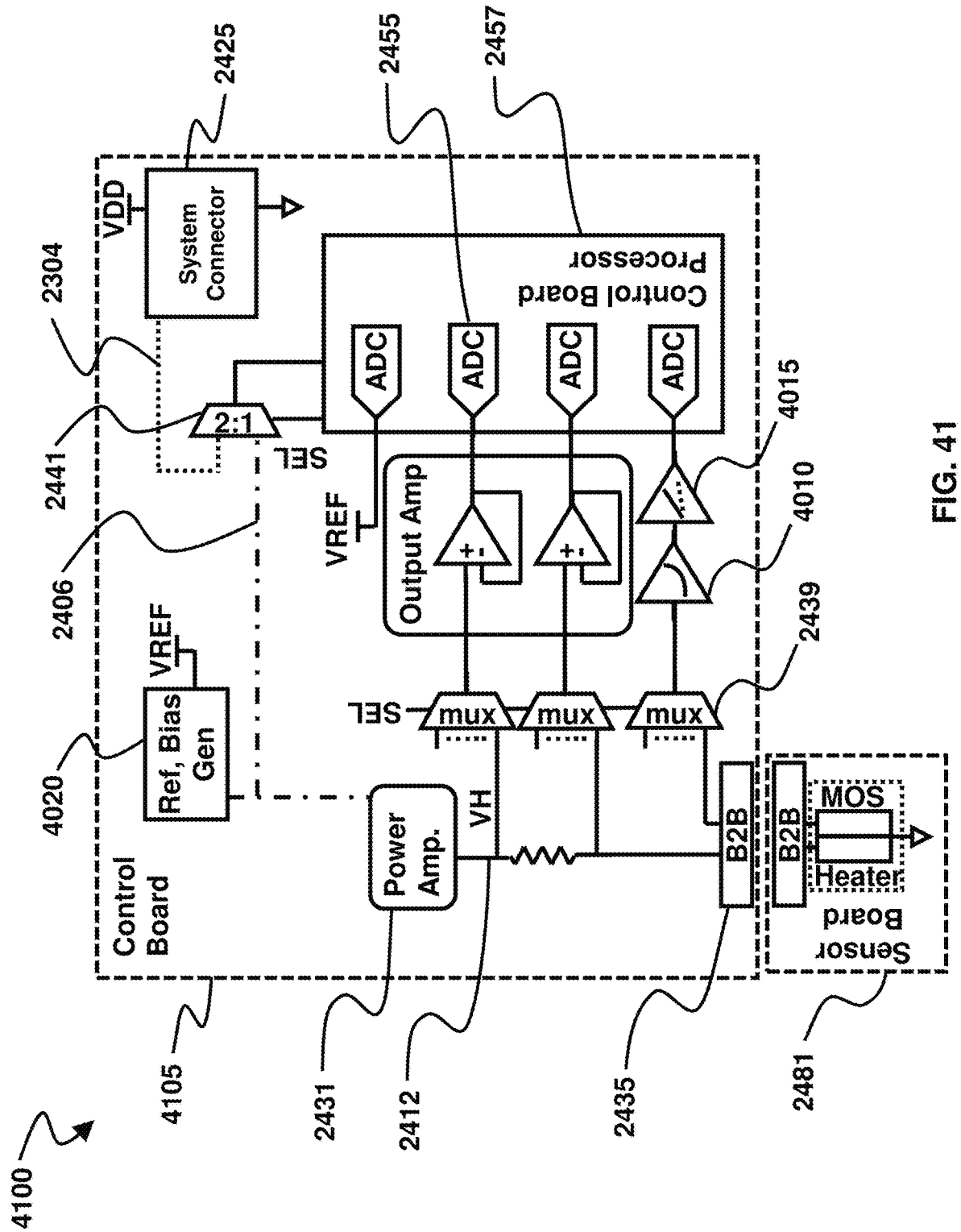
FIG. 41 shows a logarithmic output circuit that uses the logarithmic amplifier shown in FIG. 40 and can be used in embodiments of the invention.

FIG. 41 shows control board that is an alternative embodiment to the control boards that were shown in FIG. 24 to FIG. 30, and FIG. 39. This control board 4105 is configured to work with the same sensor boards for 4-wire sensors 2481 that were shown and detailed with reference to FIG. 24 to FIG. 27 having many components with similar numbers that were described previously with reference to these figures. The primary difference is that the logarithmic amplifier system shown at 4100 will generate a digital output that is the logarithm of the resistance of the metal oxide semiconductor (MOS) in the sensor board 2481 instead of a linear measurement of this resistance. This is accomplished through the use of the logarithmic converter 4010 (detailed in FIG. 40) and rescale circuit 4015 (detailed in FIG. 40) as shown in FIG. 41.

Figure 42:
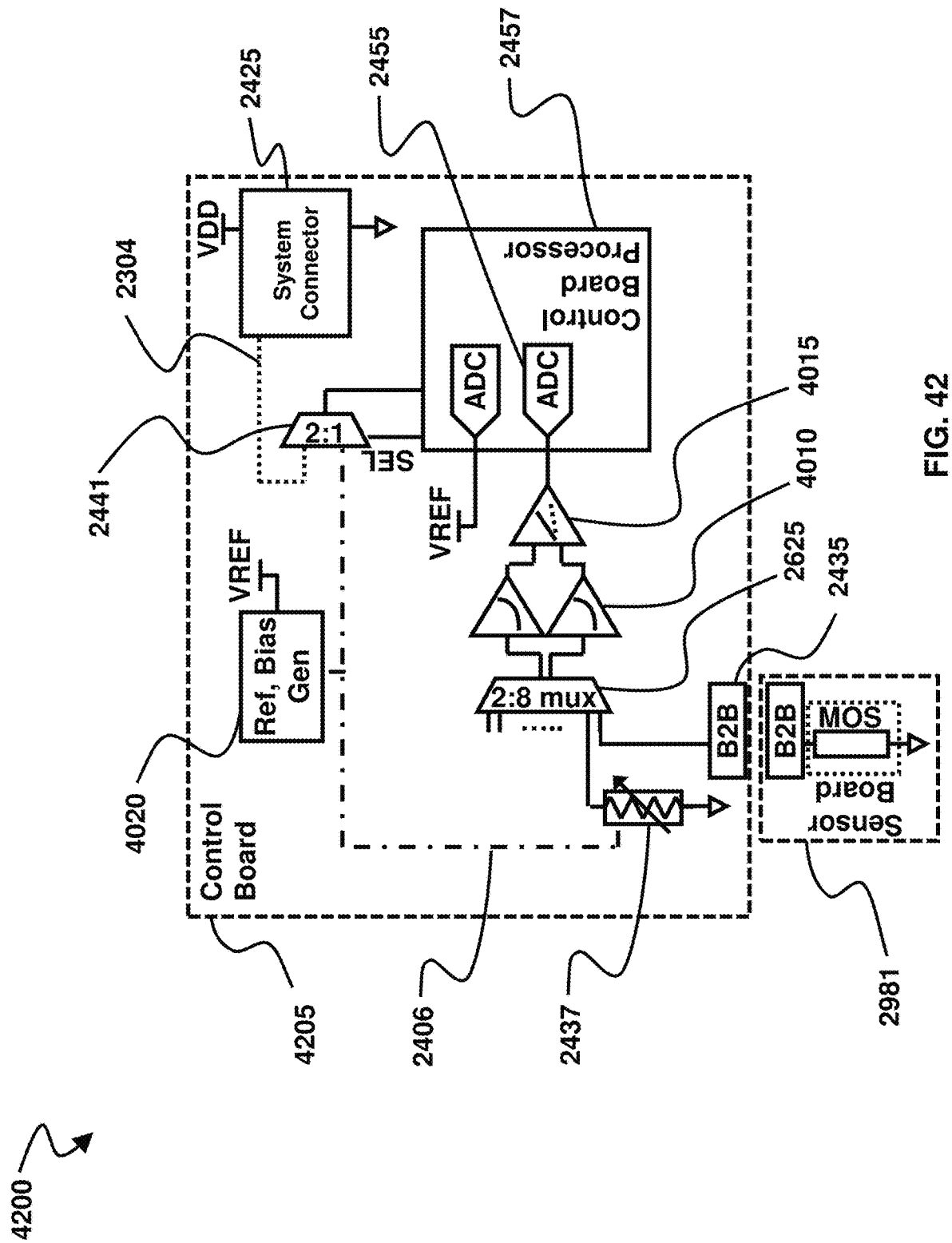
FIG. 42 shows a differential logarithmic output circuit that uses the logarithmic amplifier shown in FIG. 40 and can be used in embodiments of the invention.

FIG. 42 shows another embodiment of differential logarithmic output circuit at 4200 that comprises a differential logarithmic control board 4205 configured for reading a sensor board for a 2-wire sensor 2981 that was previously shown with reference to FIG. 28. In this case, the outputs from the sensor are isolated using a multiplexer with eight pairs of input channels and one pair of output channels 2625 to accomplish the same functions that were described with reference to FIG. 26. The outputs of this multiplexer 2625 are then applied to a pair of logarithmic converters 4010 described previously in FIG. 40 and the outputs of these logarithmic converters are then fed into a rescale circuit 4015 before being converted to a signal by an analog to digital converter 2455. Other elements of the differential logarithmic output circuit 4200 are similar to like numbered elements in previous figures.

Figure 43:
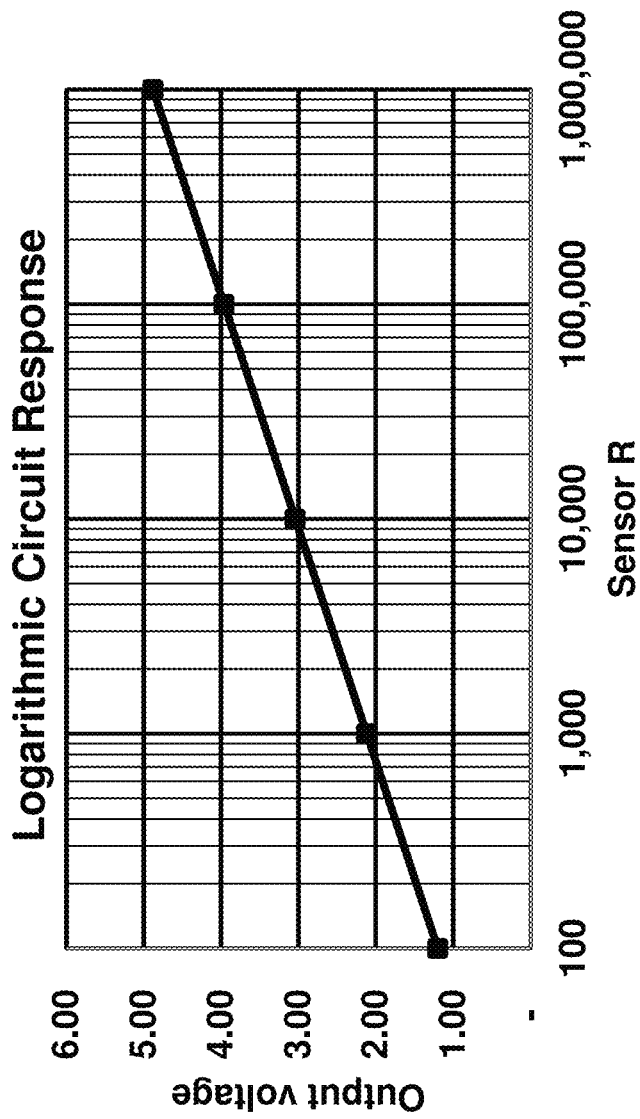
FIG. 43 shows the circuit response of the logarithmic circuit of FIG. 40, FIG. 41, and/or FIG. 43.

FIG. 43 shows the circuit response of the logarithmic circuit of FIG. 40, FIG. 41, and/or FIG. 43. Note the linear response to a wide range of sensor resistances without the need of dynamic adjustments.

Figure 44:
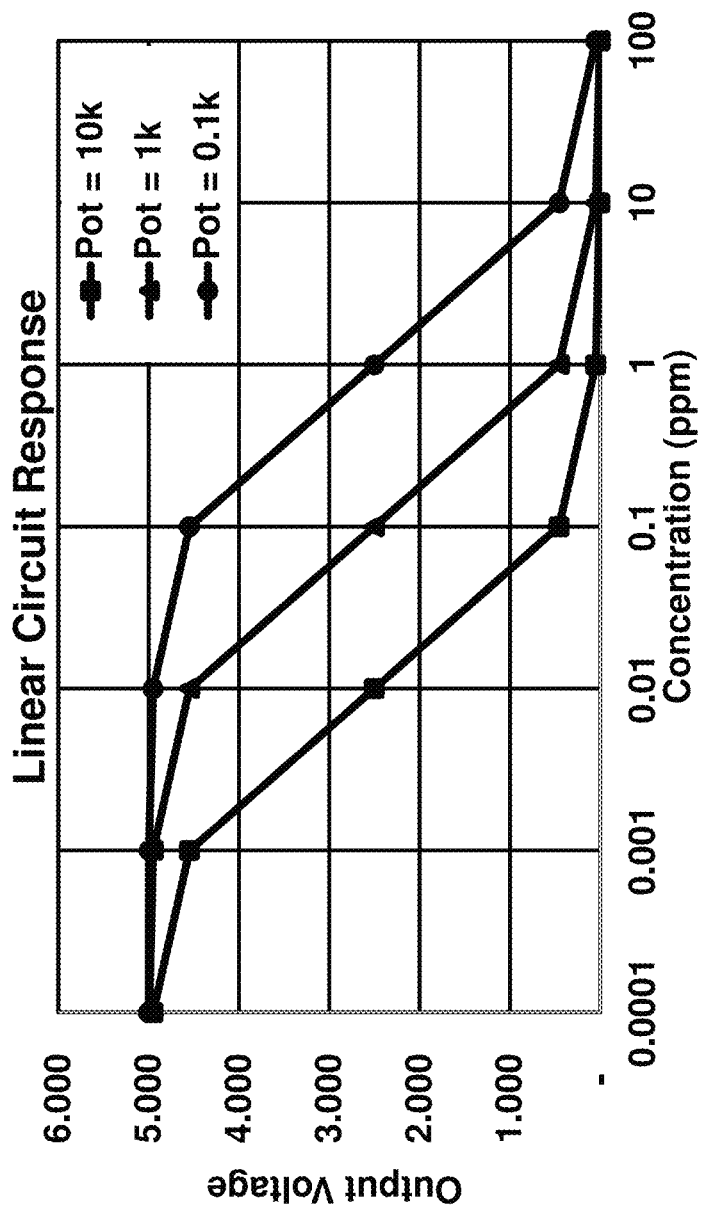
FIG. 44 shows how the controlled variable resistors can be used to improve the dynamic range of concentrations that can be measured by embodiments of the invention.

FIG. 44 shows how the controlled variable resistors can be used to improve the dynamic range of concentrations that can be measured by embodiments of the invention. The traditional voltage division circuit suggested by MOS sensor manufacturers is limited in the range where the response remains linear. Therefore, the auto ranging feature automatically adjusts the circuit so it remains in an ideal operating region.

A number of variations and modifications of the disclosed embodiments can also be used. Although only simplified systems and methods have been illustrated and described herein, it can be understood that the systems and methods shown and described can be scaled up to incorporate a greater number of elements, a greater number of tests of various gases, a greater number of human subjects and other combinations and variations capable of being understood by anyone skilled in the art. While the principles of the disclosure have been described above in connection with specific apparatuses and methods, it is to be clearly understood that this description is made only by way of example and not as limitation on the scope of the disclosure.

We claim:
1. An electronic nose for determining a health status, the electronic nose comprising:
  a collection module configured for receiving an air sample emitted by a human, wherein the air sample comprises a plurality of gaseous compounds comprising a mixture of at least ambient air, a first gaseous compound, and a second gaseous compound;
  a sensor array in the collection module wherein:
    the sensor array comprises at least a first sensor and a second sensor;
    the first sensor comprises a first metal oxide semiconductor material configured to generate:
      a first electrical resistance value in response to the ambient air;
      a second electrical resistance value in response to a reduction or oxidation reaction of the first gaseous compound when mixed with the ambient air;
      a third electrical resistance value in response to a reduction or oxidation reaction of the second gaseous compound when mixed with the ambient air; and
      a fourth electrical resistance value in response to a reduction or oxidation reaction of the air sample;
    the second sensor comprises a second metal oxide semiconductor material configured to generate:
      a fifth electrical resistance value in response to the ambient air;
      a sixth electrical resistance value in response to a reduction or oxidation reaction of the first gaseous compound when mixed with the ambient air;
      a seventh electrical resistance value in response to a reduction or oxidation reaction of the second gaseous compound when mixed with the ambient air; and
      an eighth electrical resistance value in response to a reduction or oxidation reaction of the air sample;
    the first sensor and the second sensor are chosen so that:
      the second electrical resistance value is not equal to the third electrical resistance value, the sixth electrical resistance value, or the seventh electrical resistance value;
      the third electrical resistance value is not equal to the sixth electrical resistance value or the seventh electrical resistance value; and
      the sixth electrical resistance value is not equal to the seventh electrical resistance value; and
  a detector circuit configured for:
    generating a first analog electrical signal in response to the first electrical resistance value;
    generating a second analog electrical signal in response to the fourth electrical resistance value;
    generating a third analog electrical signal in response to the fifth electrical resistance value;
    generating a fourth analog electrical signal in response to the eighth electrical resistance value;
    transmitting the first analog electrical signal and the third analog electrical signal through a first multiplexer in a configuration where the first analog electrical signal and the third analog electrical signal will appear at the same output of the multiplexer at different times during a test of the ambient air; and
    transmitting the second analog electrical signal and the fourth analog electrical signal through a multiplexer in a configuration where the second analog electrical signal and the fourth analog electrical signal will appear at the same output of the multiplexer at different times during a test of the air sample, wherein the multiplexer is selected from the group of the first multiplexer and a second multiplexer that is not the same as the first multiplexer;
  an analysis module configured for determining the health status in response to:
    a comparison of the relationship of the first analog electrical signal to the second analog electrical signal for the human;
    a comparison of the relationship of the third analog electrical signal to the fourth analog electrical signal for the human; and
    comparable data from air samples of other human subjects.

2. The electronic nose of claim 1 wherein:
the electronic nose further comprises a system controller;
the electronic nose further comprises a flow meter configured for producing a flow meter electrical signal in response to a rate of flow of gaseous compound through the collection module, the collection module is configured to collect an exhaled breath air sample;
the first metal oxide semiconductor material is the same as the second metal oxide semiconductor material;
the differences between the second resistance value and the sixth electrical resistance value are the result of differences of heater voltages of the first sensor and the second sensor;

differences between the third resistance value and the seventh electrical resistance value are the result of differences of heater voltages of the first sensor and the second sensor;

the detector circuit further comprises a first voltage divider circuit further comprising a first digital potentiometer and a second voltage divider circuit comprising a second digital potentiometer wherein:

the first voltage divider circuit is responsive to the electrical resistance of the first sensor;

the second voltage divider circuit is responsive to the electrical resistance of the second sensor;

the first digital potentiometer is configured for adjusting an output value of the first voltage divider circuit to increase a dynamic range and resolution of resistance values of the first sensor that are accurately read by the detector circuit; and the second digital potentiometer is configured for adjusting an output value of the second voltage divider circuit to increase a dynamic range and resolution of resistance values of the second sensor that are accurately read by the detector circuit;

the detector circuit further comprises:

an analog to digital converter that converts the output of the multiplexer to a digital signal; and a processor configured for storing the digital signal and transmitting the digital signal to the system controller;

the system controller is configured for receiving digital signals from a plurality of detector circuits to be processed by the analysis module for determining the health status;

the analysis module is further configured for determining the health status in response to information from the flow meter;

the health status further comprises a health status score; and the health status score is configured to be used to control performance of a medical procedure.

3. The electronic nose of claim 1 wherein:

the first metal oxide semiconductor material is the same as the second metal oxide semiconductor material; and the differences between the second resistance value and the sixth electrical resistance value are the result of differences of heater voltages of the first sensor and the second sensor; or differences between the third resistance value and the seventh electrical resistance value are the result of differences of heater voltages of the first sensor and the second sensor.

4. The electronic nose of claim 1 wherein:

the first metal oxide semiconductor material is different from the second metal oxide semiconductor material.

5. The electronic nose of claim 1 wherein:

the collection module is configured to collect an exhaled breath air sample.

6. The electronic nose of claim 1 wherein:

the detector circuit further comprises a first voltage divider circuit further comprising a first digital potentiometer and a second voltage divider circuit comprising a second digital potentiometer wherein:

the first voltage divider circuit is responsive to the electrical resistance of the first sensor;

the second voltage divider circuit is responsive to the electrical resistance of the second sensor;

the first digital potentiometer is configured for adjusting an output value of the first voltage divider circuit to increase a dynamic range and resolution of resistance values of the first sensor that are accurately read by the detector circuit; and the second digital potentiometer is configured for adjusting an output value of the second voltage divider circuit to increase a dynamic range and resolution of resistance values of the second sensor that are accurately read by the detector circuit.

7. The electronic nose of claim 1 wherein:

the detector circuit further comprises a first Wheatstone bridge circuit and a second Wheatstone bridge circuit wherein:

the first Wheatstone bridge circuit comprises the first sensor as one of the resistances in the first Wheatstone bridge circuit; and the second Wheatstone bridge circuit comprises the second sensor as one of the resistances in the second Wheatstone bridge circuit.

8. The electronic nose of claim 1 wherein:

the detector circuit further comprises an analog circuit element that generates a linear change in an output signal in response to a logarithmic change in an input signal.

9. The electronic nose of claim 1 wherein:

the health status further comprises a health status score; and the health status score is configured to be used to control performance of a medical procedure.

10. The electronic nose of claim 1 wherein:

the electronic nose further comprises a flow meter configured for producing a flow meter electrical signal in response to a rate of flow of the gaseous compound through the collection module;

the analysis module is further configured for determining the health status in response to information from the flow meter.

11. The electronic nose of claim 1 wherein:

the sensor array comprises at least ten sensors, further comprising a third sensor, a fourth sensor, a fifth sensor, a sixth sensor, a seventh sensor, an eighth sensor, a ninth sensor, and a tenth sensor wherein:

each sensor comprises a metal oxide semiconductor material; and each sensor generates different electrical resistance changes in electrical resistance values when exposed to a same gaseous compound;

the detector circuit generates a separate analog electrical signal in response to each sensor; and the analysis module is configured for determining the health status in response to all of the separate analog electrical signals from all of the sensors.

12. The electronic nose of claim 1 wherein:

the electronic nose further comprises a system controller;

the detector circuit further comprises:

an analog to digital converter that converts the output of the multiplexer to a digital signal; and a processor configured for storing the digital signal and transmitting the digital signal to the system controller;

the system controller is configured for receiving digital signals from a plurality of detector circuits to be processed by the analysis module for determining the health status.

13. The electronic nose of claim 1 wherein:

the detector circuit is further configured to produce:

a first digital electrical signal that is proportional to the first electrical resistance value;

a second digital electrical signal that is proportional to the fourth electrical resistance value;
a third digital electrical signal that is proportional the fifth electrical resistance value; and
a fourth digital electrical signal that is proportional to the eight electrical resistance value; and
the analysis module further determines the health status in response to:
a ratio of the first digital electrical signal and the second digital electrical signal; and
a ratio of the third digital electrical signal to the fourth digital electrical signal.

14. A system for analyzing an air sample from a human, the system comprising:
a collection module for receiving the air sample wherein:
the collection module comprises a plurality of sensors comprising at least a first sensor and a second sensor;
the first sensor and the second sensor comprise a metal oxide semiconductor material that generates electrical resistance values that vary in response to changes in concentrations of compounds in a gaseous air mixture;
the resistance values of the first sensor and second sensor to different gaseous compounds are dissimilar;
a detector circuit configured to:
generate electrical signals in response to:
a first resistance of the first sensor when exposed to ambient air;
a second resistance of the first sensor when exposed to the air sample;
a first resistance of the second sensor when exposed to the ambient air, and
a second resistance of the second sensor when exposed to the air sample; and
transmit the electrical signals wherein:
the detector circuit is configured to transmit the first resistance electrical signal from the first sensor and the first resistance electrical signal from the second sensor through a first multiplexer in a configuration wherein said two electrical signals will appear at a same output of the first multiplexer at different times;
the detector circuit is configured to transmit the second resistance electrical signal from the first sensor and the second resistance electrical signal from the second sensor through a multiplexer in a configuration wherein said two electrical signals will appear at the same output of the multiplexer at different times; and the multiplexer is selected from the group of the first multiplexer and a second multiplexer that is not the same as the first multiplexer; and
an analysis module configured for determining a health status for the human in response to:
said four electrical signals; and
comparable data received from air samples from other human subjects.

15. The system of claim 14 wherein:
first sensor and the second sensor comprise the same metal oxide semiconductor material; and differences in the resistance values of the first sensor and the second sensor to different gaseous compounds is a result of the first sensor and second sensor metal oxide semiconductor materials being heated to a different temperature by applying a different heater voltage.

16. The system of claim 14 wherein:
the detector circuit comprises a Wheatstone bridge circuit;
the Wheatstone bridge circuit comprises the first sensor as one of the resistances; and
the Wheatstone bridge circuit comprises at least one externally controlled variable resistor.

17. The system of claim 14 wherein:
the system is configured for analysis of human breath samples to determine whether to perform a medical procedure.

18. The system of claim 14 wherein:
the collection module further comprises a least third, fourth, and fifth sensor; and
the analysis module is responsive to outputs of the third, fourth, and fifth sensors.

19. The system of claim 14 wherein:
the first sensor comprises a first metal oxide semiconductor material;
the second sensor comprises a second metal oxide semiconductor material;
the first metal oxide semiconductor material is different from the second metal oxide semiconductor material; and
a temperature of the first metal oxide semiconductor material is different from a temperature of the second metal oxide semiconductor material when determining the health status.

20. A method for analyzing an air sample from a human, the air sampling method comprising the steps of:
receiving the air sample in a collection module wherein:
the collection module comprises a first sensor and a second sensor;
the first sensor and second sensor comprise a metal oxide semiconductor material responsive to changes in chemical concentrations in a gaseous air mixture;
the electrical response of the first sensor and the second sensor to changes in chemical concentrations in the gaseous mixture are different;
generating a first electrical signal in response to an exposure of the first sensor to ambient air;
generating a second electrical signal in response to an exposure of the first sensor to the air sample;
generating a third electrical signal in response to an exposure of the second sensor to ambient air;
generating a fourth electrical signal in response to an exposure of the second sensor to the air sample;
transmitting the first electrical signal and the third electrical signal through a multiplexer that is configured so that the first and third electrical signals will appear on the same output of the multiplexer at different times;
similarly transmitting the second and the fourth electrical signals through another, or the same multiplexer;
analyzing the first, second, third, and fourth electrical signals and comparable data taken from air samples from other human subjects to determine the health status of the human.

* * * * *